US006512098B2

(12) United States Patent
Jones et al.

(10) Patent No.: US 6,512,098 B2
(45) Date of Patent: *Jan. 28, 2003

(54) CHEMICALLY MODIFIED PROTEINS WITH A CARBOHYDRATE MOIETY

(75) Inventors: J. Bryan Jones, 1275 Seaforth Crescent, RR 3, Lakefield, Ontario (CA), K0L 2H0; Benjamin G. Davis, Durham (GB)

(73) Assignees: Genencor International, Inc., Palo Alto, CA (US); J. Bryan Jones, Ontario (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 94 days.

(21) Appl. No.: 09/347,029

(22) Filed: Jul. 2, 1999

(65) Prior Publication Data

US 2001/0018200 A1 Aug. 30, 2001

Related U.S. Application Data

(60) Provisional application No. 60/131,446, filed on Apr. 28, 1999, and provisional application No. 60/091,687, filed on Jul. 2, 1998.

(51) Int. Cl.$^7$ .......................... C07K 1/00; C07K 14/00; C07K 17/00; C07H 21/02; C07H 21/04

(52) U.S. Cl. ........................ 530/408; 435/7.6; 435/183; 435/193; 435/222; 435/441; 530/350; 530/395; 530/402; 530/404; 530/411; 532/29.13

(58) Field of Search .......................... 435/7.6, 183, 193, 435/441, 222; 532/29.13; 530/350, 395, 402, 404, 411, 408

(56) References Cited

U.S. PATENT DOCUMENTS

| | | |
|---|---|---|
| 5,208,158 A | 5/1993 | Bech et al. |
| 5,244,791 A | 9/1993 | Estell |
| 5,316,935 A | 5/1994 | Arnold et al. |
| 5,316,941 A | 5/1994 | Estell et al. |
| 5,340,735 A | 8/1994 | Christianson et al. |
| 5,403,737 A | 4/1995 | Abrahmsen et al. |
| 5,629,173 A | 5/1997 | Abrahmsen et al. |
| 5,955,340 A | 9/1999 | Bott et al. |

FOREIGN PATENT DOCUMENTS

| | | |
|---|---|---|
| EP | 0 328 229 A1 | 8/1989 |
| WO | WO 91/16423 | 4/1991 |
| WO | WO 96/27671 | 2/1996 |
| WO | WO 97/37007 | 10/1997 |
| WO | WO 98/23732 | 6/1998 |
| WO | WO 99/20723 | 4/1999 |
| WO | WO 99/37323 | 7/1999 |
| WO | WO 99/37324 | 7/1999 |
| WO | WO 00/01712 | 1/2000 |

OTHER PUBLICATIONS

Berglund et al. Altering the specificity of subtilisin B.lentus by combining site–directed mutagenesis and chemical modification. Bioorg. Med. Chem. Lett., 1996, vol. 6:2507–2512.*

Bech et al., "Significane of Hydrophobics $S_4$ —$P_4$ Interactions in Subtilism 309 from *Bacillus Ientus*," *Biochemistry*, 32:2847–2852, (1993).

Bech, L. M. et al., "Chemical Modification of a Cysteinyl Residue Introduced in the Binding Site of Carboxypeptidase Y by Site–Directed Mutagenesis," *Carlsberg Research Communications*,(1988) vol. 53, pp. 381–393, XP002063095.

Bergland, P. et al., "Chemical Modification of Cystein Mutants of Subtilisin Bacillus Lentus Can Create Better Catalysts Than the Wild–Type Enzyme," *J. Am. Chem. Soc.*,119:5265–5266 (1997).

Berglund et al., "Altering the Specificity of Subtilisin *B. Lentus*,by Combining Site–Directed Mutagenesis and Chemical Modification," *Bioorganic & Mechanical Chemistry Letters*,6:2507–2512.

Betzel et al., "Crystal Structure of the Alkaline Proteinase Savinase™ from *Bacillus lentus* at 14 Å Resolution,"*J. Mol. Biol.*, 223:427–445(1995).

Bonneau et al., "Alteration of the Specificity of Subtilisin BPN' by Site–Directed Mutagenesis in its $S_1$ and $S_1$' Binding Sites," *J. Am. Chem. Soc.*,113:1026–30 (1991).

Brocklehurst, "Specific Covalent Modification of Thiols: Applications in the Study of Enzymes and Other Biomolecules,"*Int. J. Biochem.*,10:259–274 (1979).

Bruice et al., "Novel Alkyl Alkanethiolsulfonate Sulfhydryl Reagents. Modification of Derivatives of L–Cysteine,"*Journal of Protein Chemistry*, 1:47–58 (1982).

Chen et al., "Probing the S–1' Subsite Selectivity of an Industrial Alkaline Protease in Anhydrous t–Butanol," *Bioorganic & Medicinal Chemistry Letters*, 3(4):727–33 (1993).

(List continued on next page.)

*Primary Examiner*—Rebecca E. Prouty
*Assistant Examiner*—Manjunath N. Rao
(74) *Attorney, Agent, or Firm*—McCutchen, Doyle, Brown & Enersen, LLP; Michael J. Shuster

(57) ABSTRACT

The present invention relates to a chemically modified mutant protein including a cysteine residue substituted for a residue other than cysteine in a precursor protein, the substituted cysteine residue being subsequently modified by reacting the cysteine residue with a glycosylated thiosulfonate. Also, a method of producing the chemically modified mutant protein is provided. The present invention also relates to a glycosylated methanethiosulfonate. Another aspect of the present invention is a method of modifying the functional characteristics of a protein including providing a protein and reacting the protein with a glycosylated methanethiosulfonate reagent under conditions effective to produce a glycoprotein with altered functional characteristics as compared to the protein. In addition, the present invention relates to methods of determining the structure-function relationships of chemically modified mutant proteins.

10 Claims, 19 Drawing Sheets

OTHER PUBLICATIONS

Davies et al., "A Semisynthetic Metalloenzyme Based on a Protein Cavity That Catalyzes the Enantiosleective Hydrolysis of Ester and Amide Substrates," *J. Am. Chem. Soc.,* 119:11643–11652 (1997).

Davis, B. G., et al., "Altering the specificity of subtilisin *Bacillus lentus* through the introduction of positive charge at single amino acid sites," *Bioorganic and Medicinal Chemistry,* (Nov. 1999) 7 (11) 2303–11, XP0000892841.

Davis, B. G., et al. "Controlled site selective glycosylation of proteins by a combined site directed mutagenesis and chemical modification approach," *J. Org., Chem.,* vol. 63, (1998), pp. 9614–9615, XP002135378.

Davis, B. G., et al., "Controlled site selective protein glycosilation for precise glycan structure catalytic activity relationships," *Bioorganic & Medicinal Chemistry,* 8, 1527–1535, (2000), XP000986502.

Davis, B. G., et al., "Glycomethanethiosulfonates: powerful reagants for protein glycosylation," *Tetrahedron: Asymmetry, NL, Elsevier Science Publishers,* Amsterdam, 11:1, 245–262 (2000–01), XP004191784.

Davis, B. G., et al., "The controlled introduction of multiple negative charge at single amino acis sites in subtilism *Bacillus lentus,*" *Bioorganic and Medicinal Chemistry,* (Nov. 1999) 7 (11):2293–301,XP0000892840.

DeSantis et al., "Chemical Modifications at a Single Site Can Induce Significant Shifts in the pH Profiles of a Serine Protease," *J. Am Chem. Soc.,* 120:8582–8586 (1998).

DeSantis et al., "Site–Directed Mutagenesis Combined with Chemical Modification as a Strategy for Altering the Specificity of the S1 and S1' Pockets of Subtilisin *Bacillus Ientus,* "*Biochemistry,* 37:5968–5973 (1998), XP002135377.

Desantis, G. et al., "Probing the altered specificity and catalytic properties of mutant subtilisin chemically modified at position S156C and S166C in the S1 pocket," *Bioorrganic and Medicinal Chemistry,* (1997) 7/7: (1381–1380, XP0000892843.

Dickman, M., et al., "Chemically Modified Mutants of Subtilism *Bacillus lentus* catalyze transesterification reactions better than wild type," *Tetrahedron Asymmetry,* (Dec. 11, 1998) 9/23:4099–4102.

Kaiser, "Catalytic Activity of Enzymes Altered at Their Active Sites," *Agnew. Chem. Int. Ed. Engl.,* 27:913–922;(1988).

Kawase et al., "Effect of Chemical Modification of tyrosine Residues on Activities of Bacterial Lipase," *Journal of Fermentation and Bioengineering,* 72:317–319 (1991).

Kenyon et al., "Novel Sulfhydryl Reagents," *Methods Enzymol.,* 47:407–430 (1977).

Kluger et al., "Amino Group Reactions of the Sulfhydryl Reagent Methyl Methanesulfonothioate. Inactivation of D–3–hydroxybutyrate Dehydrogenase and Reaction with Amines in Water," *Can. J. Biochem.,* 58:629–632 (1980).

Lloyd, R.C. et al., "Site selective glycosilation of subtilism bacillus lentus causes dramatic increase in esterase activity,"*Biorganic & Medicinal Chemistry,*8, 1537–1544 (2000), XP000986506.

Lo, Bryan, et al., "replacement of Ala–166 with Cysteine in the High Affinity Rabbit SodiumBlucose Transporter Alters Transpoert Kinetics and Allows Methanethiosulfonate Ethylamine to Inhibit Transporter Function", *The Journal of Biological Chemistry,*273:2 903–909 (1998).

Neet, K.E. and Koshland, D.E., "The Conversion of Serine at the Active of Subtilism to Cysteine:A'Chemical Mutation, "*Proc. Nat. Acad. Sci. USA,*56(5):1606–1611.

Nishimura et al., "Reversible Modification of the Sulfhydryl Groups of *Escherichia coli*SuccinicThiokinase with Methanethiolating Reagent, 5,5'–Dithio–bis(2–Nitrobenzoic Acid), p–Hydroxymercuribenzoate, and Ethylmercurithiosalicylate,"*Achives of Biochemistry and Biophysics,* 170:461–467 (1975).

Paulson, J.C., "Glycoproteins: what are the sugar chains for?"TIBS, 14:272–276 (1989).

Planas et al., "Reengineering the Catalytic Lysine of Aspartate Aminotransferase by Chemical Elaboration of a Genetically Introduced Cysteine,"*Biochemistry,*30:8268–8276 (1991).

Plettner et al., "A Combinatorial Approach to Chemical Modification of Subtilism *Bacillus Ientus,* "*Bioorganic & Medicinal Chemistry Letters,*8:2291–2296 (1998), XP004138220.

Polgar et al., "A New Enzyme Containing a Synthetically Formed Active Site. Thiol–Subtilisn,"*Journal of American Chemical Society,*88:3153–3154 (1966).

Ramachandran et al., "Stabilization of Barstar by Chemical Midification of the Buried Cysteines,"Biochemistry, 35:8776–8785 (1996).

Roberts et al., "Reactivity of Small Thiolate Anions and Cysteine–25 in Papain Toward Methyl Methanethiosulfonate", *Biochemistry,* 25:5595–5601 (1986).

Siddiqui et al., "Arthrobacter D–Xylose Isomerase: Chemical Modification of Carboxy Groups and Protein Engineering of pH Optimum," *Biochem. J.,* 295:685–691 (1993).

Smith et al., "An Engineered Change in Substrate Specificity of Ribulosebisphosphate Carboxylase/Oxygenase," *The Journal of Biological Chemistry,* 265:1243–1245 (1990).

Smith et al., "Chemical Modification of Active Site Residues in γ–Glutamyl Transpeptidase," *The Journal of Biological Chemistry,* 270:12476–12480 (1995).

Smith et al., "Restoration of Activity to Catalytically Deficient Mutants of Ribulosebisphosphate Carboxylase/Oxygenase by Aminoethylation," *The Journal of Biological Chemistry,* 263:4921–4925 (1988).

Smith et al., "Simple Alkanethiol Groups for Temporary Blocking of Sulfhydryl Groups of Enzymes," *Biochemistry,* 14:766–771 (1975).

Smith et al., "Subtle Alteration of the Active Site of Ribulose Bisphosphate Carboxylase/Oxygenase by Concerted Site–Directed Mutagenesis and Chemical Modification," *Biochemical and Biophyscial Research Communications,* 152:579–584 (1988).

Spura, Armin, et al., "Probing the Agonist Domain of the Nicotinic Acetylcholine Receptor by Cysteine Scanning Mutagenesis Reveals Residues in Proximity to the α–Bungarotoxin Binding Site", *Biochemistry,* 38:4912–4921 (1999).

Stewart et al., "Catalytic Oxidation of Dithiols by a Semisynthetic Enzyme," *J. Am. Chem. Soc.,* 108:3480–3483 (1986).

Valenzuela et al., "Kinetic Properties of Succinylated and Ethylenediamine–Amidated δChymotrypsins," *Biochim. Biophys. Acta,* 250:538–548 (1971).

West et al., "Enzymes as Synthetic Catalysts: Mechanistic and Active–Site Considerations of Natural and Modified Chymotrypsin," *J. Am. Chem. Soc.,* 112:5313–5320 (1990).

White et al., "Sequential Site–Directed Mutagenesis and Chemical Modification to Convert the Active Site Arginine 292 of Aspartate Aminotransferase to Homoarginine," *Journal of the American Chemical Society,* 114:292–293 (1992).

Wynn et al., "Chemical Modification of Protein Thiols: Formation of Mixed Disulfides," *Methods in Enzymology,* 251:351–356 (1995).

Wynn et al., "Comparison of Straight Chain and Cycle Unnatural Amino Acids Embedded in the Core of Staphylococcal Nuclease," *Protein Science,* 6:1621–1626 (1997).

Wynn et al., "Mobile Unnatural Amino Acid Site Chains in the Core of Staphylococcal Nuclease," *Protein Science,* 5:1026–1031 (1996).

Wynn et al., "Unnatural Amino Acid Packing Mutants of *Escherichia Coli* Thioredoxin Produced by Combined Mutagenesis/Chemical Modification Techiques," *Protein Science,* 2:395–403 (1993).

* cited by examiner

CHEMICALLY MODIFIED PROTEINS WITH A CARBOHYDRATE MOIETY

CROSS-REFERENCE TO RELATED APPLICATIONS

This application claims the benefit of U.S. Provisional Patent Application Ser. No. 60/091,687, filed Jul. 2, 1998, and U.S. Provisional Patent Application Ser. No. 60/131,446, filed Apr. 28, 1999, and which are hereby incorporated by reference.

FIELD OF THE INVENTION

The present invention relates to chemically modified mutant proteins having modified glycosylation patterns with respect to a precursor protein from which they are derived. In particular, the present invention relates to a chemically modified mutant protein including a cysteine residue substituted for a residue other than cysteine in a precursor protein, the substituted cysteine residue being subsequently modified by reacting the cysteine residue with a glycosylated thiosulfonate. The present invention also relates to a method of producing the chemically modified mutant proteins and a glycosylated methanethiosulfonate. Another aspect of the present invention is a method of modifying the functional characteristics of a protein by reacting the protein with a glycosylated methanethiosulfonate reagent. The present invention also relates to methods of determining the structure-function relationships of chemically modified mutant proteins.

BACKGROUND OF THE INVENTION

Modifying enzyme properties by site-directed mutagenesis has been limited to natural amino acid replacements, although molecular biological strategies for overcoming this restriction have recently been derived (Cornish et al., *Angew. Chem.*, Int. Ed. Engl., 34:621–633 (1995)). However, the latter procedures are difficult to apply in most laboratories. In contrast, controlled chemical modification of enzymes offers broad potential for facile and flexible modification of enzyme structure, thereby opening up extensive possibilities for controlled tailoring of enzyme specificity.

Changing enzyme properties by chemical modification has been explored previously, with the first report being in 1966 by the groups of Bender (Polgar et al., *J. Am. Chem. Soc.*, 88:3153–3154 (1966)) and Koshland (Neet et al., *Proc. Natl. Acad. Sci. USA*, 56:1606–1611 (1966)), who created a thiolsubtilisin by chemical transformation ($CH_2OH \rightarrow CH_2SH$) of the active site serine residue of subtilisin BPN' to cysteine. Interest in chemically produced artificial enzymes, including some with synthetic potential, was renewed by Wu (Wu et al., *J. Am. Chem. Soc.*, 111:4514–4515 (1989); Bell et al., *Biochemistry*, 32:3754–3762 (1993)) and Peterson (Peterson et al., *Biochemistry*, 34:6616–6620 (1995)), and, more recently, Suckling (Suckling et al., *Bioorg. Med. Chem. Lett.*, 3:531–534 (1993)).

Enzymes are now widely accepted as useful catalysts in organic synthesis. However, natural, wild-type, enzymes can never hope to accept all structures of synthetic chemical interest, nor always be transformed stereospecifically into the desired enantiomerically pure materials needed for synthesis. This potential limitation on the synthetic applicabilities of enzymes has been recognized, and some progress has been made in altering their specificities in a controlled manner using the site-directed and random mutagenesis techniques of protein engineering. However, modifying enzyme properties by protein engineering is limited to making natural amino acid replacements, and molecular biological methods devised to overcome this restriction are not readily amenable to routine application or large scale synthesis. The generation of new specificities or activities obtained by chemical modification of enzymes has intrigued chemists for many years and continues to do so.

U.S. Pat. No. 5,208,158 to Bech et al. ("Bech") describes chemically modified detergent enzymes where one or more methionines have been mutated into cysteines. The cysteines are subsequently modified in order to confer upon the enzyme improved stability towards oxidative agents. The claimed chemical modification is the replacement of the thiol hydrogen with $C_{1-6}$ alkyl.

Although Bech has described altering the oxidative stability of an enzyme through mutagenesis and chemical modification, it would also be desirable to develop one or more enzymes with altered properties such as activity, nucleophile specificity, substrate specificity, stereoselectivity, thermal stability, pH activity profile, and surface binding properties for use in, for example, detergents or organic synthesis. In particular, enzymes, such as subtilisins, tailored for peptide synthesis would be desirable. Enzymes useful for peptide synthesis have high esterase and low amidase activities. Generally, subtilisins do not meet these requirements and the improvement of the esterase to amidase selectivities of subtilisins would be desirable. However, previous attempts to tailor enzymes for peptide synthesis by lowering amidase activity have generally resulted in dramatic decreases in both esterase and amidase activities. Previous strategies for lowering the amidase activity include the use of water-miscible organic solvents (Barbas et al., *J. Am. Chem. Soc.*, 110:5162–5166 (1988); Wong et al., *J. Am. Chem. Soc.*, 112:945–953 (1990); and Sears et al., *Biotechnol. Prog.*, 12:423–433 (1996)) and site-directed mutagenesis (Abrahamsen et al., *Biochemistry*, 30:4151–4159 (1991); Bonneau et al., "Alteration of the Specificity of Subtilisin BPN' by Site-Directed Mutagenesis in its S1 and S1' Binding-Sites," *J. Am. Chem. Soc.*, 113:1026–1030 (1991); and Graycar et al., *Ann. N. Y. Acad. Sci.*, 67:71–79 (1992)). However, while the ratios of esterase-to-amidase activities were improved by these approaches, the absolute esterase activities were lowered concomitantly. Abrahamsen et al., *Biochemistry*, 30:4151–4159 (1991). Chemical modification techniques (Neet et al., *Proc. Nat. Acad. Sci.*, 56:1606 (1966); Polgar et al., *J. Am. Chem. Soc.*, 88:3153–3154 (1966); Wu et al., *J. Am. Chem. Soc.*, 111:4514–4515 (1989); and West et al., *J. Am. Chem. Soc.*, 112:5313–5320 (1990)), which permit the incorporation of unnatural amino acid moieties, have also been applied to improve esterase to amidase selectivity of subtilisins. For example, chemical conversion of the catalytic triad serine (Ser221) of subtilisin to cysteine (Neet et al., *Proc. Nat. Acad. Sci.*, 56:1606 (1966); Polgar et al., *J. Am. Chem. Soc.*, 88:3153–3154 (1966); and Nakatsuka et al., *J. Am. Chem. Soc.*, 109:3808–3810 (1987)) or to selenocysteine (Wu et al., *J. Am. Chem. Soc.*, 111:4514–4515 (1989)), and methylation of the catalytic triad histidine (His57) of chymotrypsin (West et al., *J. Am. Chem. Soc.*, 112:5313–5320 (1990)), effected substantial improvement in esterase-to-amidase selectivities. Unfortunately however, these modifications were again accompanied by 50- to 1000-fold decreases in absolute esterase activity.

Surface glycoproteins act as markers in cell-cell communication events that determine microbial virulence (Sharon et al., *Essays Biochem.*, 30:59–75 (1995)), inflammation (Lasky, *Annu. Rev. Biochem.*, 64:113–139 (1995); Weis et al., *Annu. Rev. Biochem.*, 65:441–473 (1996)), and host immune responses (Varki, *Glycobiol.*, 3:97–130 (1993); Dwek, *Chem. Rev.*, 96:683–720 (1996)). In addition, the correct glycosylation of proteins is critical to their expression and folding (Helenius, *Mol. Biol. Cell*, 5:253–265 (1994)) and increases their thermal and proteolytic stability (Opdenakker et al., *FASEB J.*, 7:1330–1337(1993)). Glycoproteins occur naturally in a number of forms (glycoforms) (Rademacher et al., *Annu. Rev. Biochem.*, 57:785–838 (1988)) that possess the same peptide backbone, but differ in both the nature and site of glycosylation. The differences exhibited (Rademacher et al., *Annu. Rev. Biochem.*, 57:785–838 (1988); Parekh et al., *Biochem.*, 28:7670–7679 (1989); Knight, *Biotechnol.*, 7:35–40 (1989)) by each component within these microheterogeneous mixtures present regulatory difficulties (Liu, *Trends Biotechnol.*, 10:114–120 (1992); Bill et al., *Chem. Biol.*, 3:145–149 (1996)) and problems in determining exact function. To explore these key properties, there is a pressing need for methods that will not only allow the preparation of pure glycosylated proteins, but will also allow the preparation of non-natural variants for the determination of structure-function relationships, such as structure-activity relationships (SARs). The few studies that have compared single glycoforms successfully have required abundant sources and extensive chromatographic separation (Rudd et al., *Biochem.*, 33:17–22 (1994)). Neoglycoproteins (Krantz et al., *Biochem.*, 15:3963–3968 (1976)), formed via unnatural linkages between sugars and proteins, provide an invaluable alternative source of carbohydrate-protein conjugates (For reviews see Stowell et al., *Adv. Carbohydr. Chem. Biochem.*, 37:225–281 (1980); *Neoglycoconjugates: Preparation and Applications*, Lee et al., Eds., Academic Press, London (1994); Abelson et al., *Methods Enzymol.*, 242: (1994); Lee et al., *Methods Enzymol.*, 247: (1994); Bovin et al., *Chem. Soc. Rev.*, 24:413–421 (1995)). In particular, chemical glycosylation allows control of the glycan structure and the nature of the sugar-protein bond. However, despite these advantages, existing methods for their preparation (Stowell et al., *Adv. Carbohydr. Chem. Biochem.*, 37:225–281 (1980)) typically generate mixtures. In addition, these techniques may alter the overall charge of the protein (Lemieux et al., *J. Am. Chem. Soc.*, 97:4076–4083 (1975); Kobayashi et al., *Methods Enzymol.*, 247:409–418 (1994)) or destroy the cyclic nature of glycans introduced (Gray, *Arch. Biochem. Biophys.*, 163:426–428 (1974)). For example, the reductive amination of lactose with bovine serum albumin (BSA) caused indiscriminate modification of lysine residues through the formation of acyclic amines introduced (Gray, *Arch. Biochem. Biophys.*, 163:426–428 (1974)). Advances in the site-specific glycosylation of BSA have been made (Davis et al., *Tetrahedron Lett.*, 32:6793–6796 (1991); Wong et al., *Biochem. J.*, 300:843–850 (1994); Macindoe et al., *J. Chem. Soc., Chem. Commun.*, 847–848 (1998)). However, these methods rely upon modification of an existing cysteine in BSA and, as such, allow no flexibility in the choice of glycosylation site. Glycoproteins occur naturally as complex mixtures of differently glycosylated forms which are difficult to separate. To explore their properties, there is a need for homogenous sources of carbohydrate-protein conjugates. Existing methods typically generate product protein mixtures of poorly characterized composition, with little or no control over the site or level of glycosylation.

The present invention is directed to overcoming these deficiencies.

SUMMARY OF THE INVENTION

It is an object of the present invention to provide for novel glycosylated proteins.

It is a further object of the invention to provide for novel glycosylated proteins which have modified or improved functional characteristics.

It is a further object of the invention to provide for a method of producing glycosylated proteins which have well defined properties, for example, by having predetermined glycosylation patterns.

According to the present invention, a method is provided wherein the glycosylation pattern of a protein is modified in a predictable and repeatable manner. Generally, the modification of the protein occurs via reaction of a cysteine residue in the protein with a glycosylated thiosulfonate.

Thus, in one composition aspect of the present invention, a chemically modified mutant protein is provided, wherein said mutant protein differs from a precursor protein by virtue of having a cysteine residue substituted for a residue other than cysteine in said precursor protein, the substituted cysteine residue being subsequently modified by reacting said cysteine residue with a glycosylated thiosulfonate. Preferably, the glycosylated thiosulfonate is an alkylthiosulfonate, most preferably a methanethiosulfonate.

In a method aspect of the present invention, a method of producing a chemically modified mutant protein is provided comprising the steps of: (a) providing a precursor protein; (b) substituting an amino acid residue other than cysteine in said precursor protein with a cysteine; (c) reacting said substituted cysteine with a glycosylated thiosulfonate, said glycosylated thiosulfonate comprising a carbohydrate moiety; and (d) obtaining a modified glycosylated protein wherein said substituted cysteine comprises a carbohydrate moiety attached thereto. Preferably, the glycosylated thiosulfonate is an alkylthiosulfonate, most preferably, a methanethiosulfonate. Also preferably, the substitution in said precursor protein is obtained by using recombinant DNA techniques by modifying a DNA encoding said precursor protein to comprise DNA encoding a cysteine at a desired location within the protein.

The present invention also relates to novel glycosylated thiosulfonates. In a preferred embodiment, the glycosylated thiosulfonate is a methanethiosulfonate. In a most preferred embodiment, the glycosylated methanethiosulfonate comprises a chemical structure including:

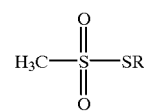

where R comprises -β-Glc, -Et-β-Gal, -Et-β-Glc, -Et-α-Glc, -Et-α-Man, -Et-Lac, -β-Glc(Ac)$_2$, -β-Glc(Ac)$_3$, -β-Glc(Ac)$_4$, -Et-α-Glc(Ac)$_2$, -Et-α-Glc(Ac)$_3$, -Et-α-Glc(Ac)$_4$, -Et-β-Glc(Ac)$_2$, -Et-β-Glc(Ac)$_3$, -Et-β-Glc(Ac)$_4$, -Et-α-Man(Ac)$_3$, -Et-α-Man(Ac)$_4$, -Et-β-Gal(Ac)$_3$, -Et-β-Gal(Ac)$_4$, -Et-Lac(Ac)$_5$, -Et-Lac(Ac)$_6$, or -Et-Lac(Ac)$_7$.

Another aspect of the present invention is a method of modifying the functional characteristics of a protein including reacting the protein with a glycosylated thiosulfonate reagent under conditions effective to produce a glycoprotein with altered functional characteristics as compared to the protein. Accordingly, the present invention provides for modified protein, wherein the protein comprises a wholly or partially predetermined glycosylation pattern which differs from the glycosylation pattern of the protein in its precursor, natural, or wild type state and a method for producing such a modified protein.

The present invention also relates to methods of determining the structure-function relationships of chemically modified mutant proteins. One method includes providing first and second chemically modified mutant proteins of the present invention, wherein the glycosylation pattern of the second chemically modified mutant protein differs from the glycosylation pattern of the first chemically modified mutant protein, evaluating a functional characteristic of the first and second chemically modified mutant proteins, and correlating the functional characteristic of the first and second chemically modified mutant proteins with the structures of the first and second chemically modified mutant proteins. Another method involves providing first and second chemically modified mutant proteins of the present invention, wherein at least one different cysteine residue in the second chemically modified mutant protein is modified by reacting said cysteine residue with a glycosylated thiosulfonate, evaluating a functional characteristic of the first and second chemically modified mutant proteins, and correlating the functional characteristic of the first and second chemically modified mutant proteins with the structures of the first and second chemically modified mutant proteins.

The chemically modified mutant proteins of the present invention provide an alternative to site-directed mutagenesis and chemical modification for introducing unnatural amino acids into proteins. Moreover, the methods of the present invention allow the preparation of pure glycoproteins (i.e., not mixtures) with predetermined and unique structures. These glycoproteins can then be used to determine structure-function relationships (e.g., structure-activity relationships ("SARs")) of non-natural variants of the proteins.

An advantage of the present invention is that it is possible to introduce predetermined glycosylation patterns into proteins in a simple and repeatable manner. This advantage provides an ability to modify critical protein characteristics such as partitioning, solubility, cell-cell signaling, catalytic activity, biological activity and pharmacological activity. Additionally, the methods of the present invention provide for a mechanism of "masking" certain chemically or biologically important protein sites, for example, sites which are critical for immunological or allergenic response or sites which are critical to proteolytic degradation of the modified protein.

Another advantage of the present invention is the ability to glycosylate a protein which is not generally glycosylated, or to modify the glycosylation pattern of a protein which is generally glycosylated.

Another advantage of the present invention is to produce enzymes which have altered catalytic activity. In one specific example, the inventors herein have shown that it is possible to modify the substrate specificity of a protease to increase the esterase activity as compared to the amidase activity. Similarly, modifications of substrate specificity would be expected when utilizing the present invention with other enzymes.

These and other advantages of the present invention are described in more detail in the following detailed description.

BRIEF DESCRIPTION OF THE DRAWINGS

FIGS. 13A–306D show esterase $k_{cat}/K_M$s for deprotected glyco-CMMs relative to WT. At position 62 (FIG. 13A), in the $S_1$ pocket, glycosylation leads to a series of enzymes that have similar activities that are 1.3- to 1.9-fold greater than WT. At position 217 (FIG. 13B cosylation pattern of the second chemically modified mutant protein differs from the glycosylation pattern of the first chemically modified mutant protein, evaluating a functional characteristic of the first and second chemically modified mutant proteins, and correlating the functional characteristic of the first and second chemically modified mutant proteins with the structures of the first and second chemically modified mutant proteins. The second method involves providing first and second chemically modified mutant proteins of the present invention, wherein at least one different cysteine residue in the second chemically modified mutant protein is modified by reacting said cysteine residue with a glycosylated thiosulfonate, evaluating a functional characteristic of the first and second chemically modified mutant proteins, and correlating the functional characteristic of the first and second chemically modified mutant proteins with the structures of the first and second chemically modified mutant proteins.

Figure 1:
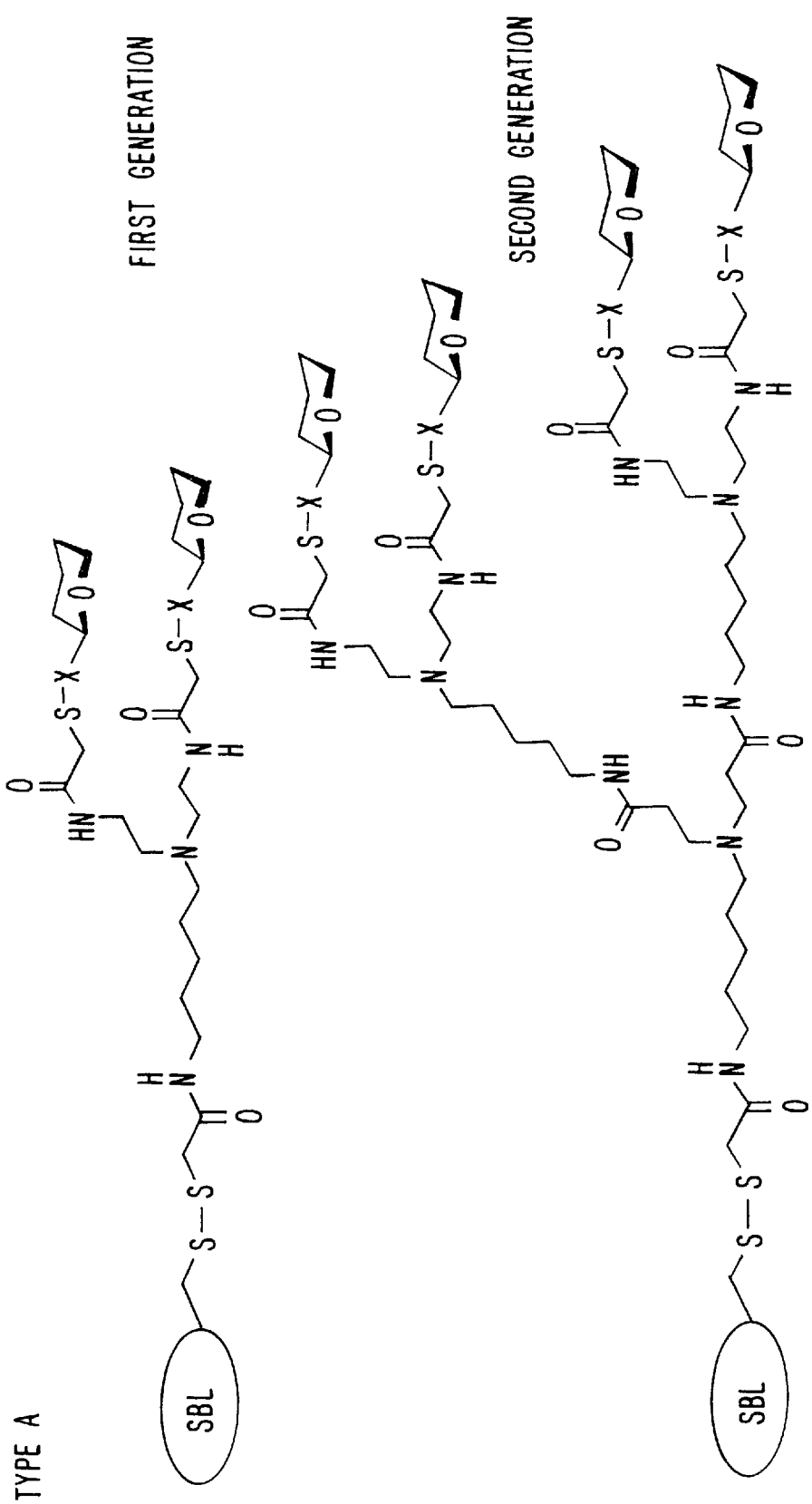
FIG. 1 shows dendrimer methanethiosulfonate ("MTS") reagents.
Figure 1:
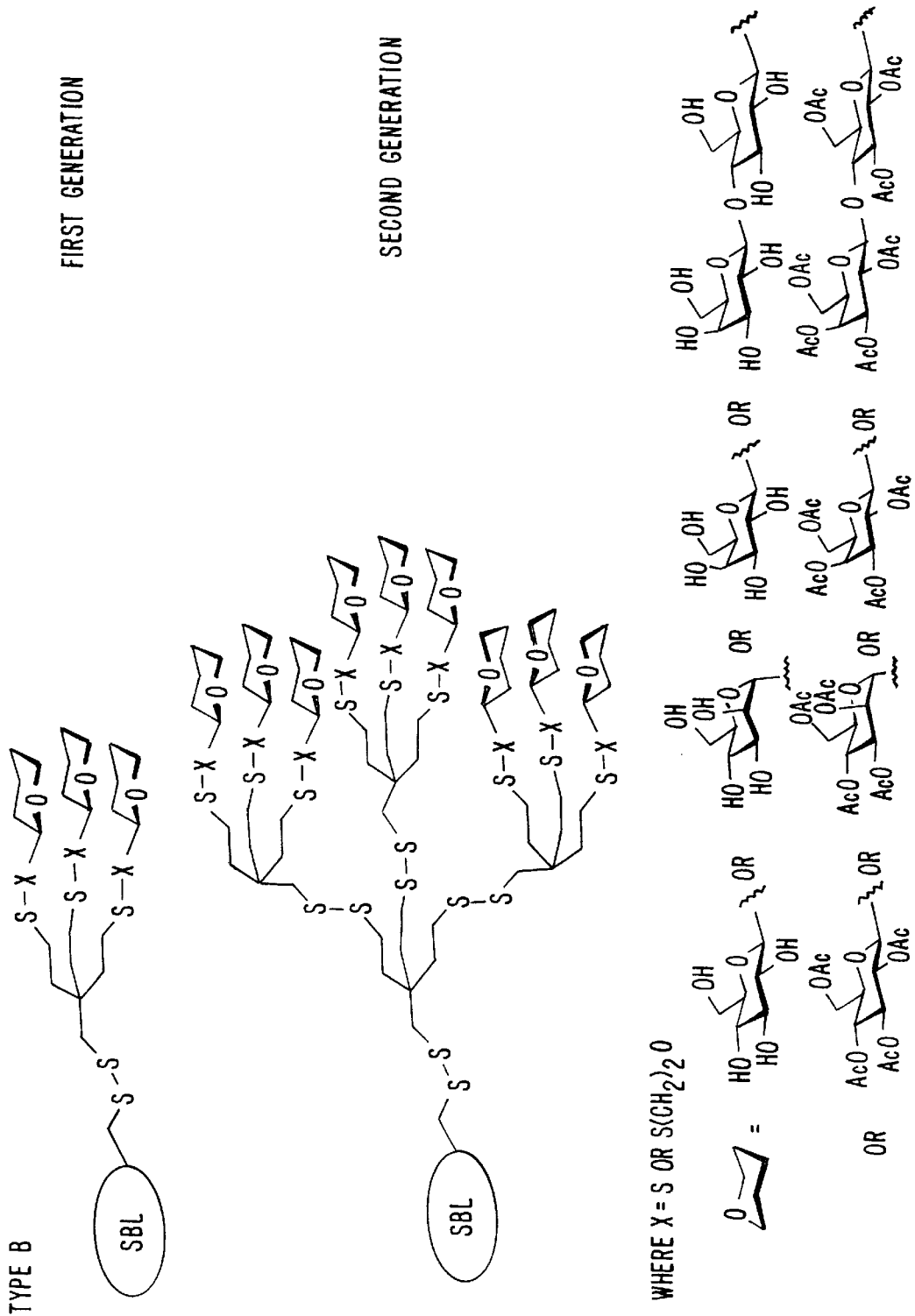

The chemically modified mutant proteins of the present invention provide a valuable source of carbohydrate-protein conjugates. Moreover, the methods of the present invention allow the preparation of pure and glycoproteins (i.e., not mixtures) with predetermined and unique structures. These glycoproteins can then be used to determine structure-function relationships (e.g., structure-activity relationships ("SARs")) of non-natural variants of the proteins.

The protein of the invention may be any protein for which a modification of the glycosylation pattern thereof may be desirable. For example, proteins which are naturally not glycosylated may be glycosylated via the invention. Similarly, proteins which exist in a naturally glycosylated form may be modified so that the glycosylation pattern confers improved or desirable properties to the protein. Specifically, proteins useful in the present invention are those in which glycosylation plays a role in functional characteristics such as, for example, biological activity, chemical activity, pharmacological activity, or immunological activity.

Glycosylated proteins as referred to herein means moieties having carbohydrate components which are present on proteins, peptides, or amino acids. In the present invention, the glycosylation is provided, for example, as a result of reaction of the glycosylated thiosulfonate with the thiol hydrogen of a cysteine residue thereby producing an amino acid residue which has bound thereto the carbohydrate component present on the glycosylated thiosulfonate.

Another aspect of the present invention is a method of modifying the functional characteristics of a protein including providing a protein and reacting the protein with a glycosylated thiosulfonate reagent under conditions effective to produce a glycoprotein with altered functional characteristics as compared to the protein.

The functional characteristics of a protein which may be altered by the present invention include, but are not limited to, enzymatic activity, the effect on a human or animal body, the ability to act as a vaccine, the tertiary structure (i.e., how the protein folds), whether it is allergenic, its solubility, its signaling effects, its biological activity, and its pharmacological activity (Paulson, "Glycoproteins: What are the Sugar Chains For?", Trends in Biochem. Sciences, 14:272–276 (1989), which is hereby incorporated by reference). The use of glycosylated thiosulfonates as thiol-specific modifying reagents in the method of the present invention allows virtually unlimited alterations of protein residues. In addition, this method allows the production of pure glycoproteins with predetermined and unique structures and, therefore, unique functional characteristics, with control over both the site and level of glycosylation. In particular, the method of modifying the functional characteristics of a protein allows the preparation of single glycoforms through regio- and glycan-specific protein glycosylation at predetermined sites. Such advantages provide an array of options with respect to modification of protein properties which did not exist in the prior art. The ability to produce proteins having very specific and predictable glycosylation patterns will enable the production of proteins which have known and quantifiable effects in chemical, pharmaceutical, immunological, or catalytic performance. For example, with knowledge of a specific problematic epitope, it would be possible to construct a modified protein according to the present invention in which the epitope is masked by a carbohydrate moiety, thus reducing its allergenic or immunogenic response in a subject. As another example, where the solubility of a protein is problematic in terms of recovery or formnulation in a pharmaceutical or industrial application, it may be possible, utilizing the present invention, to produce a protein which has altered solubility profiles thus producing a more desirable protein product. As another example, if a protein has particular problem of being proteolytically unstable in the environment in which it is to be used, then it may be possible to mask the proteolytic cleavage sites in the protein using the present invention to cover up such a site with a carbohydrate moiety. These examples are merely a few of the many applications of the present invention to produce improved proteins.

In a preferred embodiment, the protein is an enzyme. The term "enzyme" includes proteins that are capable of catalyzing chemical changes in other substances without being changed themselves. The enzymes can be wild-type enzymes or variant enzymes. Enzymes within the scope of the present invention include pullulanases, proteases, cellulases, amylases, isomerases, lipases, oxidases, and reductases. Preferably, the enzyme is a protease. The enzyme can be a wild-type or mutant protease. Wild-type proteases can be isolated from, for example, Bacillus lentus or Bacillus amyloliquefaciens (also referred to as BPN'). Mutant proteases can be made according to the teachings of, for example, PCT Publication Nos. WO 95/10615 and WO 91/06637, which are hereby incorporated by reference. Functional characteristics of enzymes which are suitable for modification according to the present invention include, for example, enzymatic activity, solubility, partitioning, cell-cell signaling, substrate specificity, substrate binding, stability to temperature and reagents, ability to mask an antigenic site, physiological functions, and pharmaceutical functions (Paulson, "Glycoproteins: What are the Sugar Chains For?", Trends in Biochem. Sciences, 14:272–276 (1989), which is hereby incorporated by reference).

The protein is modified so that a non-cysteine residue is substituted with a cysteine residue, preferably by recombinant means. Preferably, the amino acids replaced in the protein by cysteines are selected from the group consisting of asparagine, leucine, or serine.

The terms "thiol side chain group," "thiol containing group," and "thiol side chain" are terms which are can be used interchangeably and include groups that are used to replace the thiol hydrogen of a cysteine used to replace one of the amino acids in a protein. Commonly, the thiol side chain group includes a sulfur through which the thiol side chain groups defined above are attached to the thiol sulfur of the cysteine.

The glycosylated thiosulfonates of the invention are those which are capable of reacting with a thiol hydrogen of a cysteine to produce a glycosylated amino acid residue. By glycosylated is meant that the thiosulfonate has bound thereto a sugar or carbohydrate moiety which can be transferred to a protein pursuant to the present invention. Preferably, the glycosylated thiosulfonates are glycosylated alkylthiosulfonates, most preferably, glycosylated methanethiosulfonates. Such glycosylated methanethiosulfonate have the general formula:

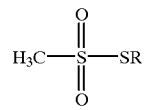

In particularly preferred embodiment, the methanethiosulfonate comprises an R group which comprises: -β-Glc, -Et-β-Gal, -Et-β-Glc, -Et-α-Glc, -Et-α-Man, -Et-Lac, -β-Glc(Ac)$_2$, -β-Glc(Ac)$_3$, -β-Glc(Ac)$_4$, -Et-α-Glc(Ac)$_2$, -Et-α-Glc(Ac)$_3$, -Et-α-Glc(Ac)$_4$, -Et-β-Glc(Ac)$_2$, -Et-β-Glc(Ac)$_3$, -Et-β-Glc(Ac)$_4$, -Et-α-Man(Ac)$_3$, -Et-α-Man(Ac)$_4$, -Et-β-Gal(Ac)$_3$, -Et-β-Gal(Ac)$_4$, -Et-Lac(Ac)$_5$, -Et-Lac(Ac)$_6$, or -Et-Lac(Ac)$_7$.

In a preferred embodiment, the carbohydrate moiety of the present invention is a dendrimer moiety. Multiple functionalization of chemically modified mutant proteins can be achieved by dendrimer approaches, whereby multiple-branched linking structures can be employed to create poly-functionalized chemically modified mutant proteins.

Highly branched molecules or dendrimers were first synthesized by Vögtle in 1978 (Buhleier et al., *Synthesis*, 155–158 (1978), which is hereby incorporated by reference). The attachment of identical building blocks that contain branching sites to a central core may be achieved with a high degree of homogeneity and control. Each branch contains a functional group which, after chemical alteration, may be connected to yet another branching building block. In this manner, layer after layer of branching rapidly generates highly-functionalized molecules.

For instance, multiple glycosylation, including multiple mannose-containing chemically modified mutant proteins, and varied sugar moieties, can be created. The dendrimer reagent structures would include methanethiosulfonates with simple branching such as:

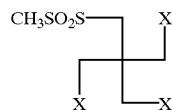

derived from pentaerythritol, to very complex branched dendrimer reagents (see FIG. 1).

Figure 2:
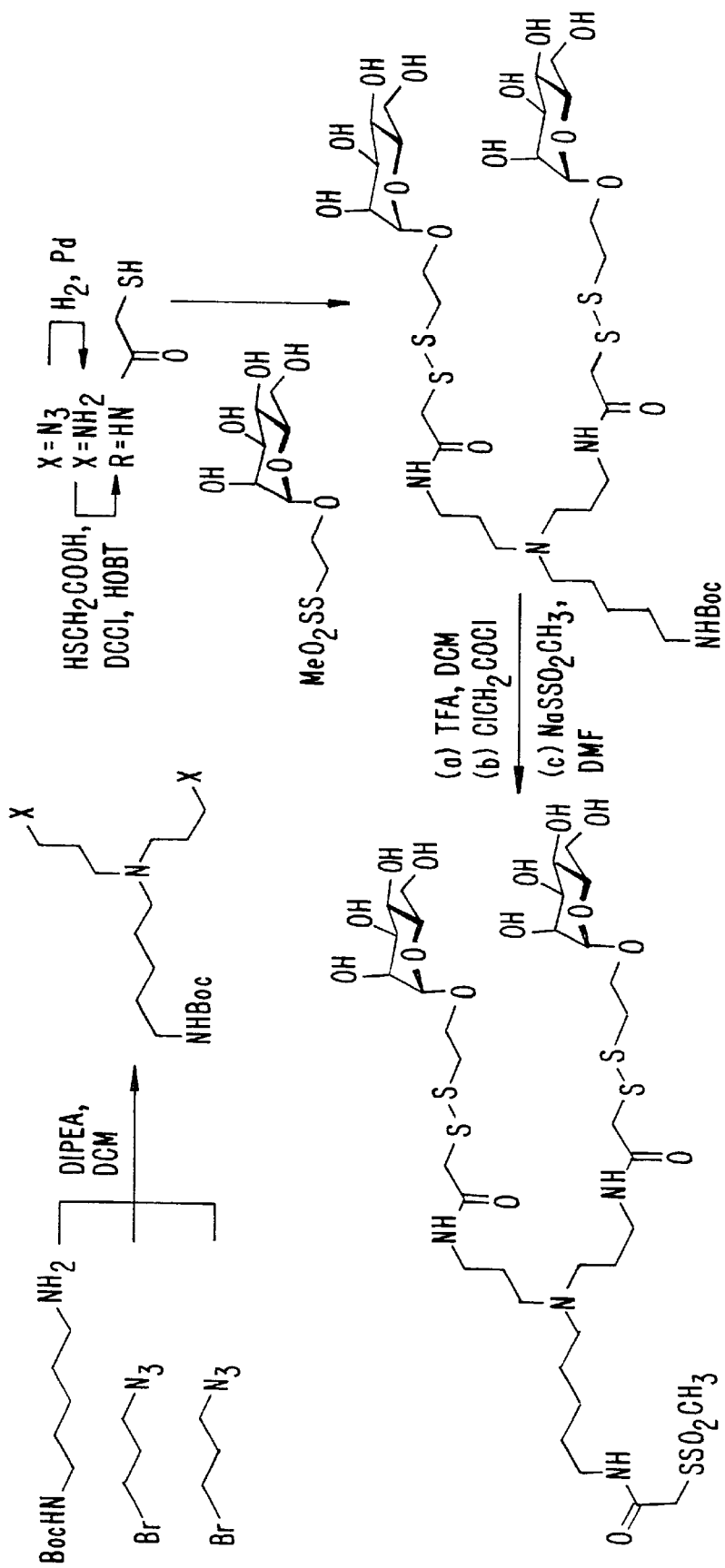
FIG. 2 shows the synthesis of a first generation glycodendrimer reagent which bears two D-mannose units on its termini and has one arm as a MTS which can be attached to a subtilisin *Bacillus lentus* cysteine mutant.
Figure 3:
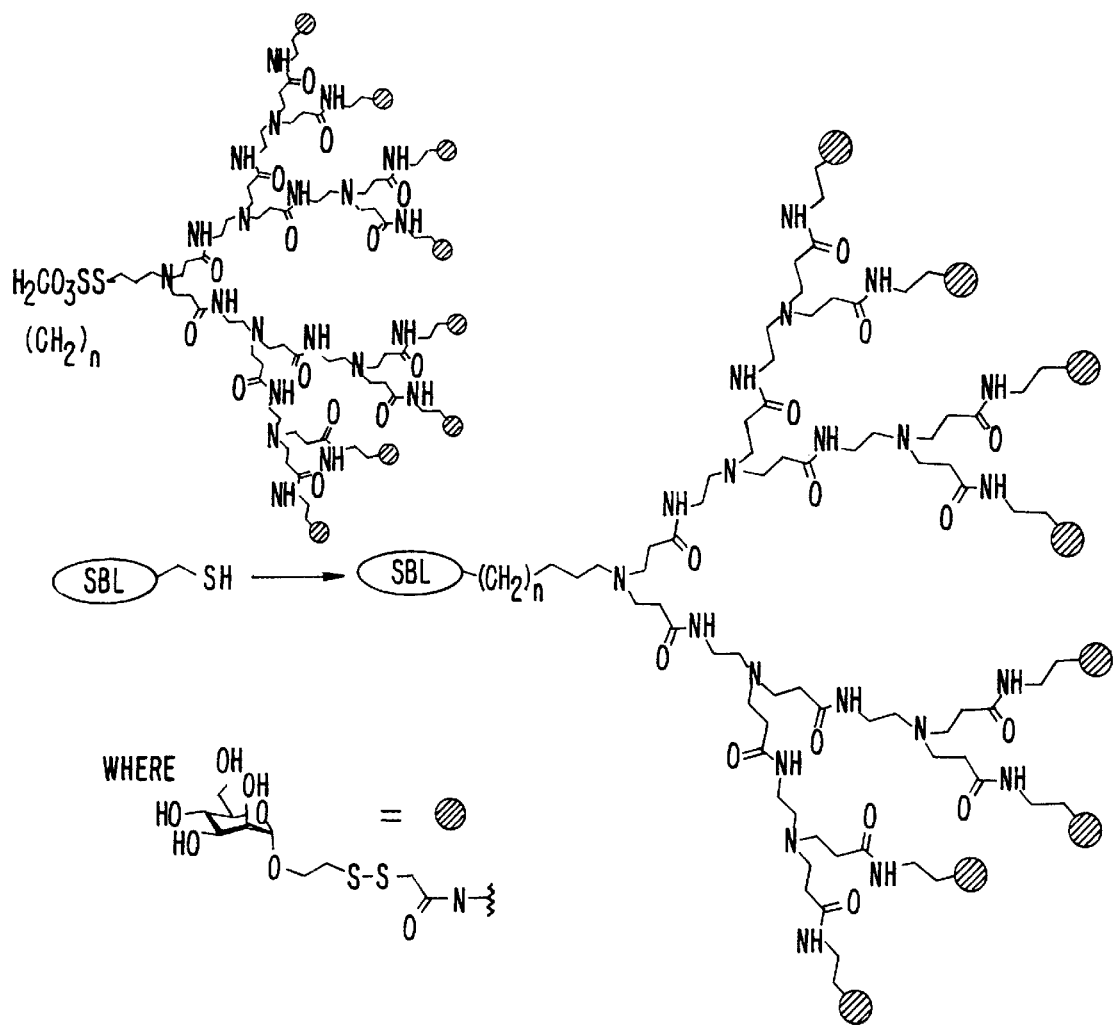
FIG. 3 shows the synthesis of highly-functionalized glycodendrimer-protein conjugates.

In particular, a first generation glycodendrimer reagent is synthesized as shown in FIG. 2. This approach can be extended to cover larger dendrimers. More specifically, by leaving one "arm" of the glycodendrimer free for conversion to a methanethiosulfonate, the remaining arms can be further branched to synthesize highly-functionalized glycodendrimer reagents as shown in FIG. 3. Through further branching and by using different carbohydrates, this concept can be extended to virtually unlimited levels.

Figure 4:
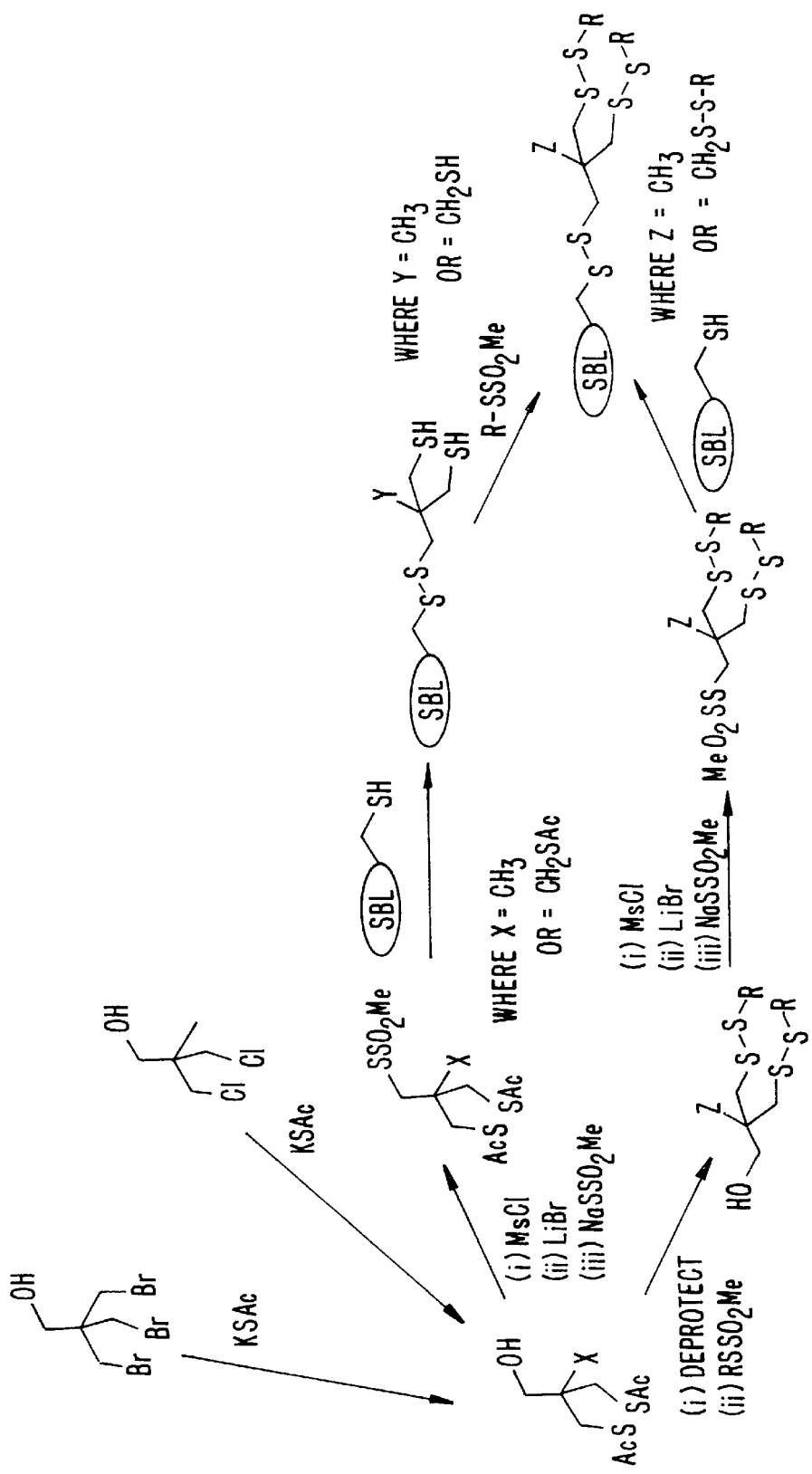
FIG. 4 shows two parallel synthetic approaches to modification of subtilisin *Bacillus lentus* with dendrimers. Both approaches allow the use of a large library of methanethiosulfonate reagents (R—$SSO_2$Me) to cap the dendrimeric branches. The routes shown allow for the preparation of both dimeric and trimeric dendrimers

A flexible synthetic strategy for the synthesis of core dendrimeric methanethiosulfonate building blocks that may be used either in situ or before modification to construct dendrimers is shown in FIG. 4.

The present invention also relates to glycosylated thiosulfonate compositions. Preferably the glycosylated thiosulfonates are methanethiosulfonates and comprise a chemical structure:

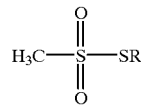

wherein R comprises -β-Glc, -Et-β-Gal, -Et-β-Glc, -Et-α-Glc, -Et-α-Man, -Et-Lac, -β-Glc(Ac)$_2$, -β-Glc(Ac)$_3$, -β-Glc(Ac)$_4$, -Et-α-Glc(Ac)$_2$, -Et-α-Glc(Ac)$_3$, -Et-α-Glc(Ac)$_4$, -Et-β-Glc(Ac)$_2$, -Et-β-Glc(Ac)$_3$, -Et-β-Glc(Ac)$_4$, -Et-α-Man (Ac)$_3$, -Et-α-Man(Ac)$_4$, -Et-β-Gal(Ac)$_3$, -Et-β-Gal(Ac)$_4$, -Et-Lac(Ac)$_5$, -Et-Lac(Ac)$_6$, or -Et-Lac(Ac)$_7$.

The present invention also relates to a method of determining the structure-function relationships of chemically modified mutant proteins. This method involves providing first and second chemically modified mutant proteins of the present invention, wherein the glycosylation pattern of the second chemically modified mutant protein is different from the glycosylation pattern of the first chemically modified mutant protein, evaluating a functional characteristic of the first and second chemically modified mutant proteins, and correlating the functional characteristic of the first and second chemically modified mutant proteins with the structures of the first and second chemically modified mutant proteins.

Evaluating a functional characteristic of the first and second chemically modified mutant protein includes testing for functional characteristics including, but not limited to, stability to temperature and reagents, solubility, partitioning, enzymatic activity, cell-cell signaling, substrate specificity, substrate binding, ability to mask an antigenic site, physiological functions, and pharmaceutical functions (Paulson, "Glycoproteins: What are the Sugar Chains For?", *Trends in Biochem. Sciences*, 14:272–276 (1989), which is hereby incorporated by reference).

Another aspect of the present invention is a second method of determining the structure-function relationships of chemically modified mutant proteins. This method involves providing first and second chemically modified mutant proteins of the present invention, wherein at least one different cysteine residue in the second chemically modified mutant protein is modified by reacting said cysteine residue with a glycosylated thiosulfonate, evaluating a functional characteristic of the first and second chemically modified mutant proteins, and correlating the functional characteristic of the first and second chemically modified mutant proteins with the structures of the first and second chemically modified mutant proteins.

Figure 5:
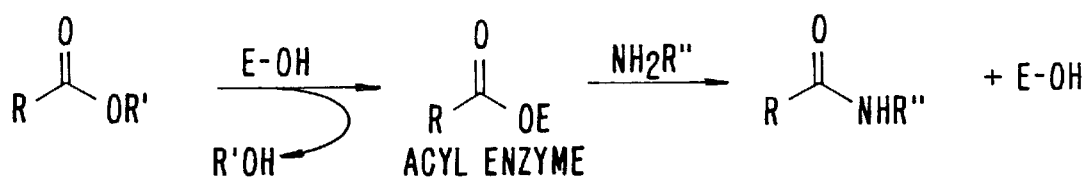
FIG. 5 shows peptide coupling catalyzed by an enzyme.

By way of example to illustrate some of its advantages, the following discussion will focus on certain proteases which are modified according to the methods of the present invention. Alkaline serine proteases (subtilisins) are finding increasing use in biocatalysis, particularly in chiral resolution, regioselective acylation of polyfunctional compounds, peptide coupling, and glycopeptide synthesis. As shown in FIG. 5, subtilisins can catalyze peptide bond formation starting from an ester substrate, by first forming an acyl enzyme intermediate which then reacts with a primary amine to form the peptide product. This application requires high esterase activity to promote acyl enzyme formation and low amidase activity to minimize hydrolysis of the peptide bond of the desired product. Generally, subtilisins do not meet these requirements. However, the improvement of the esterase to amidase selectivities of subtilisins has been a long sought after goal. By using the methods provided for in the present invention, it is possible to produce subtilisins which have advantageous properties.

The inventors in the present case used site specific mutagenesis to modify certain residues and introduce additional cysteine residues within subtilisin which would then serve to react with a glycosylated methanethiosulfonate to produce a glycosylation point at the introduced cysteine. *Bacillus lentus* subtilisin was selected for illustrative purposes because it does not contain a natural cysteine and is not naturally glycosylated.

The substrate binding site of an enzyme consists of a series of subsites across the surface of the enzyme. The portion of substrate that corresponds to the subsites are labeled P and the subsites are labeled S. By convention, the subsites are labeled $S_1$, $S_2$, $S_3$, $S_4$, $S_1'$, and $S_2'$. A discussion of subsites can be found in Berger et al., *Phil. Trans. Roy. Soc. Lond. B,* 257:249–264 (1970), Siezen et al., *Protein Engineering,* 4:719–737 (1991), and Fersht, *Enzyme Structure and Mechanism,* 2ed., Freeman: New York, 29–30 (1985), which are hereby incorporated by reference.

In the present illustration, the $S_1$, $S_1'$, or $S_2$ subsites were selected as suitable targets for modification. In particular, the amino acids corresponding to N62, L217, S156, and S166 in naturally-occurring subtilisin from *Bacillus amyloliquefaciens* or to equivalent amino acid residues in other subtilisins, such as *Bacillus lentus* subtilisin, were selected for modification to cysteine. The mutated subtilisin was produced through standard site directed mutagenesis techniques and the obtained mutant subtilisin was reacted with certain glycosylated alkylthiosulfonates, particularly glycosylated methanethiosulfonates, as provided in the examples appended hereto.

Enzymatic peptide coupling is an attractive method for preparation of a variety of peptides, because this method requires minimal protection of the substrate, proceeds under mild conditions, and does not cause racemization. Wong et al., *Enzymes in Synthetic Organic Chemistry,* Pergamon Press: Oxford, 41–130 (1994), which is hereby incorporated by reference. In spite of these advantages, two major problems have limited the use of serine proteases in peptide synthesis. One is their efficient proteolytic (amidase) activity which causes hydrolysis of the coupling product, and the other is their stringent structural specificity and stereospecificity.

Surprisingly, it was found that the chemically modified mutant subtilisins of the present invention have altered esterase-to-amidase activity as compared to the precursor enzyme. Increasing the esterase-to-amidase ratio enables the use of the enzyme to more efficiently catalyze peptide synthesis. In particular, subtilisins can catalyze peptide bond formation starting from an ester substrate (i.e. an acyl donor), by first forming an acyl enzyme intermediate which then reacts with a primary amine (i.e. an acyl acceptor) to form the peptide product, as shown in FIG. 5. This reaction thus requires high esterase activity to promote acyl enzyme formation and, then, low amidase activity to minimize hydrolysis of the peptide bond of the desired product. The chemically modified mutant subtilisins produced according to the present invention show an increased esterase-to-amidase ratio, without reducing the absolute esterase activity of the enzyme. In addition, certain modified enzymes of the present invention even show a concomitant increase in the absolute esterase activity.

Therefore, an unexpected benefit of subtilisins which are modified according to the present invention is that they can be used in organic synthesis to, for example, catalyze a desired reaction and/or favor a certain stereoselectivity. See e.g., Noritomi et al. *Biotech. Bioeng.* 51:95–99 (1996); Dabulis et al. *Biotech. Bioeng.* 41:566–571 (1993), and Fitzpatrick et al. *J. Am. Chem. Soc.* 113:3166–3171 (1991), which are hereby incorporated by reference.

Proteins obtained using the methods provided herein may be used in any application in which it is desired to use such proteins, where having modified functional capabilities is advantageous. Thus, proteins modified as provided herein may be used in the medical field for pharmaceutical compositions and in diagnostic preparations. Additionally, proteins such as enzymes which are modified according to the present invention may be used in applications which are generally known for such enzymes including industrial applications such as cleaning products, textile processing, feed modification, food modification, brewing of grain beverages, starch processing, as antimicrobials, and in personal care formulations. Moreover, the unique functionalities made possible by the present invention may result in uses for proteins which have not heretofore been recognized as feasible.

EXAMPLES

Example 1
Preparation of Methanethiosulfonate ("MTS") Reagents

The preparation of $NaSSO_2CH_3$ (Kenyon et al., *Methods Enzymol.,* 47:407–430 (1977), which is hereby incorporated by reference) has been described previously (Berglund et al., *J. Am. Chem. Soc.,* 119:5265–5266 (1997), which is hereby incorporated by reference). Acetobromoglucose (3) (See FIG. 6) (prepared from D-glucose according to Scheurer et al., *J. Am. Chem. Soc.,* 76:3224 (1954), which is hereby incorporated by reference) in 73% yield, pentaacetylglucose (prepared from the corresponding parent carbohydrates according to the method of Verley et al., *Ber. Dtsch. Chem. Ges.,* 34:3354–3358 (1901), which is hereby incorporated by reference, and purified by flash chromatography) in 99% yield, 5d (See FIG. 7) (prepared from the corresponding parent carbohydrates according to the method of Verley et al., *Ber. Dtsch. Chem. Ges.,* 34:3354–3358 (1901), which is hereby incorporated by reference, and purified by flash chromatography) in 92% yield, 5e (See FIG. 7) (prepared from the corresponding parent carbohydrates according to the method of Verley et al., *Ber. Dtsch. Chem. Ges.,* 34:3354–3358 (1901), which is hereby incorporated by reference, and purified by flash chromatography) in 99% yield, 5f (See FIG. 7) (prepared from lactose according to the method of Hudson et al., *J. Am. Chem. Soc.,* 37:1270–1275 (1915), which is hereby incorporated by reference, and purified by flash chromatography in 82% yield) were prepared according to literature methods. N,N-dimethylformamide ("DMF") was distilled under $N_2$ from $CaH_2$ and stored over molecular sieve under $N_2$ before use. Methanol was distilled from $Mg/I_2$ under $N_2$ immediately prior to use. $Br(CH_2)_2OH$ was stood over and distilled from CaO under reduced pressure and stored under $N_2$ prior to use. All other chemicals were used as received from Sigma-Aldrich (St. Louis, Mo.) or Baker (Phillipsburg, N.J.). All flash chromatography was performed using silica gel (Whatman, 60 Å, 230–400 Mesh, Clifton, N.J.). Melting points were determined using an Electrothermal IA9000 series digital melting point apparatus and are uncorrected. IR spectra were recorded on Bomem MB or Perkin-Elmer FTIR Spectrum 1000 spectrophotometers. $^1H$ NMR and $^{13}C$ NMR spectra were recorded on Varian Gemini 200, Unity 400 or Unity 500 NMR spectrometers at the frequencies indicated. Where indicated, NMR peak assignments were made using Correlation Spectroscopy ("COSY") or Distortionless Enhanced by Polarization Transfer ("DEPT") experiments, all others are subjective. All chemical shifts were referenced to residual solvent as an internal standard; for $^{13}C$ NMR in $D_2O$ 1,4-dioxan (67.6 ppm) was used. ES-MS data were acquired using a PE SCIEX API III Biomolecular mass spectrometer. All HRMS data were acquired using Micromass 70–250S or Micromass ZAB-SE mass spectrometers according to the ionization methods indicated. Solvents were removed in vacuo.

Preparation of 2,3,4,6-Tetra-O-aceryl-β-D-glucopyranosyl methanethiosulfonate (1a).

Initial approaches to untethered glyco-MTS reagents similar in type to 1a (See FIG. 8) were based upon Danishefsky's glycal methodology (Halcomb et al., *J. Am. Chem. Soc.*, 111:6661–6666 (1989), which is hereby incorporated by reference). Tris—TBS glucal was prepared according to the method of Lesimple et al., *Tetrahedron Lett.*, 27:6201–6204 (1986), which is hereby incorporated by reference, and oxidized to tris—TBS protected 1,2-anhydroglucose using dimethyldioxirane. However, under a variety of conditions and in contrast to the behavior of other sulfur nucleophiles (Gordon et al., *Carbohydr. Res.*, 206:361–366 (1990); Berkowitz et al, *J. Am. Chem. Soc.*, 114:4518–4529 (1992), which are hereby incorporated by reference), methanethiosulfonate ion failed to open the epoxide moiety of tris—TBS protected 1,2-anhydro-D-glucose. Deprotection of 1a (See FIG. 8) was attempted under a variety of conditions, but in all cases led only to decomposition or hydrolysis of the thioglucosidic bond (Zemplén et al., *Ber. Dtsch. Chem. Ges.*, 56:1705–1710 (1923); Plattner et al., *J. Am. Chem. Soc.*, 94:8613–8615 (1972); Mori et al., *Tetrahedron Lett.*, 20:1329–1332 (1979); Herzig et al., *Carbohydr. Res.*, 153:162–167 (1986); Herzig et al., *J. Org. Chem.*, 51:727–730 (1986); Vekemans et al., *Tetrahedron Lett.*, 28:2299–2300 (1987); Cinget et al., *Synlett*, 168–170 (1993), which are hereby incorporated by reference).

Acetobromoglucose (3) (See FIG. 6) (1 g, 2.43 mmol) was added to a solution of $NaSSO_2CH_3$ (380 mg, 2.84 mmol) in ethanol (4 mL) at 90° C. under $N_2$. After 20 minutes the resulting suspension was cooled and the solvent removed. The residue was purified by flash chromatography (EtOAc:hexane, 9:11) and the resulting solid recrystallized from ether to give 1a (See FIG. 8) (674 mg, 63%) as a white solid; mp 151–152° C. melts then decomp. (ether); $[\alpha]^{27}_D$=−19.0 (c 1.24, $CHCl_3$); IR (KBr) 1749 $cm^{-1}$ (C=O), 1333, 1140 $cm^{-1}$ (S—$SO_2$); $^1H$ NMR (400 MHz, $CDCl_3$) δ 2.00, 2.04, 2.06, 2.07 (s×4, 3H×4, Ac×4), 3.44 (s, 3H, $CH_3SO_2$—), 3.82 (ddd, $J_{4,5}$ 10.1 Hz, $J_{5,6}$ 5.9 Hz, $J_{5,6'}$ 2.2 Hz, 1H, H-5), 4.08 (dd, $J_{5,6}$ 5.9 Hz, $J_{6,6'}$ 12.5 Hz, 1H, H-6),4.31 (dd, $J_{5,6}$ 2.2 Hz, $J_{6,6}$ 12.5 Hz, 1H, H-6'), 5.05 (t, J9.8 Hz, 1H, H-4), 5.07 (dd, $J_{1,2}$ 10.5 Hz, $J_{2,3}$ 9.4 Hz, 1H, H-2), 5.25 (d, $J_{1,2}$ 10.5 Hz, 1H, H-1), 5.29 (t, J9.3 Hz, 1H, H-3); $^{13}C$ NMR (50 MHz, $CDCl_3$) δ 20.5, 20.7 ($CH_3COO$—×4), 52.8 ($CH_3SO_2$—), 61.8, 68.0, 68.7, 73.3, 76.6 (C-2, C-3, C-4, C-5, C-6), 86.4 (C-1), 169.3, 169.3, 169.7, 170.1 ($CH_3COO$—×4); HRMS m/z (EI+):

Found 443.0636 (M+H⁻); $C_{15}H_{23}O_{11}S_2$ requires 443.0682.

Preparation of 2-(2,3,4,6-Tetra-O-acetyl-α-D-glucopyranosyl)ethyl methanethiosulfonate (1g).

$BF_3.Et_2O$ (145 μL, 1.1 mmol) was added dropwise to a suspension of D-glucose (2a) (See FIG. 6) (1.45 g, 8.1 mmol) in $Br(CH_2)_2OH$ (19 mL) under $N_2$ and the resulting mixture heated to 105° C. After 8 hours, the resulting solution was cooled and the solvent removed. The residue was dissolved in $Ac_2O$/pyridine (2:3 v/v, 16 mL) under $N_2$. After a further 24 hours, the reaction solvent was removed and the residue purified by repeated flash chromatography (EtOAc then EtOAc:hexane, 3:7) to give 2-bromoethyl 2,3,4,6-tetra-O-acetyl-α-D-glucopyranoside (4g) (See FIG. 6) (1.76 g, 48%) as a colorless oil that crystallized on standing to give a white solid; mp 86–88° C.; $[\alpha]^{25}_D$=+130.6 (c 0.21, $CHCl_3$); IR (film) 1749 $cm^{-1}$ (C=O); $^1H$ NMR (400 MHz, $CDCl_3$) δ 2.01, 2.03, 2.07, 2.09 (s×4, 3H×4, Ac×4), 3.51 (t, J5.9 Hz, 2H, —$CH_2Br$), 3.83 (dt, $J_d$ 11.6 Hz, $J_t$ 5.8 Hz, 1H, —OCHH'—), 3.96 (dt, $J_d$ 11.6 Hz, $J_t$ 5.8 Hz, 1H, —OCHH'—), 4.10 (dd, $J_{5,6}$ 2.2 Hz, $J_{6,6'}$ 12.0 Hz, 1H, H-6),4.14 (ddd, $J_{4,5}$ 10.2 Hz, $J_{5,6}$ 2.2 Hz, $J_{5,6'}$ 4.4 Hz, 1H, H-5), 4.24 (dd, $J_{5,6'}$ 4.4 Hz, $J_{6,6'}$ 12.0 Hz, 1H, H-6'), 4.84 (dd, $J_{1,2}$ 3.8 Hz, $J_{2,3}$ 10.3 Hz, 1H, H-2), 5.05 (t, J9.7 Hz, 1H, H-4), 5.14 (d, $J_{1,2}$ 3.8 Hz, 1H, H-1), 5.49 (dd, $J_{2,3}$ 10.3 Hz, $J_{3,4}$ 9.5 Hz, 1H, H-3); $^{13}C$ NMR (100 MHz, $CDCl_3$) δ 20.6, 20.7 ($CH_3COO$—×4), 29.9 (—$CH_2Br$), 61.9, 67.8, 68.5, 68.8, 70.0, 70.8 (—$OCH_2$—, C-2, C-3, C-4, C-5, C-6), 96.0 (C-1), 169.6, 170.0, 170.2, 170.6 ($CH_3COO$—×4); HRMS m/z (FAB+): Found 477.0381 (M+Na⁻); $C_{16}H_{23}O_{10}BrNa$ requires 477.0372. $NaSSO_2CH_3$ (75 mg, 0.56 mmol) was added to a solution of 4g (See FIG. 6) (190 mg, 0.42 mmol) in DMF (6 mL) under $N_2$ and warmed to 50° C. After 21 hours, the solution was cooled and the solvent removed. The residue was purified by flash chromatography (EtOAc:hexane, 1:1) to give 1g (See FIG. 6) (183 mg, 90%) as a colorless oil; $[\alpha]^{27}_D$=+92.1 (c 0.39, $CHCl_3$); IR (film) 1748 $cm^{-1}$ (C=O), 1322, 1134 $cm^{-1}$ (S—$SO_2$); $^1H$ NMR (400 MHz, $CDCl_3$) 6 2.01, 2.03, 2.07, 2.09 (s×4, 3H×4, Ac×4), 3.41 (t, J5.7 Hz, 2H, —$CH_2S$—), 3.41 (s, 3H, $CH_3SO_2$—), 3.75 (dt, $J_d$ 10.8 Hz, J, 5.7 Hz, 1H, —OCHH'—), 3.99–4.06 (m, 2H, H-5, —OCHH'—), 4.09 (dd, $J_{5,6}$ 2.4 Hz, $J_{6,6'}$ 12.6 Hz, 1H, H-6), 4.25 (dd, $J_{5,6'}$ 4.6 Hz, $J_{6,6'}$ 12.6 Hz, 1H, H-6'), 4.87 (dd, $J_{1,2}$ 3.9 Hz, $J_{2,3}$ 10.3 Hz, 1H, H-2), 5.06 (t, J9.8 Hz, 1H, H-4), 5.12 (d, $J_{1,2}$ 3.9 Hz, 1H, H-1), 5.43 (t, J9.8 Hz, 1H, H-3); $^{13}C$ NMR (100 MHz, $CDCl_3$) δ 20.6, 20.6, 20.7, 20.7 ($CH_3COO$—×4), 36.0, (—$CH_2S$—), 50.8 ($CH_3SO_2$—), 61.8 (—$OCH_2$—), 67.0, 67.8, 68.3, 69.8, 70.7 (C-2, C-3, C-4, C-5, C-6), 96.0 (C-1), 169.5, 170.0, 170.6 ($CH_3COO$—×4); HRMS m/z (FAB+): Found 487.0946 (M+H⁺); $C_{17}H_{27}O_{12}S_2$ requires 487.0944.

Preparation of 2-(α-D-Glucopyranosyl)ethyl methanethiosulfonate (1b).

A solution of NaOMe (0.1 M, 0.3 mL) was added to a suspension of 4g (See FIG. 6) (300 mg, 0.66 mmol) in MeOH (3 mL) under $N_2$ and stirred vigorously. After 6 hours, the resulting solution was passed through a Dowex 50W(H⁺) plug (2×1 cm, eluant MeOH) and the solvent removed to give 2-bromoethyl α-D-glucopyranoside bromide (4b) (See FIG. 6) (178 mg, 94%) (The synthesis of 4b as an intermediate has been described previously. However, this method gave only a poor yield of product. Nagai et al., *Carbohydr. Res.*, 190:165–180 (1989), which is hereby incorporated by reference) as a white solid. $NaSSO_2CH_3$ (100 mg, 0.75 mmol) was added to a solution of 4b (See FIG. 6) (178 mg, 0.62 mmol) in DMF (7 mL) under $N_2$ and warmed to 50° C. After 25 hours, the solution was cooled and the solvent removed. The residue was purified by flash chromatography (MeOH:EtOAc, 1:9) to give 1b (See FIG. 6) (144 mg, 73%) as a hygroscopic foam; $[\alpha]^{27}_D$=+109.9 (c 1.11, $H_2O$); IR (film) 3423 $cm^{-1}$ (OH), 1309, 1128 $cm^{-1}$ (S—$SO_2$); $^1H$ NMR (500 MHz, $D_2O$, COSY) δ 3.16 (t, J9.5 Hz, 1H, H-4), 3.28 (t, J5.9 Hz, 2H, —$CH_2S$—), 3.30 (s, 3H, $CH_3SO_2$—), 3.31 (dd, $J_{1,2}$ 3.8 Hz, $J_{2,3}$ 9.9 Hz, 1H, H-2), 3.44 (t, J9.5 Hz, 1H, H-3), 3.47–3.53 (m, 2H, H-6, H-6'), 3.58–3.61 (m, 1H, H-5), 3.62 (dt, $J_t$ 5.4 Hz, $J_d$ 10.8 Hz, 1H, —OCHH'—), 3.79 (dt, $J_t$ 6.3 Hz, $J_d$ 10.8 Hz, 1H, —OCHH'), 4.72 (d, $J_{1,2}$ 3.8 Hz, 1H, H-1); $^{13}C$ NMR (100 MHz, $D_2O$) δ 36.7 (—$CH_2S$—), 50.7 ($CH_3SO_2$—), 61.5 (—$OCH_2$—), 67.2, 70.5, 72.3, 73.2, 74.0 (C-2, C-3, C-4, C-5, C-6), 99.4 (C-1); HRMS m/z (FAB+): Found 319.0517 (M+H$^+$); $C_9H_{19}O_8S_2$ requires 319.0521.

Preparation of 2-(2,3,4,6-Tetra-O-acetyl-β-D-glucopyranosyl)ethyl methanethiosulfonate (1h).

$BF_3.Et_2O$ (3.3 mL, 26.0 mmol) was added dropwise over the course of 15 minutes to a solution of 1,2,3,4,6-penta-O-acetyl-α,β-D-glucose (2 g, 5.1 mmol) and $Br(CH_2)_2OH$ (0.45 mL, 6.3 mmol) in $CH_2Cl_2$ (9 mL) at 0° C. under $N_2$. After 1.5 hours, the solution was warmed to room temperature. After 20 hours the reaction solution was added to ice water (15 mL) and extracted with $CH_2Cl_2$ (15 mL×3). These extracts were combined, washed with water (15 mL), sat. $NaHCO_3$ (aq., 15 mL), water (15 mL), dried ($MgSO_4$), filtered, and the solvent removed. The residue was purified by flash chromatography (EtOAc:hexane, 1:3) to give 2-bromoethyl 2,3,4,6-tetra-O-acetyl-β-D-glucopyranoside (4h) (See FIG. 6) (1.42 g, 61%) as a white solid; mp 118–120° C. (EtOAc/iso-octane) [lit., (Coles et al., *J. Am. Chem. Soc.*, 60:1020–1022 (1938), which is hereby incorporated by reference) mp 117.3° C. (EtOH)]; $[\alpha]^{27}_D$=−11.9 (c 1.65, $CHCl_3$) [lit., (Helferich et al., *Just. Lieb. Ann. Chem.*, 541:1–16 (1939), which is hereby incorporated by reference) $[\alpha]^{20}_D$=−12.3 (c 0.2, $CHCl_3$)]; $^1$H NMR (200 MHz, $CDCl_3$) δ 2.00, 2.02, 2.07, 2.09 (s×4, 3H×4, Ac×4), 3.42–3.51 (m, 2H), 3.67–3.87 (m, 2H), 4.10–4.31 (m, 3H), 4.57 (d, $J_{1,2}$ 8 Hz, 1H, H-1), 4.97–5.27 (m, 3H). $NaSSO_2CH_3$ (260 mg, 1.94 mmol) was added to a solution of 4h (See FIG. 6) (640 mg, 1.41 mmol) in DMF (18 mL) under $N_2$ and warmed to 50° C. After 25 hours, the solution was cooled and the solvent removed. The residue was purified by flash chromatography (EtOAc:hexane, 1:1) and the resulting solid recrystallized from EtOAc/hexane to give 1h (See FIG. 6) (544 mg, 80%) as a white solid; mp 115–116° C. (EtOAc/hexane); $[\alpha]^{27}_D$=+5.4 (c 1.06, $CHCl_3$); IR (KBr) 1758, 1741 cm$^{-1}$ (C=O), 1314, 1133 cm$^{-1}$ (S—SO,); $^1$H NMR (500 MHz, $CDCl_3$, COSY) δ 1.99, 2.02, 2.06, 2.08 (s×4, 3H×4, Ac×4), 3.30–3.38 (m, 2H, —CH$_2$S—), 3.34 (s, 3H, CH$_3$SO$_2$—), 3.70 (ddd, $J_{4,5}$ 9.9 Hz, $J_{5,6}$ 2.2 Hz, $J_{5,6'}$ 4.6 Hz, 1H. H-5), 3.83 (ddd, J 5.6 Hz, J 7.4 Hz, J 10.5 Hz, 1H, —OCHH'—), 4.13–4.18 (m, 2H, H-6, —OCHH'—), 4.24 (dd, $J_{5,6'}$ 4.6 Hz, $J_{6,6'}$ 12.4 Hz, 1H, H-6'), 4.55 (d, $J_{1,2}$ 8.1 Hz, 1H, H-1), 4.98 (dd,$J_{1,2}$ 8.1 Hz, $J_{2,3}$ 9.7 Hz, 1H, H-2), 5.07 (t, J 9.9 Hz, 1 H, H-4), 5.19 (t, J 9.6 Hz, 1H, H-3); $^{13}$C NMR (125 MHz, $CDCl_3$, DEPT) δ 20.5, 20.7 (q×2, CH$_3$COO—×4), 36.0, (t, —CH$_2$S—), 50.6 (q, CH$_3$SO$_2$—), 61.6 (t, —OCH$_2$—), 68.1, 70.8, 71.9, 72.5 (d×4, C-2, C-3, C-4, C-5), 68.4 (t, C-6), 100.8 (d, C-1), 169.3, 170.0, 170.5 (s×3 CH$_3$COO—×4); HRMS m/z (FAB+): Found 487.0940 (M+H$^+$); $C_{17}H_{27}O_{12}S_2$ requires 487.0944.

Preparation of 2-(β-D-Glucopyranosyl)ethyl methanethiosulfonate (1c).

A solution of NaOMe (0.1M, 0.3 mL) was added to a suspension of 4h (See FIG. 6) (300 mg, 0.66 mmol) in MeOH (3 mL) under $N_2$ and stirred vigorously. After 4 hours, the resulting solution was passed through a Dowex 50W(H$^+$) plug (2×1 cm, eluant MeOH) and the solvent removed to give 2-bromoethyl β-D-glucopyranoside 4c (See FIG. 6) (176 mg, 93%) as a white solid that was used directly in the next step. A sample was recrystallized from EtOH/EtOAc to give a colorless, crystalline solid; mp 74–78° C. (EtOH/EtOAc) [lit., (Helferich et al., *Just. Lieb. Ann. Chem.*, 541:1–16 (1939), which is hereby incorporated by reference) mp 74–75° C. (EtOH/EtOAc)]; $[\alpha]^{26}_D$=−22.4 (c 1.63, $H_2O$) [lit., (Helferich et al., *Just. Lieb. Ann. Chem.*, 541:1–16 (1939), which is hereby incorporated by reference) $[\alpha]^{19}_D$=−26.1 (c 3.0, $H_2O$)]; $^1$H NMR (400 MHz, $CD_3OD$) δ 3.30 (t, J 8.4 Hz, 1H, H-2), 3.39–3.49 (m, 3H), 3.64–3.80 (m, 31H), 3.97 (br d, $J_{6,6'}$ 11.7 Hz, 1H, H-6'), 4.02 (dt, $J_t$ 6.5 Hz, $J_d$ 11.3 Hz, 1H, —OCHH'—), 4.23 (dt, $J_t$ 6.5 Hz, $J_d$ 11.3 Hz, 1H, —OCHH'—), 4.44 (d, $J_{1,2}$ 7.9 Hz, 1H, H-1). $NaSSO_2CH_3$ (100 mg, 0.75 mmol) was added to a solution of 4c (See FIG. 6) (176 mg, 0.61 mmol) in DMF (7 mL) under $N_2$ and warmed to 50° C. After 15 hours, the solution was cooled and the solvent removed. The residue was purified by flash chromatography (MeOH:EtOAc, 1:9) to give 1c (See FIG. 6) (144 mg, 74%) as a hygroscopic foam; $[\alpha]^{27}_D$=−15.8 (c 0.88, $H_2O$); IR(KBr) 3400 cm$^{-1}$ (OH), 1310, 1131 cm$^{-1}$ (S—SO$_2$); $^1$H NMR (500 MHz, $D_2O$, COSY) δ 3.07 (dd, $J_{1,2}$ 8.1 Hz, $J_{2,3}$ 9.4 Hz, 1H, H-2), 3.16 (dd, $J_{3,4}$ 9.0 Hz $J_{4,5}$ 9.8Hz, 1H, H-4), 3.24 (ddd, $J_{4,5}$ 9.8 Hz, $J_{5,6}$ 6.0 Hz, $J_{5,6'}$ 2.3Hz, 1H, H-5), 3.27 (t, J 9.0 Hz, 1H, H-3), 3.30–3.33 (m, 2H, —CH$_2$S—), 3.34 (s, 3H, CH$_3$SO$_2$—), 3.50 (dd, $J_{5,6}$ 6.0 Hz, $J_{6,6'}$ 12.4 Hz, 1H, H-6), 3.69 (dd, $J_{5,6}$ 2.3 Hz, $J_{6,6'}$ 12.4 Hz, 1H, H-6'), 3.81 (dt, $J_t$ 5.8 Hz, $J_d$ 11.5 Hz, 1H, —OCHH'—), 4.00 (dt, $J_t$ 5.7 Hz, $J_d$ 11.4 Hz, 1H, —OCHH'—), 4.30 (d, $J_{1,2}$ 8.1 Hz, 1H, H-1); $^{13}$C NMR (50 MHz, $D_2O$) δ 36.9 (—CH$_2$S—), 51.0 (CH$_3$SO$_2$—), 62.0 (—OCH$_2$—), 69.5, 70.9, 74.3, 76.7, 77.3 (C-2, C-3, C-4, C-5, C-6), 103.7 (C-1); HRMS m/z (FAB+): Found 341.0351 (M+Na$^+$); $C_9H_{18}O_8S_2Na$ requires 341.0341.

Preparation of 2-(2,3,4,6-Tetra-O-acetyl-α-D-mannopyranosyl)ethyl methanethiosuifonate (1i).

$BF_3.Et_2O$ (7.7 mL, 60.7 mmol) was added dropwise over the course of 15 minutes to a solution of 1,2,3,4,6-penta-O-acetyl-α,β-D-mannose (5d) (See FIG. 7) (4.7 g, 12.1 mmol) and $Br(CH_2)_2OH$ (1.05 mL, 14.8 mmol) in $CH_2Cl_2$ (22 mL) at 0° C. under $N_2$. After 1 hour, the solution was warmed to room temperature. After 25 hours, the reaction solution was added to ice water (20 mL) and extracted with $CH_2Cl_2$ (20 mL×2). These extracts were combined, washed with water (20 mL), sat. $NaHCO_3$ (aq., 20 mL), water (20 mL), dried ($MgSO_4$), filtered, and the solvent removed. The residue was crystallized from EtOAc/iso-octane to give 2-bromoethyl 2,3,4,6-tetra-O-acetyl-α-D-mannopyranoside (4i) (See FIG. 7) (3.52 g, 64%). Purification of the resulting mother liquor by flash chromatography (EtOAc:hexane, 1:3) gave further 4i (See FIG. 7) (320 mg, 6%; 70% in total) as a white highly crystalline solid; mp 121–123° C. [lit., (Dahmén et al., "2-Bromoethyl Glycosides—Synthesis and Characterization," *Carbohydr. Res.*, 116:303–307 (1983), which is hereby incorporated by reference) 118–119° C. (EtOAc/iso-octane)]; $[\alpha]^{28}_D$=+48.3 (c 1.31, $CHCl_3$) [lit., (Dahmén et al., "2-Bromoethyl Glycosides—Synthesis and Characterization," *Carbohydr. Res.*, 116:303–307 (1983), which is hereby incorporated by reference) $[\alpha]^{23}_D$=+45 (c 0.6, $CDCl_3$)]; $^1$H NMR (200 MHz, $CDCl_3$) δ 1.99, 2.05, 2.10, 2.16 (s×4, 3H×4, Ac×4), 3.52 (t, J6 Hz, 2H, —CH$_2$Br), 3.82–4.04 (m, 2H, —OCH$_2$—), 4.09–4.16 (m, 1H, H-5), 4.13 (dd, $J_{5,6}$ 2 Hz, $J_{6,6'}$ 12 Hz, 1H, H-6) 4.28 (dd, $J_{5,6'}$ 6 Hz, $J_{6,6'}$ 12 Hz, 1H, H-6'), 4.87 (br s, 1H, H-1), 5.22–5.40 (m, 3H, H-2, H-3, H-4). $NaSSO_2CH_3$ (230 mg, 1.72 mmol) was added to a solution of 4i (See FIG. 7) (600 mg, 1.32 mmol) in DMF (17 mL) under $N_2$ and warmed to 55° C. After 20 hours, the solution was cooled and the solvent removed. The residue was purified by flash chromatography (EtOAc:hexane, 9:11) and the resulting solid recrystallized from $Et_2O$/hexane to give 1i (See FIG. 7) (566 mg, 88%) as a white solid; mp 128–129° C. ($Et_2O$/hexane); $[\alpha]^{27}_D$=+53.2 (c 0.92, $CHCl_3$); IR (KBr) 1739 cm$^{-1}$ (C=O), 1325, 1129 cm$^{-1}$ (S—SO$_2$); $^1$H NMR (500 MHz, $CDCl_3$, COSY) δ 1.97, 2.04, 2.09, 2.14 (s×4, 3H×4, Ac×4), 3.37–3.40 (m, 2H, —CH$_2$S—), 3.38 (s, 3H, CH$_3$SO$_2$—), 3.79 (dt, J$_d$ 10.5 Hz, J$_t$ 5.8 Hz, 1H, —OCHH'—), 3.98–4.03 (m, 2H, —OCHH'—, H-5), 4.09 (dd, J$_{5,6}$ 2.5 Hz, J$_{6,6'}$ 12.5 Hz, 1H, H-6), 4.26 (dd, J$_{5,6'}$ 5.6 Hz, J$_{6,6'}$ 12.5 Hz, 1H, H-6'), 4.85 (d, J$_{1,2}$ 0.7 Hz, 1H, H-1), 5.23–5.29 (m, 3H, H-2, H-3, H-4); $^{13}$C NMR (50 MHz, CDCl$_3$) δ 20.6, 20.7, 20.8 (CH$_3$COO—×4), 35.7, (—CH$_2$S—),50.8 (CH$_3$SO$_2$—), 62.5 (—OCH$_2$—), 66.0, 66.8, 69.0, 69.2, 69.3 (C-2, C-3, C-4, C-5, C-6), 97.7 (C-1), 169.7, 169.9, 170.0, 170.6 (CH$_3$COO—×4); HRMS m/z (FAB+): Found 487.0954 (M+H$^-$); C$_{17}$H$_{27}$O$_{12}$S$_2$ requires 487.0944.

Preparation of 2-(α-D-Mannopyranosyl)ethyl methanethiosulfonate (1d).

A solution of NaOMe (0.143 M, 0.7 mL) was added to a suspension of 4i (See FIG. 7) (1 g, 2.2 mmol) in MeOH (10 mL) under N$_2$. After 3 hours, the resulting solution was passed through a Dowex 50W(H$^+$) plug (2×1 cm, eluant MeOH) and the solvent removed. The residue was purified by flash chromatography (MeOH:EtOAc, 2:25) to give 2-bromoethyl α-D-mannopyranoside 4d (See FIG. 7) (The use of 4d as a reactant has been described previously, although no details of preparation or characterization were given. (U.S. Pat. No. 4,918,009 to Nilsson, which is hereby incorporated by reference)) (606 mg, 96%) as a white foam; [α]$^{26}_D$=+50.7 (c 0.91, H$_2$O); IR (KBr) 3417 cm$^{-1}$ (OH); $^1$H NMR (500 MHz, D$_2$O, COSY) δ 3.38–3.44 (m, 3H, H-4, —CH$_2$Br), 3.50–3.55 (m, 2H, H-5, H-6), 3.60 (dd, J$_{2,3}$ 3.5 Hz, J$_{3,4}$ 9.7 Hz, 1H, H-3), 3.66 (dd, J$_{5,6'}$ 4.6 Hz, J$_{6,6'}$ 11.2 Hz, 1H, H-6'), 3.68 (ddd, J4.6 Hz, J5.4 Hz ,J 11.7 Hz, 1H, —OCHH'—), 3.76 (dd, J$_{1,2}$ 1.8 Hz, J$_{2,3}$ 3.5 Hz, 1H, H-2), 3.81 (ddd, J5.1 Hz, J6.5 Hz, J11.7, 1H, —OCHH'—), 4.71 (d, J$_{1,2}$ 1.8 Hz, 1H, H-1); $^{13}$C NMR (100 MHz, D$_2$O) δ 32.1 (—CH,Br), 61.7 (—OCH$_2$—), 67.5, 68.4, 70.7, 71.3, 73.8 (C-2, C-3, C-4, C-5, C-6), 100.5 (C-1); HRMS m/z (FAB+): Found 308.9985 (M+Na$^+$); C$_8$H$_{15}$O$_6$ $^{79}$BrNa requires 308.9950. NaSSO$_2$CH$_3$ (150 mg, 1.12 mmol) was added to a solution of 4d (See FIG. 7) (245 mg, 0.85 mmol) in DMF (10 mL) under N$_2$ and warmed to 50° C. After 16 hours, the solution was cooled and the solvent removed. The residue was purified by flash chromatography (MeOH:EtOAc, 1:9) to give 1d (See FIG. 7) (217 mg, 80%) as a hygroscopic foam; [α]$^{29}_D$=+58.0 (c 1.34, H$_2$O); IR (KBr) 3441 cm$^{-1}$ (OH), 1314, 1132 cm$^{-1}$ (S—SO$_2$); $^1$H NMR (500 MHz, D$_2$O) δ 3.31 (t, J 5.8 Hz, 2H, —CH$_2$S—), 3.35 (s, 3H, CH$_3$SO$_2$—), 3.45 (t, J9.6 Hz, 1H, H-4), 3.49 (ddd, J$_{4,5}$ 9.8 Hz, J$_{5,6}$ 5.8 Hz, J$_{5,6'}$ 1.9 Hz, 1H, H-5), 3.55 (dd, J$_{5,6}$ 5.8 Hz, J$_{6,6'}$ 12.1 Hz, 1H, H-6), 3.60 (dd, J$_{2,3}$ 3.4 Hz, J$_{3,4}$ 9.0 Hz, 1H, H-3), 3.66 (dt, J$_d$ 10.7 Hz, J$_t$ 5.7 Hz, 1H, —OCHH'—), 3.69 (dd, J$_{5,6'}$ 1.9 Hz, J$_{6,6'}$ 12.1 Hz, 1H, H-6'), 3.77 (dd, J$_{1,2}$ 1.6 Hz, J$_{2,3}$ 3.4 Hz, 1H, H-2), 3.83 (dt, J$_d$ 11.0 Hz, J$_t$ 5.9 Hz, 1H, —OCHH'—), 4.72 (d, J$_{1,2}$ 1.6 Hz, 1H, H-1); $^{13}$C NMR (125 MHz, D$_2$O) δ 36.7 (—CH$_2$S—), 50.7 (CH$_3$SO$_2$—), 61.9 (—OCH$_2$—), 66.7, 67.7, 70.9, 71.5, 74.0 (C-2, C-3, C-4, C-5, C-6), 100.8 (C-1); HRMS m/z (FAB+): Found 319.0528 (M+H$^+$); C$_9$H$_{19}$O$_8$S$_2$ requires 319.0521.

Preparation of 2-(2,3,4,6-Tetra-O-acetyl-β-D-galactopyranosyl)ethyl methanethiosulfonate (1j).

BF$_3$.Et$_2$O (8.5 mL, 67.0 mmol) was added dropwise to a solution of of 1,2,3,4,6-penta-O-acetyl-α,β-D-galactose (5e) (See FIG. 7) (5.1 g, 13.1 mmol) and Br(CH$_2$)$_2$OH (1.15 mL, 16.2 mmol) in CH$_2$Cl$_2$ (24 mL) at 0° C. under N$_2$. After 1 hour, the solution was warmed to room temperature. After 24 hours, the reaction solution was added to ice water (20 mL) and extracted with CH$_2$Cl$_2$ (30 mL×3). These extracts were combined, washed with water (20 mL), sat. NaHCO$_3$ (aq., 20 mL), water (20 mL), dried (MgSO$_4$), filt Vogtle ered, and the solvent removed. The residue purified by flash chromatography (EtOAc:hexane, 1:3) to give 2-bromoethyl 2,3,4,6-tetra-O-acetyl-β-D-galactopyranoside (4j) (See FIG. 7) (4.01 g, 67%) as a white solid; mp 116–117° C. (EtOAc/hexane) [lit., (Coles et al., *J. Am. Chem. Soc.*, 60:1020–1022 (1938), which is hereby incorporated by reference) 111° C.; lit., (Dahmén et al., "2-Bromoethyl Glycosides—Synthesis and Characterization," *Carbohydr. Res.*, 116:303–307 (1983), which is hereby incorporated by reference) 114–116° C. (EtOAc/light pet. ether)]; [α]$^{27}_D$=−3.8 (c 0.81, CHCl$_3$) [lit., (Dahmén et al., "2-Bromoethyl Glycosides—Synthesis and Characterization," *Carbohydr. Res.*, 116:303–307 (1983), which is hereby incorporated by reference) [α]$^{23}_D$=−5 (c 1.4, CDCl$_3$)]; $^1$H NMR (200 MHz, CDCl$_3$) δ 1.98, 2.05, 2.08, 2.15 (s×4, 3H×4, Ac×4), 3.43–3.50 (m, 2H), 3.75–3.95 (m, 2H), 4.12–4.24 (m, 3H), 4.53 (d, J$_{1,2}$ 8 Hz, 1H, H-1), 5.02 (dd, J$_{2,3}$ 11 Hz, J$_{3,4}$ 3 Hz, 1H, H-3), 5.23 (dd, J$_{1,2}$ 8 Hz, J$_{2,3}$ 11 Hz, 1H, H-2), 5.40 (br d, J$_{3,4}$ 3 Hz, 1H, H-4). NaSSO$_2$CH$_3$ (85 mg, 0.63 mmol) was added to a solution of 4j (See FIG. 7) (223 mg, 0.49 mmol) in DMF (6 mL) under N$_2$ and warmed to 55° C. After 30 hours, the solution was cooled and the solvent removed. The residue was purified by flash chromatography (EtOAc:hexane, 1:1) to give 1j (See FIG. 7) (198 mg, 83%) as a white foam; [α]$^{27}_D$=+9.1 (c 1.41, CHCl$_3$); IR (film) 1747 cm$^{-1}$ (C═O), 1320, 1133 cm$^{-1}$ (S—SO$_2$); $^1$H NMR (500 MHz, CDCl$_3$) δ 1.98, 2.05, 2.09, 2.15 (s×4, 3H×4, Ac×4), 3.35 (s, 3H, CH$_3$SO$_2$—), 3.35–3.38 (m, 2H, —CH$_2$S—), 3.84 (ddd, J 6.1 Hz, J 7.1 Hz, J 10.5 Hz, 1H, —OCHH'—), 3.92 (td, J$_{4,5}$ 1.1 Hz, J$_t$ 6.6 Hz, 1H, H-5), 4.10–4.21 (m, 3H, H-6, H-6', —OCHH'—), 4.52 (d, J$_{1,2}$ 8.0 Hz, 1H, H-1), 5.01 (dd, J$_{2,3}$ 10.3 Hz, J$_{3,4}$ 3.5 Hz, 1H, H-3), 5.20 (dd, J$_{1,2}$ 8.0 Hz, J$_{2,3}$ 10.3 Hz, 1H, H-2), 5.40 (dd, J$_{3,4}$ 3.5 Hz, J$_{4,5}$ 1.1 Hz, 1H, H-4); $^{13}$C NMR (100 MHz, CDCl$_3$) δ 20.6, 20.7, 20.8 (CH$_3$COO—×4), 36.1, (—CH$_2$S—), 50.6 (CH$_3$SO$_2$—), 61.2 (—OCH$_2$—). 67.0, 68.3, 68.5, 70.8, 71.0 (C-2, C-3, C-4, C-5, C-6), 101.3 (C-1), 169.5, 170.0, 170.1, 170.4 (CH$_3$COO—×4); HRMS m/z (FAB+): Found 487.0936 (M+H$^+$); C$_{17}$H$_{27}$O$_{12}$S$_2$ requires 487.0944.

Preparation of 2-(β-D-Galactopyranosyl)ethyl methanethiosulfonate (1e).

A solution of NaOMe (0.104 M, 0.8 mL) was added to a solution of 4j (See FIG. 7) (778 mg, 1.71 mmol) in MeOH (10 mL) under N$_2$. After 4 hours, the reaction solution was passed through a Dowex 50W(H$^+$) plug (3×1 cm, eluant MeOH) and the solvent removed to give 2-bromoethyl β-D-galactopyranoside (4e) (See FIG. 7) (450 mg, 92%) (The synthesis of unstable 4e has been described previously. Dahmén et al., "2-Bromoethyl Glycosides .4.2-Bromoethyl Glycosides in Glycoside Synthesis—Preparation of Glycoproteins Containing Alpha-L-Fuc-(1–>2)-D-Gal and Beta-D-Gal-(1>4)-D-Glcnac," *Carbohydr. Res.*, 125:237–245 (1984), which is hereby incorporated by reference) as a white solid which was used directly in the next step. NaSSO$_2$CH$_3$ (180 mg, 1.34 mmol) was added to a solution 4e (See FIG. 7) (290 mg, 1.01 mmol) in DMF (12 mL) under N$_2$ and warmed to 50° C. After 15 hours, the solution was cooled and the solvent removed. The residue was purified by flash chromatography (MeOH:EtOAc, 1:9) to give 1e (See FIG. 7) (229 mg, 71%) as a white foam; [α]$^{27}_D$=+2.9 (c 0.58, H$_2$O); IR (film) 3358 cm$^{-1}$ (br, O—H), 1306, 1120 cm$^{-1}$ (S—SO$_2$); $^1$H NMR (500 MHz, D$_2$O, COSY) δ 3.29–3.33 (m, 2H, —CH$_2$S—), 3.30 (dd, J$_{1,2}$ 7.7 Hz, J$_{2,3}$ 10.0 Hz, 1H, H-2), 3.35 (s, 3H, CH$_3$SO$_2$—), 3.43 (dd, J$_{2,3}$ 10.0 Hz, J$_{3,4}$ 3.6 Hz, 1H, H-3), 3.48 (ddd, J$_{4,5}$ 0.9Hz, J$_{5,6}$ 4.3 Hz, J$_{5,6'}$ 7.9 Hz, 1H, H-5), 3.52 (dd, J$_{5,6}$ 4.3 Hz, J$_{6,6}$ 11.7 Hz, 1H, H-6), 3.57 (dd, J$_{5,6'}$ 7.9 Hz, J$_{6,6}$ 11.7 Hz, 1H, H-6'), 3.70 (dd, $_{3,4}$ 3.6 Hz, J$_{4,5}$ 0.9 Hz, 1H, H-4), 3.80 (dt, J$_d$ 11.2 Hz, $J_t$ 6.1 Hz, 1H, —OCHH'—), 4.01 (dt, $J_d$ 11.4 Hz, $J_t$ 5.8 Hz, 1H, —OCHH'—), 4.24 (d, $J_{1,2}$ 7.7 Hz, 1H, H-1); $^{13}$C NMR (100 MHz, D$_2$O) δ 36.7 (—CH$_2$S—), 50.8 (CH$_3$SO$_2$—), 61.9 (—OCH$_2$—), 69.2, 69.6, 71.7, 73.7, 76.2 (C-2, C-3, C-4, C-5, C-6), 104.0 (C-1); HRMS m/z (FAB+): Found 319.0523 (M+H$^+$); C$_9$H$_{19}$O$_8$S$_2$ requires 319.0521.

Preparation of 2-(2, 3, 6-Tri—O-acetyl-4-O-(2,3,4, 6-tetra-O-acetyl-β-D-galactopyranosyl)-β-D-glucopyranosyl)ethyl methanethiosulfonate (1k).

BF$_3$.Et$_2$O (4.0 mL, 31.5 mmol) was added dropwise to a solution of 1,2,3,6-tetra-O-acetyl-4-O-(2,3 ,4,6-tetra-O-acetyl-β-D-galactopyranosyl)-β-D-glucopyranoside (5f) (See FIG. 7) (5 g, 7.4 mmol) and Br(CH$_2$)$_2$OH (0.65 mL, 9.2 mmol) in CH$_2$Cl$_2$ (15 mL) at 0° C. under N$_2$. After 1 hour, the solution was warmed to room temperature. After 20 hours, the reaction solution was added to ice water (15 mL) and extracted with CH$_2$Cl$_2$ (20 mL×2). These extracts were combined, washed with water (20 mL), sat. NaHCO$_3$ (aq., 20 mL), water (20 mL), dried (MgSO$_4$), filtered, and the solvent removed. The residue was purified by flash chromatography (EtOAc:hexane, 1:1) to give 2-bromoethyl 2,3,6-tri—O-acetyl-4-O-(2,3,4,6-tetra-O-acetyl-β-D-galactopyranosyl)-β-D-glucopyranoside (4k) (See FIG. 7) (2.94 g, 53%) as a white foam; $[\alpha]^{27}_D$=−7.8 (c 1.28, CHCl$_3$) [lit., (Dahmén et al., "2-Bromoethyl Glycosides—Synthesis and Characterization," *Carbohydr. Res.*, 116:303–307 (1983), which is hereby incorporated by reference) $[\alpha]^{23}_D$=−11 (c 1.3, CHCl$_3$)]; $^1$H NMR (500 MHz, CDCl$_3$, COSY) δ 1.94, 2.02, 2.02 (s×3, 3H×3, Ac×3), 2.04 (s, 6H, Ac×2), 2.10, 2.13 (s×2, 3H×2, Ac×2), 3.38–3.46 (m, 2H, —CH$_2$Br), 3.59 (ddd, $J_{5',6'''}$ 2.2 Hz, J4.9 Hz, J9.9 Hz, 1H, H-5'), 3.75–3.80 (m, 2H, H-4', —OCHH'—), 3.85 (td, $J_{4,5}$ 1.1 Hz, $J_t$ 6.9 Hz, 1H, H-5), 4.03–4.12 (m, 4H, H-6, H-6', H-6", —OCHH'—), 4.45 (d, $J_{1,2}$ 7.8 Hz, 1H, H-1), 4.48 (dd, $J_{5',6'''}$ 2.2 Hz, $J_{6'',6'''}$ 12.1 Hz, 1H, H-6'''), 4.50 (d, $J_{1',2'}$ 7.9Hz, 1H, H-1'), 4.89 (dd, $J_{1',2'}$ 7.9 Hz, $J_{2',3'}$ 9.6 Hz, 1H, H-2'), 4.92 (dd, $J_{2,3}$ 10.5 Hz, $J_{3,4}$ 3.4 Hz, 1H, H-3), 5.08 (dd, $J_{1,2}$ 7.8 Hz, $J_{2,3}$ 10.5 Hz, 1H, H-2), 5.18 (t, J9.6 Hz, 1H, H-3'), 5.32 (dd, $J_{3,4}$ 3.4 Hz, $J_{4,5}$ 1.1 Hz, 1H, H-4). NaSSO$_2$CH$_3$ (87 mg, 0.65 mmol) was added to a solution of 4k (See FIG. 7) (357 mg, 0.48 mmol) in DMF (6 mL) under N$_2$ and warmed to 50° C. After 22 hours, the solution was cooled and the solvent removed. The residue was purified by flash chromatography (EtOAc:hexane, 11:9) to give 1k (See FIG. 7) (327 mg, 88%) as a white foam; $[\alpha]^{27}_D$=−3.7 (c 1.0, CHCl$_3$); IR (KBr) 1751 cm$^{-1}$ (C=O), 1323, 1134 cm$^{-1}$ (S—SO$_2$); $^1$H NMR (500 MHz, CDCl$_3$, COSY) δ 1.94, 2.02, 2.02, 2.04, 2.04, 2.11, 2.13 (s×7, 3H×7, Ac×7), 3.29–3.40 (m, 2H, —CH$_2$S—), 3.32 (s, 3H, CH$_3$SO$_2$—), 3.59 (ddd, $J_{4',5'}$ 9.9 Hz, $J_{5',6''}$ 4.9 Hz, $J_{5',6'''}$ 2.2 Hz, 1H, H-5'), 3.77 (t, J9.5 Hz, 1H, H-4'), 3.79–3.86 (m, 2H, H-5, —OCHH'—), 4.03–4.13 (m, 4H, H-6, H-6', H-6", —OCHH—), 4.46 (d, $J_{1,2}$ 7.8 Hz, 1H, H-1), 4.50 (d, $J_{1',2'}$ 8.0 Hz, 1H, H-1'), 4.52 (dd, $J_{5',6''}$ 2.2 Hz, $J_{6'',6'''}$ 11.9 Hz, 1H, H-6'''), 4.87 (dd, $J_{1',2'}$ 8.0 Hz, $J_{2',3'}$ 9.6 Hz, 1H, H-2'), 4.93 (dd, $J_{2,3}$ 10.5 Hz, $J_{3,4}$ 3.5 Hz, 1H, H-3), 5.08 (dd, $J_{1,2}$ 7.8 Hz, $J_{2,3}$ 10.5 Hz, 1H, H-2), 5.17 (t, J9.3 Hz, 1H, H-3'), 5.32 (dd, $J_{3,4}$ 3.5 Hz, $J_{4,5}$ 1.0 Hz, 1H, H-4); $^{13}$C NMR (125 MHz, CDCl$_3$, DEPT) δ 20.5, 20.7, 20.8, 20.9 (q×4, CH$_3$COO—×7), 36.0 (t, —CH$_2$S—), 50.6 (q, CH$_3$SO$_2$—), 60.7, 61.6, 68.5 (t×3, —OCH$_2$—, C-6, C-6'), 66.5, 69.0, 70.6, 70.9, 71.3, 72.6, 72.8, 76.0 (d×8, C-2, C-3, C-4, C-5, C-2', C-3', C-4', C-5'), 100.7, 101.1 (d×2, C-1, C-1'), 169.1, 169.7, 169.7, 170.1, 170.2, 170.3, 170.4 (s×7, CH$_3$COO—×7); HRMS m/z (FAB+): Found 775.1793 (M+H$^+$); C$_{29}$H$_{43}$O$_{20}$S$_2$ requires 775.1789.

Preparation of 2-(4-O-β-D-Galactopyranosyl-β-D-glucopyranosyl)ethyl methanethiosulfonate (1f).

A solution of NaOMe (0.1 M, 0.6 mL) was added to a solution of 4k (See FIG. 7) (877 mg, 1.18 mmol) in MeOH (6 mL) under N$_2$. After 3 hours, the reaction solution was passed through a Dowex 50W(H$^+$) plug (4×1 cm, eluant MeOH) and the solvent removed to give 2-bromoethyl 4-O-β-D-galactopyranosyl-β-D-glucopyranoside (4f) (See FIG. 7) (476 mg, 90%) as a white foam which was used directly in the next step. NaSSO$_2$CH$_3$ (185 mg, 1.38 mmol) was added to a solution of 4f (See FIG. 7) (476 mg, 1.06 mmol) in DMF (24 mL) under N$_2$ and warmed to 50° C. After 21 hours, the solution was cooled and the solvent removed. The residue was purified by flash chromatography (CHCl$_3$:MeOH: AcOH: H$_2$O, 60:30:3:5) to give If (See FIG. 7) (346 mg, 68%) as a hygroscopic foam; $[\alpha]^{28}_D$=+1.5 (c 1.66, H$_2$O); IR (KBr) 3416 cm$^{-1}$ (br, OH), 1311, 1131 cm$^{-1}$ (S—SO$_2$); $^1$H NMR (400 MHz, D$_2$O, COSY) δ 3.10–3.13 (m, 1H, H-2), 3.30 (t, J6.0 Hz, 2H —CH$_2$S—), 3.31 (dd, $J_{1',2'}$ 7.8 Hz, $J_{2',3'}$ 10.3 Hz, 1H, H-2'), 3.34 (s, 3H, CH$_3$SO$_2$—), 3.38–3.54 (m, 5H), 3.44 (dd, $J_{2',3'}$ 10.3 Hz, $J_{3',4'}$ 3.3 Hz, 1H, H-3'), 3.57 (dd, J8.4 Hz, J 11.4 Hz, 1H), 3.59 (dd, J4.9 Hz, J7.3 Hz, 1H), 3.70 (br d, $J_{3',4'}$ 3.3 Hz, 1H, H-4'), 3.77 (dd, J1.0 Hz, J11.5 Hz, 1H), 3.79–3.83 (m, 1H, —OCHH'—), 3.97–4.02 (m, 1H, —OCHH'—), 4.22 (d, $J_{1',2'}$ 7.8 Hz, 1H, H-1'), 4.33 (d, $J_{1,2}$ 7.8 Hz, 1H, H-1); $^{13}$C NMR (125 MHz, D$_2$O) δ 36.7 (—CH$_2$S—), 50.8 (CH$_3$SO$_2$—), 61.0, 62.1, 69.4, 69.6, 71.9, 73.5, 73.7, 75.3, 75.9, 76.4, 79.3 (—OCH$_2$—, C-2, C-3, C-4, C-5, C-6, C-2', C-3', C-4', C-5', C-6'), 103.3, 103.9 (C-1, C-1'); HRMS m/z (FAB+): Found 503.0886 (M+Na$^+$); C$_{15}$H$_{28}$O$_{13}$S$_2$Na requires 503.0869.

Example 2
General Procedure for Modification of Subtilisin Bacillus lentus ("SBL") Mutants Stored as Flash-Frozen Solutions A 1.25 mL frozen aliquot of the mutant enzyme (SBL-N62C, -L217C, or -S166C) containing approximately 25 mg of enzyme was thawed and added to 1.25 mL of Modifying Buffer (see below) in a polypropylene test-tube. To this solution was added 100 μL of a 0.2 M glyco-MTS reagent solution (1a,g–k in MeCN, 1b–f in water (See FIG. 8)). The mixture was sealed, vortexed, and placed on an end-over-end rotator at room temperature. When the modification was complete (determined by a specific activity assay, using succinyl—AlaAlaProPhe—p-nitroanilide [$\epsilon_{410}$=8800 M$^{-1}$cm$^{-1}$] (Bonneau et al., "Alteration of the Specificity of Subtilisin BPN' by Site-Directed Mutagenesis in its S1 and S1' Binding-Sites," *J. Am. Chem. Soc.*, 119:1026–1030 (1991), which is hereby incorporated by reference) as substrate in 0.1 M Tris—HCl buffer containing 0.005% Tween 80, 1% DMSO, pH 8.6 showing constant activity and titration with Ellman's reagent ($\epsilon_{412}$=13600 M$^{-1}$ cm$^{-1}$) (Ellman et al., *Biochem. Pharmacol.*, 7:88–95 (1961), which is hereby incorporated by reference) showing no free thiol present in solution), a further 50 μL of the modifying reagent solution was added and the mixture placed back on the end-over-end rotator for a further 10 minutes. The reaction was poured onto a pre-packed, pre-equilibrated G-25 Sephadex® PD10 column and eluted with 3.5 mL Quench Buffer (see below). The eluant was dialysed at 4° C. against 10 mM MES, 1 mM CaCl$_2$ pH 5.8 (2×1L, 2×45 minutes). The resulting dialysate was flash frozen in liquid nitrogen and stored at −18° C.

Modifying Buffer:
pH 9.5: 140 mM CHES, 2 mM CaCl$_2$
pH 7.5: 140 mM HEPES, 2 mM CaCl$_2$
pH 6.5: 140 mM MES, 2 mM CaCl$_2$
pH 5.5: 140 mM MES, 2 mM CaCl$_2$ Quench Buffer:
  Reactions at pH 7.5–9.5: 5 mM MES 1 mM CaCl$_2$ pH 6.5
  Reactions at pH 5.5: 5 mM MES 1 mM CaCl, pH 5.5

The free thiol content of all chemically modified mutant enzymes ("CMMs"), was determined spectrophotometrically by titration with Ellman's reagent (Ellman et al., *Biochem. Pharmacol.*, 7:88–95 (1961), which is hereby incorporated by reference) in phosphate buffer 0.25 M, pH 8.0. In all cases, no free thiol was detected. Modified enzymes were analyzed by nondenaturing gradient (8–25%) gels at pH 4.2, run towards the cathode, on the Pharmacia Phast-system and appeared as a single band. Prior to ES-MS analysis, CMMs were purified by FPLC (BioRad, Biologic System, Hercules, Calif.) on a Source 15 RPC matrix (17-0727-20 from Pharmacia, Bridgewater, N.J.) with 5% acetonitrile, 0.01% TFA as the running buffer and eluted with 80% acetonitrile, 0.01% TFA in a one step gradient. MS m/z (ES-MS): N62C-S-a (See FIG. 8) calculated 27049, found 27051; N62C-S-b (See FIG. 8) calculated 26925, found 26928; N62C-S-c (See FIG. 8) calculated 26925, found 26928; N62C-S-d (See FIG. 8) calculated 26925, found 26925; N62C-S-e (See FIG. 8) calculated 26925, found 26925; N62C-S-f (See FIG. 8) calculated 27087, found 27087; N62C-S-g (See FIG. 8) calculated 27093, found 27096; N62C-S-Et-β-Glc(Ac)$_2$ calculated 27009, found 27015; N62C-S-Et-β-Glc(Ac)$_3$ calculated 27051, found 27053; N62C-S-i (See FIG. 8) calculated 27093, found 27098; N62C-S-Et-β-Gal(Ac)$_3$ calculated 27051, found 27051; N62C-S-k (See FIG. 8) calculated 27381, found 27386; L217C-S-β-Glc calculated 26882, found 26879; L217C-S-β-Glc(Ac)$_2$ calculated 26966, found 26962; L217C-S-β-Glc(Ac)$_3$ calculated 27008, found 27006; L217C-S-b (See FIG. 8) calculated 26926, found 26928; L217C-S-c (See FIG. 8) calculated 26926, found 26925; L217C-S-d (See FIG. 8) calculated 26926, found 26925; L217C-S-e (See FIG. 8) calculated 26926, found 26928; L217C-S-f (See FIG. 8) calculated 27088, found 27087; L217C-S-Et-α-Glc(Ac)$_2$ calculated 27010, found 27012; L217C-S-Et-β-Glc(Ac)$_3$ calculated 27052, found 27056; L217C-S-Et-α-Man(Ac)$_3$ calculated 27052, found 27056; L217C-S-Et-β-Gal(Ac)$_3$ calculated 27052, found 27053; L217C-S-Et-Lac(Ac)$_6$ calculated 27340, found 27342; S166C-S-a (See FIG. 8) calculated 27076, found 27080; SI66C-S-b (See FIG. 8) calculated 26952, found 26955; S166C-S-c (See FIG. 8) calculated 26952, found 26950; S166C-S-d (See FIG. 8) calculated 26952, found 26952; S166C-S-e (See FIG. 8) calculated 26952, found 26952; S166C-S-f (See FIG. 8) calculated 27114, found 27112; S166C-S-Et-α-Glc(Ac)$_3$ calculated 27078, found 27078; S166C-S-Et-β-Glc(Ac)$_2$ calculated 27036, found 27040; S166C-S-Et-β-Glc(Ac)$_3$ (major) with S166C-S-h (See FIG. 8) (minor) and S166C-S-Et-β-Glc(Ac)$_2$ (minor) calculated 27078 (major), 27120 (minor), 27036 (minor), found 27081 (major), 27121 (minor), 27036 (minor); S166C-S-Et-α-Man(Ac)$_3$ calculated 27078, found 27085; S166C-S-Et-β-Gal(Ac)$_3$ calculated 27078, found 27079; S166C-S-Et-Lac(Ac)$_5$ calculated 27324, found 27331.

Example 3
General procedure for modification of SBL mutants stored as lyophilized powders This procedure was only used with S156C, which is stored as a lyophilized powder to prevent dimerization. Into a polypropylene test tube was weighed about 25–30 mg of lyophilized S156C. This was dissolved in the following modifying buffers (2.5 mL):

pH 9.5: 70 mM CHES, 2 mM CaCl$_2$
pH 7.5: 70 mM HEPES, 2 mM CaCl$_2$
pH 6.5: 70 mM MES, 2 mM CaCl$_2$
pH 5.5: 70 mM MES, 2 mM CaCl$_2$

Glyco-MTS reagent was added and the reaction then proceeded as for the other mutants, using the appropriate quench buffer. MS m/z (ES-MS): S156C-S-a (See FIG. 8) calculated 27076, found 27079; S156C-S-b (See FIG. 8) calculated 26952, found 26955; S156C-S-c (See FIG. 8) calculated 26952, found 26952; S156C-S-d (See FIG. 8) calculated 26952, found 26952; S156C-S-e (See FIG. 8) calculated 26952, found 26952; S156C-S-f (See FIG. 8) calculated 26952, found 26952; S156C-S-g (See FIG. 8) calculated 27114, found 27115; S156C-S-h (See FIG. 8) calculated 27120, found 27123; S156C-S-i (See FIG. 8) calculated 27120, found 27122; S156C-S-j (See FIG. 8) calculated 27120, found 27123; S156C-S-k (See FIG. 8) calculated 27120, found 27120; S156C-S-k (See FIG. 8) calculated 27408, found 27411.

Example 4
Contents of Acetylated Glyco-CMM Libraries

The levels of acetylation of glyco-CMMs after modification of SBL cysteine mutants with 1a, g–k (See FIG. 8) at various pH levels were determined and are set forth in Tables 1 and 2, below.

TABLE 1

Levels of Acetylation of Glyco-CMMs after Modification of SBL Cysteine Mutants with 1a at various pH[a]

| Enzyme | Reagent | | |
|---|---|---|---|
| | 1a pH 9.5 | 1a pH 7.5 | 1a pH 5.5 |
| N62C | 4 | — | 4 |
| S156C | 4 | — | 4 |
| S166C | 4 | — | 4 |
| L217C | 0 | 2[b] | 3[b] |

[a]Isolated as single species unless indicated.
[b]Single product mass by ES-MS.

TABLE 2

Levels of Acetylation of Glyco-CMMs after Modification of SBL Cysteine Mutants with 1a, g–k at pH 5.5[a]

| Enzyme | Reagent | | | | | |
|---|---|---|---|---|---|---|
| | 1a | 1g | 1h | 1i | 1j | 1k |
| N62C | 4 | 4 | 3[b] | 4 | 3[b] | 7 |
| S156C | 4 | 4 | 4 | 4 | 4 | 7 |
| S166C | 4 | 3 | 3[c], 4[d], 2[d] | 3[b] | 3[b] | 5[b] |
| L217C | 3[b] | 2[b] | 3[b] | 3[b] | 3[b] | 6[b] |

[a]Isolated as single species unless indicated.
[b]Single product mass by ES-MS.
[c]Major component.
[d]Minor component.

Example 5
Incubation of L217C-S-β-Glc(Ac)$_3$ at pH 9.5

The general procedure for modification of SBL mutants stored as flash-frozen solutions was used to incubate 1.26 mg of L217C-S-β-Glc(Ac)$_3$ as a 0.5 mL aliquot in the absence of MTS reagent for 2 hours to give L217C-S-β-Glc as the sole product. MS m/z (ES-MS): L217C-S-β-Glc calculated 26882, found 26885.

Example 6

Active Site Titrations

The active enzyme concentration was determined as previously described (Hsia et al., "Active-Site Titration of Serine Proteases Using a Fluoride-Ion Selective Electrode and Sulfonyl Fluoride Inhibitors," *Anal. Biochem.*, 242:221–227 (1996), which is hereby incorporated by reference) by monitoring fluoride release upon enzyme reaction with α-toluenesulfonyl fluoride (PMSF) as measured by a fluoride ion sensitive electrode (Orion Research 96-09). The active enzyme concentration determined in this way was used to calculate $k_{cat}$ values for each CMM.

Example 7

Kinetic Measurements

Michaelis-Menten constants were measured at 25(±0.2)° C. by curve fitting (GraFit® 3.03, Erithacus Software Ltd., Staines, Middlesex, UK) of the initial rate data determined at nine concentrations (0.125 mM-3 .0 mM) of succinyl-AAPF-pNA substrate in 0.1 M Tris—HCl buffer containing 0.005% Tween 80, 1% dimethylsufoxide ("DMSO"), pH 8.6 ($\epsilon_{410}$=8800 $M^{-1}cm^{-1}$) (Bonneau et al., *J. Am. Chem. Soc.*, 119:1026–1030 (1991), which is hereby incorporated by reference).

Example 8

Figure 6:
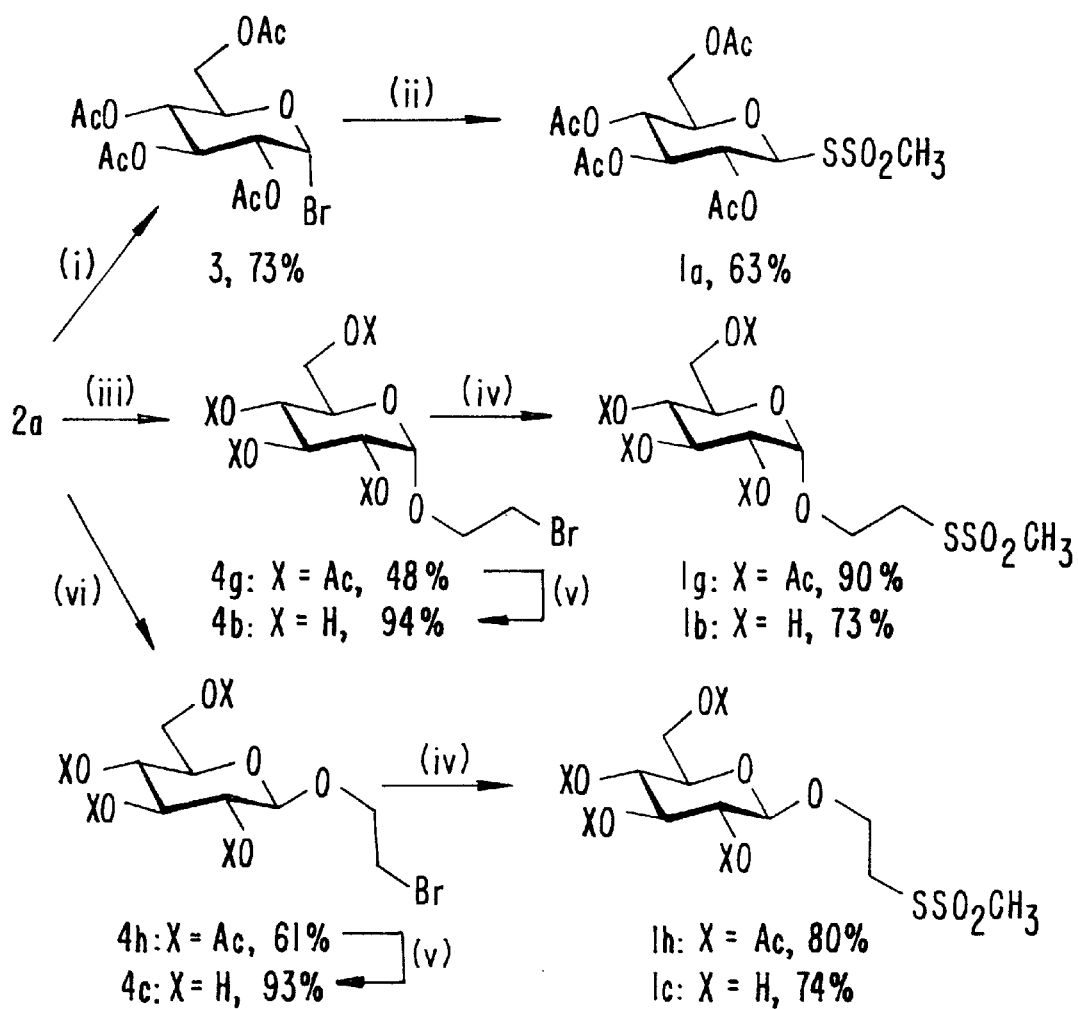
FIG. 6 shows the preparation of two types of glycosylating reagents from D-glucose (2a): the anomeric methanethiosulfonate 1a and the ethyl-tethered methanethiosulfonates 1b, c, g, h.
Figure 7:
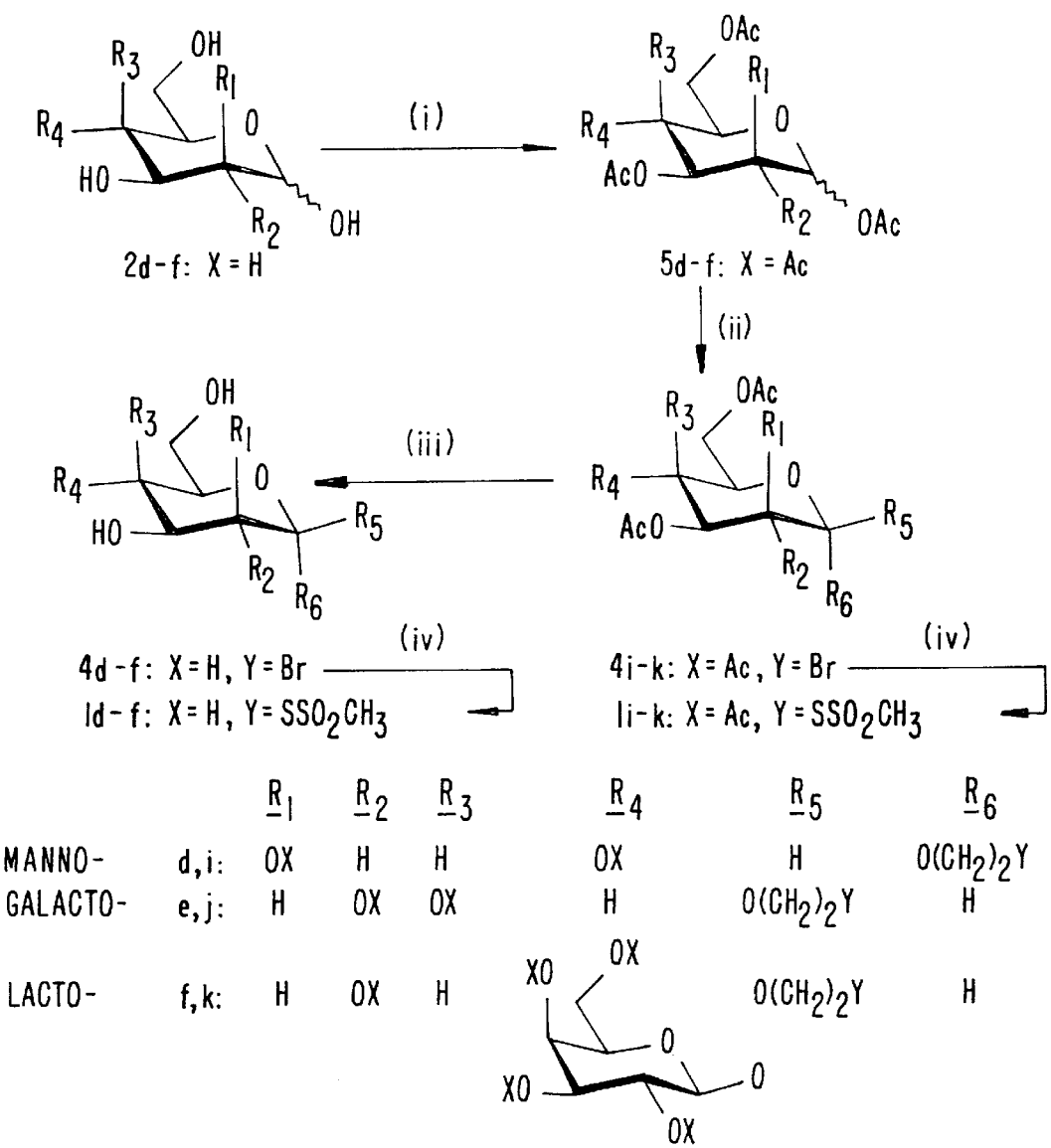
FIG. 7 shows the preparation of the α-D-manno-MTS reagents 1d and 1i, which are epimeric at C-2 relative to 1b and 1g, respectively, and the β-D-galacto-MTS reagents 1e and 1j, epimeric at C-4 relative to 1c and 1h, respectively.

Controlled Site Selective Glycosylation of Proteins by a Combined Site-Directed Mutagenesis and Chemical Modification Approach Four SBL sites at different locations and of different characteristics were selected for mutation to cysteine in order to provide a broad test of the glycosylation methodology. S156 of the $S_1$-pocket (Nomenclature of Schechter; Berger, *Biochem. Biophys. Res. Commun.*, 27:157–162 (1967), which is hereby incorporated by reference) is a surface-exposed residue that permits the introduction of externally-disposed glycans mirroring those found naturally in glycoproteins (*Molecular Glycobiology*, Fukuda et al., Eds., Oxford University, Oxford (1994), which is hereby incorporated by reference). In contrast, N62 in the $S_2$ pocket, S166 in the $S_1$ pocket, and L217 in the $S_1'$ pocket have side chains which are internally oriented and test the applicability of the method for introducing sugars at hindered locations. Broad applicability with respect to the sugar moiety was evaluated by using the representative series of protected and deprotected, mono- and disaccharide methanethiosulfonates ("MTS") 1a–k (see FIG. 8). These were prepared from their parent carbohydrates in good to excellent yields (FIGS. 6 (Reagents and Conditions: (i) $Ac_2O$, py then HBr, AcOH; (ii) $NaSSO_2CH_3$, EtOH, 90° C.; (iii) $Br(CH_2)_2OH$, $BF_3.Et_2O$ then $Ac_2O$, py; (iv) $NaSSO_2CH_3$, DMF, 50° C.; (v) NaOMe, MeOH; (vi) $Ac_2O$, py then $Br(CH_2)_2OH$, $BF_3.Et_2O$, DCM) and 7 (Reagents and Conditions: (i) $Ac_2O$, py. 92% for 5d, 99% for 5e; $Ac_2O$, NaOAc, 82% for 5f; (ii) $Br(CH_2)_2OH$, $BF_3.Et_2O$, DCM, 70% for 4i, 67% for 4j, 53% for 4k; (iii) NaOMe, MeOH, 96% for 4d, 92% for 4e, 90% for 4f; (iv) $NaSSO_2CH_3$, DMF, 50° C., 80% for 1d, 71% for 1e, 68% for 1f, 88% for 1i, 83% for 1j, 88% for 1k)). Two types of glycosylating reagents, the anomeric methanethiosulfonate 1a and the ethyl-tethered methanethiosulfonates 1b, c, g, h, were prepared from D-glucose (2a, FIG. 6). The preparation of these reagents in fully protected 1a, g, h and deprotected 1b, c forms allowed the effects of increased steric bulk and hydrophobicity to be assessed. Untethered MTS reagent 1a was readily prepared from acetobromoglucose (3) using $NaSSO_2CH_3$ as shown in FIG. 6 (Prepared from D-glucose according to Scheurer et al., *J. Am. Chem. Soc.*, 76:3224 (1954), which is hereby incorporated by reference). For the preparation of 1b, g, an α-linked ethyl tether was introduced using Fischer glycosidation of D-glucose (2) with 2-bromoethanol. Treatment of the tetraacetylbromide 4g with $NaSSO_2CH_3$ allowed the preparation of the peracetylated α-gluco-MTS 1g in an excellent 90% yield. Zemplén deacylation (Zemplén et al., *Ber. Dtsch. Chem. Ges.*, 56:1705–1710 (1923), which is hereby incorporated by reference) of bromide 4g and subsequent displacement of bromide by methanethiosulfonate ion proceeded smoothly to yield the fully deprotected (α-gluco-MTS 1b in 69% yield. The β-D-gluco-MTS reagents 1c and 1h, which are epimeric at C-1 relative to 1b and 1g, respectively, were prepared from the corresponding peracetylated β-bromide 4h. The preparation of 4h took advantage of well-defined methodology utilizing Lewis acid catalyzed displacement of anomeric acetates by alcohols (Dahmén et al., "2-Bromoethyl Glycosides—Synthesis and Characterization," *Carbohydr. Res.*, 116:303–307 (1983), which is hereby incorporated by reference). The protected bromide 4h was elaborated to the corresponding peracetylated (1h) and deprotected (1c) β-gluco-MTS reagents in an essentially identical manner to that used for the epimeric α-gluco-MTS reagents. Thus, using $NaSSO_2CH_3$, 4h gave 1h in 78% yield and, following deprotection, 4c (Helferich et al., *Just. Lieb. Ann. Chem.*, 541:1–16 (1939), which is hereby incorporated by reference) afforded 1c in 68% yield from 4h. Parallel routes allowed similarly efficient access to the α-D-manno-MTS reagents 1d and 1i, which are epimeric at C-2 relative to 1b and 1g, respectively, and the β-D-galacto-MTS reagents 1e and 1j, epimeric at C-4 relative to 1c and 1h, respectively (FIG. 7). The ready adaptability of this method to oligosaccharides was illustrated by the preparation of the peracetylated (1k) and fully deprotected (1f) disaccharide lacto-MTS reagents, in good overall yields from lactose (2f) of 38% and 27% respectively without cleavage of the interresidue bond.

Example 9

Site Specific Glycosylation.

The glyco-MTS reagents 1a–k (See FIG. 8) were reacted with the chosen cysteine mutants SBL-N62C, -S156C, -S166C and -L217C in aqueous buffer under conditions described previously (Stabile et al., *Bioorg. Med. Chem. Lett.*, 6:2501–2512 (1996); Berglund et al., *J. Am. Chem. Soc.*, 119:5265–5266 (1997); DeSantis et al., *Biochem.*, 37:5968–5973 (1998), which are hereby incorporated by reference). These reactions were rapid and quantitative, as judged by monitoring of changes in specific activity and by titration of free thiols with Ellman's reagent (Ellman et al., *Biochem. Pharmacol.*, 7:88–95 (1961), which is hereby incorporated by reference). The glycosylated chemically modified mutants (CMMs) were purified by size-exclusion chromatography and dialysis, and their structures were confirmed by rigorous ES-MS analyses (±7 Da) as shown in Table 3 below:

TABLE 3

Properties and Kinetic Parameters of Modified Enzymes

| Entry | Reactant Enzyme | Pocket | MTS Reagent | Reacn. pH | Product(s) | $k_{cat}$ (s$^{-1}$) | $K_M$ (mM) | $k_{cat}/K_M$ (s$^{-1}$ mM$^{-1}$) |
|---|---|---|---|---|---|---|---|---|
| 1 | SBL-WT | — | — | — | — | 153 ± 4 | 0.73 ± 0.05 | 209 ± 15 |
| 2 | N62C | $S_2$ | — | — | — | 174 ± 9 | 1.90 ± 0.20 | 92 ± 11 |
| 3 | | | 1a | 9.5 | N62C-S-a$^b$ | 67.9 ± 3.5 | 0.52 ± 0.07 | 130.6 ± 18.8 |
| 4 | | | 1b | 6.5 | N62C-S-b$^b$ | 135.3 ± 3.5 | 0.94 ± 0.05 | 143.9 ± 8.5 |
| 5 | | | 1c | 6.5 | N62C-S-c$^b$ | 132.7 ± 4.0 | 1.25 ± 0.08 | 106.2 ± 7.5 |
| 6 | | | 1d | 6.5 | N62C-S-d$^b$ | 132.9 ± 3.1 | 1.04 ± 0.05 | 127.8 ± 6.8 |
| 7 | | | 1e | 6.5 | N62C-S-e$^b$ | 119.3 ± 3.6 | 0.99 ± 0.07 | 120.5 ± 9.3 |
| 8 | | | 1f | 6.5 | N62C-S-f$^b$ | 129.8 ± 2.4 | 1.04 ± 0.04 | 124.8 ± 5.3 |
| 9 | | | 1g | 5.5 | N62C-S-g$^b$ | 120.0 ± 2.7 | 0.52 ± 0.03 | 230.8 ± 14.3 |
| 10 | | | 1h | 6.5 | N62C-S-Et-β-Glc(Ac)$_2$$^c$ | 87.7 ± 4.2 | 1.63 ± 0.15 | 53.8 ± 5.8 |
| 11 | | | 1h | 5.5 | N62C-S-Et-β-Glc(Ac)$_3$$^c$ | 100.3 ± 3.5 | 1.86 ± 0.12 | 53.9 ± 4.0 |
| 12 | | | 1i | 5.5 | N62C-S-i$^b$ | 123.0 ± 1.6 | 1.05 ± 0.03 | 117.1 ± 3.7 |
| 13 | | | 1j | 5.5 | N62C-S-Et-β-Gal(Ac)$_3$$^c$ | 103.4 ± 4.3 | 2.36 ± 0.17 | 43.8 ± 3.6 |
| 14 | | | 1k | 5.5 | N62C-S-k$^b$ | 64.9 ± 1.5 | 0.88 ± 0.05 | 73.8 ± 4.5 |
| 15 | L217C | $S_1'$ | — | — | — | 41 ± 1 | 0.80 ± 0.04 | 51 ± 3 |
| 16 | | | 1a | 9.5 | L217C-S-β-Glc$^b$ | 27.7 ± 0.4 | 0.79 ± 0.03 | 35.1 ± 1.4 |
| 17 | | | 1a | 7.5 | L217C-S-β-Glc(Ac)$_2$$^c$ | 44.9 ± 2.0 | 0.44 ± 0.06 | 102.0 ± 14.6 |
| 18 | | | 1a | 5.5 | L217C-S-β-Glc(Ac)$_3$$^c$ | 36.3 ± 0.8 | 0.36 ± 0.03 | 100.8 ± 8.7 |
| 19 | | | 1b | 6.5 | L217C-S-b$^b$ | 57.8 ± 0.6 | 0.67 ± 0.02 | 86.3 ± 2.7 |
| 20 | | | 1c | 6.5 | L217C-S-c$^b$ | 50.6 ± 0.9 | 0.67 ± 0.03 | 75.5 ± 3.6 |
| 21 | | | 1d | 6.5 | L217C-S-d$^b$ | 62.0 ± 1.3 | 0.55 ± 0.03 | 112.7 ± 6.6 |
| 22 | | | 1e | 6.5 | L217C-S-e$^b$ | 46.2 ± 0.8 | 0.63 ± 0.08 | 73.3 ± 3.7 |
| 23 | | | 1f | 6.5 | L217C-S-f$^b$ | 30.4 ± 0.6 | 0.46 ± 0.03 | 66.1 ± 4.5 |
| 24 | | | 1g | 5.5 | L217C-S-Et-α-Glc(Ac)$_2$$^c$ | 72.7 ± 3.1 | 0.73 ± 0.08 | 99.6 ± 11.8 |
| 25 | | | 1h | 5.5 | L217C-S-Et-β-Glc(Ac)$_3$$^c$ | 29.4 ± 0.8 | 0.93 ± 0.06 | 31.6 ± 2.2 |
| 26 | | | 1i | 5.5 | L217C-S-Et-α-Man(Ac)$_3$$^c$ | 97.8 ± 2.4 | 0.59 ± 0.04 | 165.8 ± 12.0 |
| 27 | | | 1j | 5.5 | L217C-S-Et-β-Gal(Ac)$_3$$^c$ | 39.2 ± 0.8 | 11.7 ± 0.05 | 33.5 ± 1.6 |
| 28 | | | 1k | 5.5 | L217C-S-Et-Lac(Ac)$_6$$^c$ | 27.1 ± 0.6 | 0.69 ± 0.04 | 39.3 ± 2.4 |
| 29 | S156C | $S_1$ | — | — | — | 125 ± 4 | 0.85 ± 0.06 | 147 ± 11 |
| 30 | | | 1a | 9.5 | S156C-S-a$^b$ | 54.8 ± 1.3 | 0.70 ± 0.04 | 78.3 ± 4.8 |
| 31 | | | 1b | 6.5 | S156C-S-b$^b$ | 77.0 ± 1.2 | 0.84 ± 0.03 | 91.7 ± 3.6 |
| 32 | | | 1c | 6.5 | S156C-S-c$^b$ | 76.6 ± 1.7 | 0.73 ± 0.04 | 104.9 ± 6.2 |
| 33 | | | 1d | 6.5 | S156C-S-d$^b$ | 88.6 ± 2.8 | 0.79 ± 0.06 | 112.2 ± 9.2 |
| 34 | | | 1e | 6.5 | S156C-S-e$^b$ | 78.9 ± 1.9 | 0.89 ± 0.04 | 89.7 ± 4.4 |
| 35 | | | 1f | 6.5 | S156C-S-f$^b$ | 63.6 ± 1.4 | 0.89 ± 0.05 | 71.8 ± 4.3 |
| 36 | | | 1g | 5.5 | S156C-S-g$^b$ | 43.6 ± 0.8 | 0.78 ± 0.04 | 55.9 ± 3.0 |
| 37 | | | 1h | 5.5 | S156C-S-h$^b$ | 64.0 ± 1.3 | 0.72 ± 0.04 | 88.9 ± 5.2 |
| 38 | | | 1i | 5.5 | S156C-S-i$^b$ | 60.3 ± 0.9 | 0.71 ± 0.03 | 84.9 ± 3.8 |
| 39 | | | 1j | 5.5 | S156C-S-j$^b$ | 51.9 ± 0.6 | 0.61 ± 0.02 | 85.1 ± 3.0 |
| 40 | | | 1k | 5.5 | S156C-S-k$^b$ | 53.6 ± 0.8 | 0.79 ± 0.03 | 67.4 ± 2.8 |
| 41 | S166C | S | — | — | — | 42 ± 1 | 0.50 ± 0.05 | 84 ± 9 |
| 42 | | | 1a | 9.5 | S166C-S-a$^b$ | 33.8 ± 1.3 | 0.66 ± 0.06 | 51.2 ± 5.0 |
| 43 | | | 1b | 6.5 | S166C-S-b$^b$ | 81.9 ± 1.1 | 11.4 ± 0.03 | 71.8 ± 2.1 |
| 44 | | | 1c | 6.5 | S166C-S-c$^b$ | 67.0 ± 2.2 | 0.99 ± 0.07 | 67.6 ± 5.3 |
| 45 | | | 1d | 6.5 | S166C-S-d$^b$ | 76.5 ± 2.0 | 11.7 ± 0.07 | 65.4 ± 4.3 |
| 46 | | | 1e | 6.5 | S166C-S-e$^b$ | 62.2 ± 1.4 | 10.8 ± 0.05 | 57.6 ± 3.0 |
| 47 | | | 1f | 6.5 | S166C-S-f$^b$ | 58.2 ± 1.2 | 10.2 ± 0.04 | 57.1 ± 2.5 |
| 48 | | | 1g | 5.5 | S166C-S-Et-α-Glc(Ac)$_3$$^c$ | 31.0 ± 0.8 | 0.77 ± 0.05 | 40.3 ± 2.8 |
| 49 | | | 1h | 6.5 | S166C-S-Et-β-Glc(Ac)$_2$$^c$ S166C-S-Et-β-Glc(Ac)$_3$$^d$ | 95.0 ± 2.1 | 0.87 ± 0.05 | 109.2 ± 6.7 |
| 50 | | | 1h | 5.5 | S166C-S-Et-β-Glc(Ac)$_2$$^c$ S166C-S-h$^e$ | 72.9 ± 1.7 | 0.65 ± 0.04 | 112.2 ± 7.4 |
| 51 | | | 1i | 5.5 | S166C-S-Et-α-Man(Ac)$_3$$^c$ | 67.7 ± 1.9 | 1.64 ± 0.09 | 41.3 ± 2.5 |
| 52 | | | 1j | 5.5 | S166C-S-Et-β-Gal(Ac)$_3$$^d$ | 65.1 ± 0.9 | 0.80 ± 0.03 | 81.3 ± 3.3 |
| 53 | | | 1k | 5.5 | S166C-S-Et-Lac(Ac)$_5$$^d$ | 67.4 ± 1.6 | 1.65 ± 0.07 | 40.8 ± 2.0 |

[a] Michaelis-Menten constants were measured at 25° C. according to the initial rates method in 0.1M Tris-HCl buffer at pH 8.6 0.005% Tween 80.1% DMSO. suc-AAPF-pNA as the substrate
[b] Single species
[c] Single product mass by ES-MS
[d] Major component
[e] Minor component The CMMs each appeared as a single band on non-denaturing gradient PAGE, thereby establishing their high purities. The active enzyme concentration of the resulting CMM solutions was determined by active site titration with α-toluenesulfonyl fluoride (PMSF) using a fluoride ion-sensitive electrode (Hsia et al., "Active-Site Titration of Serine Proteases Using a Fluoride-Ion Selective Electrode and Sulfonyl Fluoride Inhibitors," *Anal. Biochem.*, 242:221–227 (1996), which is hereby incorporated by reference). In all cases, modification with the fully deprotected reagents 1b–f (See FIG. 8) led to site-specific glycosylations and the formation of single glycoforms. Furthermore, modification with the protected MTS reagents 1a, g–k (See FIG. 8) gave products with controllable levels of acetylation. Through adjustment of pH and appropriate selection of the glycosylation site, differently acetylated glycoforms of SBL were prepared. This ability to modulate the level of acetylation through pH-control vastly expands the structural variety of glyco-CMMs that can be conveniently accessed and its scope was probed through the reaction of 1a (See FIG. 8) with SBL-N62C, -S156C, -S166C, -L217C (FIG. 9).

The extent of deacetylation during modification was highly site-dependent. Modification of L217C with reagent 1a (See FIG. 8) at pH 9.5 was accompanied by complete in situ deacetylation, and the sole product was the fully deprotected glucosylated-SBL, L217C-S-β-Glc. In contrast, treatment of N62C, S156C, and S166C with 1a (See FIG. 8) at pH 9.5 yielded only fully acetylated products, N62C-S-a (See FIG. 8), S156C-S-a (See FIG. 8), and S166C-S-a (See FIG. 8), respectively. To examine the effects of pH upon deacetylation, the reaction of L217C with 1a (See FIG. 8) was chosen. At pH 7.5 and 5.5, the products retained two and three acetate groups, forming L217C-S-β-Glc(Ac)$_2$ and L217C-S-β-Glc(Ac)$_3$, respectively. In all cases, complete integrity of the site selectivity was retained.

This valuable site-dependent deacetylation was attributed to a novel intramolecular SBL-catalyzed process. Although acetate esters are moderately chemically labile in aqueous solution at pH 9.5, they are not at either pH 7.5 or 5.5 (Greene et al., *Protective Groups in Organic Synthesis*, 2nd ed. New York, Wiley (1991), which is hereby incorporated by reference). The striking differences in behavior during modification between L217C and the three other mutants N62C, S156C, and S166C under identical reaction conditions discounted the possibility of deacetylation prior to modification. In addition, it was noted that position 217 bears an internally-oriented side chain and that modification of surface exposed position 156 showed no sign of deacetylation. This observation discounted both the possibility of either in situu chemical deacetylation or intermolecular enzymatic deacetylation. Furthermore, this ability of SBL to intramolecularly deacetylate was confirmed by the reaction of L217C-S-β-Glc(Ac)$_3$ at pH 9.5. Incubation of L217C-S-β-Glc(Ac)$_3$ under standard modification reaction conditions, but without reagent 1a (See FIG. 8), gave L217C-S-β-Glc as the sole product (FIG. 9).

Figure 8:
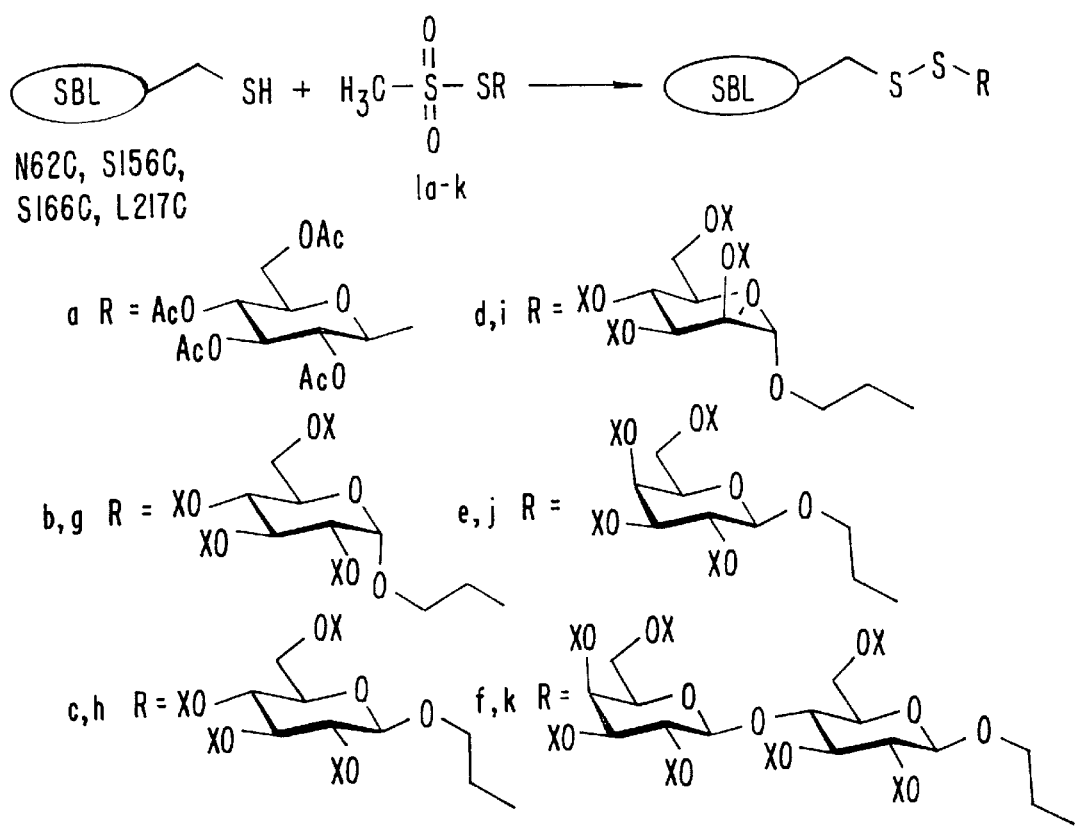
FIG. 8 shows the reaction of the thiol residue of cysteine introduced into subtilisin *Bacillus lentus* with glycomethanethiosulfonate reagents.
Figure 9:
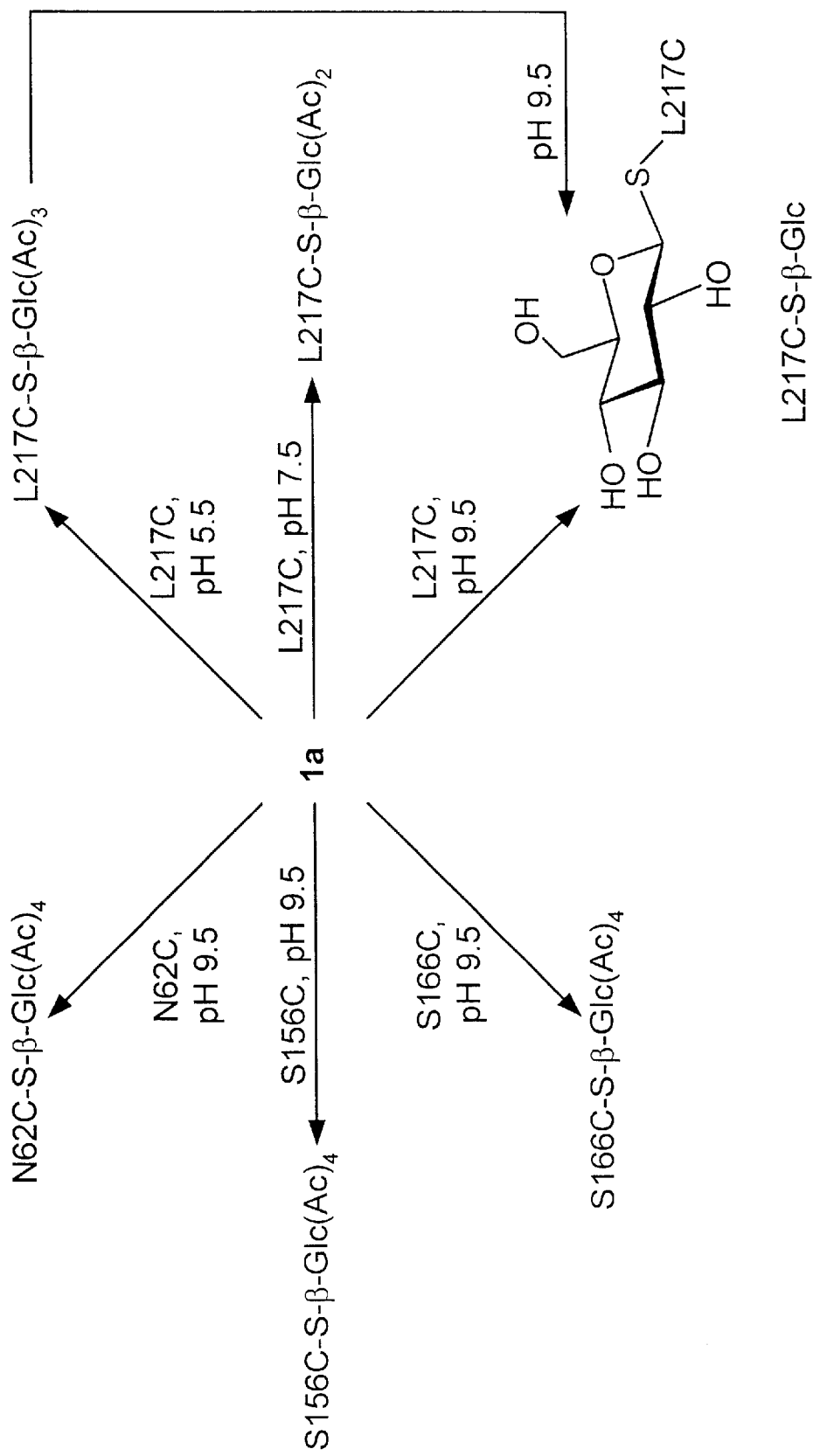
FIG. 9 shows the reaction of 2,3,4,6-tetra-O-acetyl-β-D-glucopyranosyl methanethiosulfonate (1a) with subtilisin *Bacillus lentus*-N62C, -S156C, -S166C, -L217C.

The enormous potential of this method was demonstrated by the preparation of a small library of differently acetylated glycosylated CMMs through the reaction of SBL-N62C, -S156C, -S166C, and -L217C with MTS reagents 1g–k (See FIG. 8). Using the pH-activity profiles of wild-type ("WT") and CMMs of SBL as a guide, pH 5.5 and 6.5 were chosen to minimize deacetylation. Typically, the specific activity of SBL and its CMMs drops sharply below pH 7.5 to levels that at pH 5.5 are 5–20% those at optimal pH (8.5–9.5) (Desantis et al., "Chemical Modifications at a Single Site Can Induce Significant Shifts in the pH Profiles of a Serine Protease," *J. Am. Chem. Soc.*, 120:8582–8586 (1998), which is hereby incorporated by reference). As expected, this drop in hydrolytic activity was reflected in the products of these modifications with 1g–k (See FIG. 8), which in all cases retained two or more acetate groups.

For example, at pH 5.5 reactions of SBL-L217C and -S166C created singly deacetylated CMMs, with the exception of pure dideacetylated glyco-CMMs L217C-S-Et-α-Glc (Ac)$_2$, and S166C-S-Lac(Ac)$_5$. The formation of the latter may reflect the presence of two primary acetates in disaccharidic MTS reagent 1k (See FIG. 8). Primary acetate groups are typically more labile than secondary acetate groups under conditions of intermolecular enzymatic deacetylation (Bashir et al., "Enzymatic Esterification and De-Esterification of Carbohydrates—Synthesis of a Naturally-Occurring Rhamnopyranoside of P-Hydroxybenzaldehyde and a Systematic Investigation of Lipase-Catalyzed Acylation of Selected Arylpyranosides," *J. Chem. Soc., Perkin Trans. I*, 2203–2222 (1995), which is hereby incorporated by reference). In contrast, reactions of SBL-S156C gave only the fully acetylated CMMs, S156C-S-g-k (See FIG. 8). This uniform lack of deacetylation observed for surface exposed glycans at position 156 was consistent with an intramolecular enzyme-catalyzed mechanism requiring internally-oriented acetate groups. Interestingly, the reactions of SBL-N62C were also determined by the anomeric configuration of 1g–k (See FIG. 8) with A-MTS reagents 1g,i (See FIG. 8) giving products that retained all acetate groups while P-MTS reagents 1h,j,k (See FIG. 8) were monodeacetylated. The range of accessible acetylated glyco-CMMs was further extended through modification at pH 6.5. For example, at position 62, it allowed the introduction of diacetylated P-glucose, forming N62C-S-Et-β-Glc(Ac)$_2$, in place of the triacetylated N62C-S-Et-β-Glc(Ac)$_3$ formed at pH 5.5. The range of acetylation at position 166 was similarly expanded through the formation S166C-S-Et-β-Glc(Ac)$_2$ in place of S166C-S-Et-β-Glc (Ac)$_3$.

Example 10
Glycan Structure-Hydrolytic Activity Relationships

Figure 10:
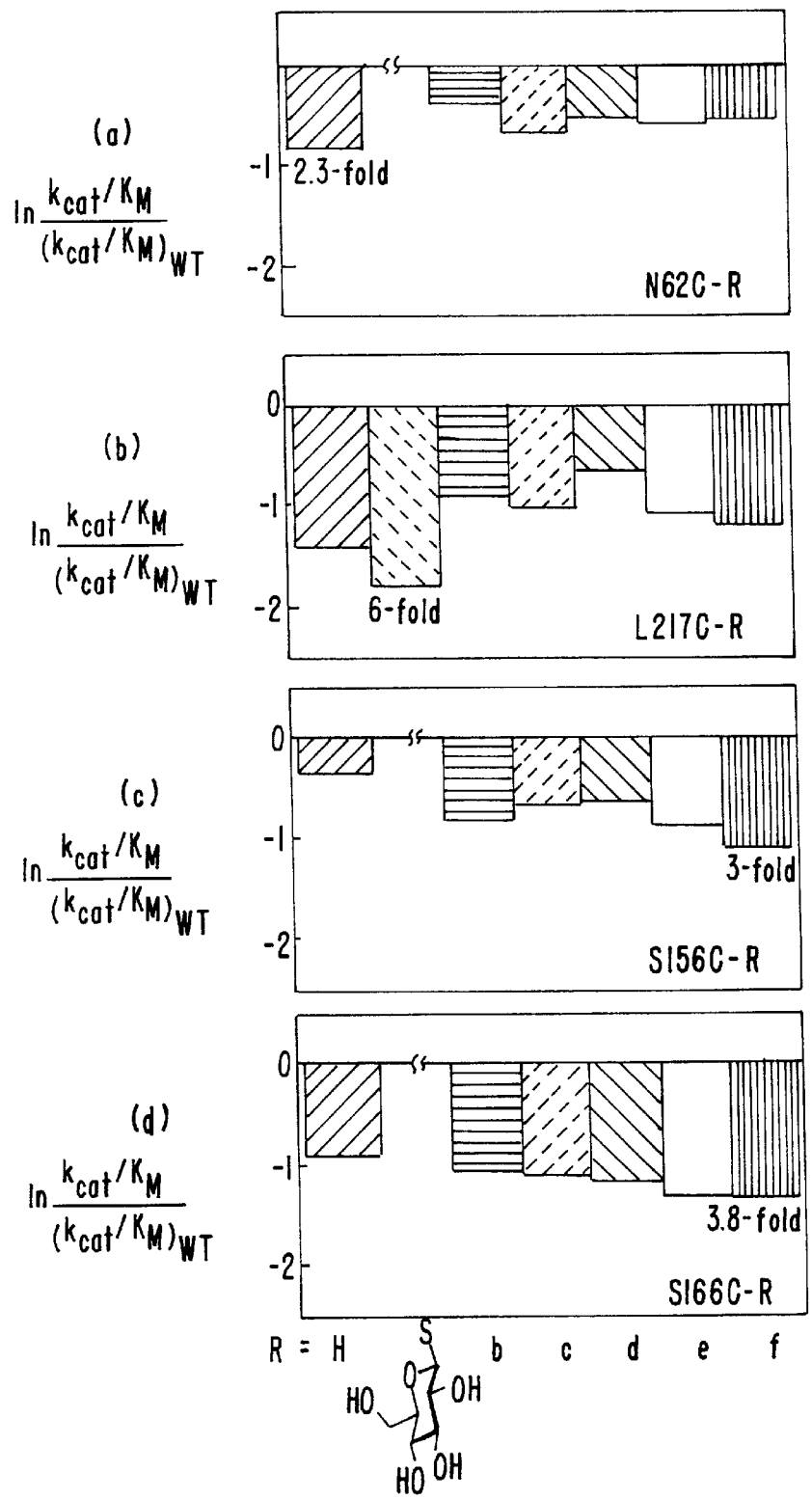
FIGS. 10A–D show deprotected glycan structure-proteolytic activity SARs of subtilisin *Bacillus lentus* cysteine mutants and glycosylated chemically modified mutant enzymes ("CMMs") relative to wild-type ("WT"). A break in the axis indicates that the value was not determined. At position 62, glycosylation partially restores the decrease in $k_{cat}/K_M$ caused by mutation to cysteine (R=H) (FIG. 10A). At position 217, the 4-fold decrease in activity caused by mutation (R=H) is amplified to 6-fold lower than WT by glycosylation with untethered S-β-Glc, but reduced to around 2.5-fold lower than WT by glycosylation with ethyl-tethered glycans (b–f) (FIG. 10B). At position 156, an arced variation in activity reaches a 3-fold lower than WT minimum $k_{cat}/K_M$ at bulky lacto-CMM S156C-S-f (FIG. 10C). At position 166, the 2.5-fold decrease in $k_{cat}/K_M$ caused by mutation is amplified by glycosylation. $k_{cat}/K_M$ decreases monotonically from S166C (R=H) to a value that is 3.8-fold lower than WT for S166C-S-f (FIG. 10D).
Figure 11:
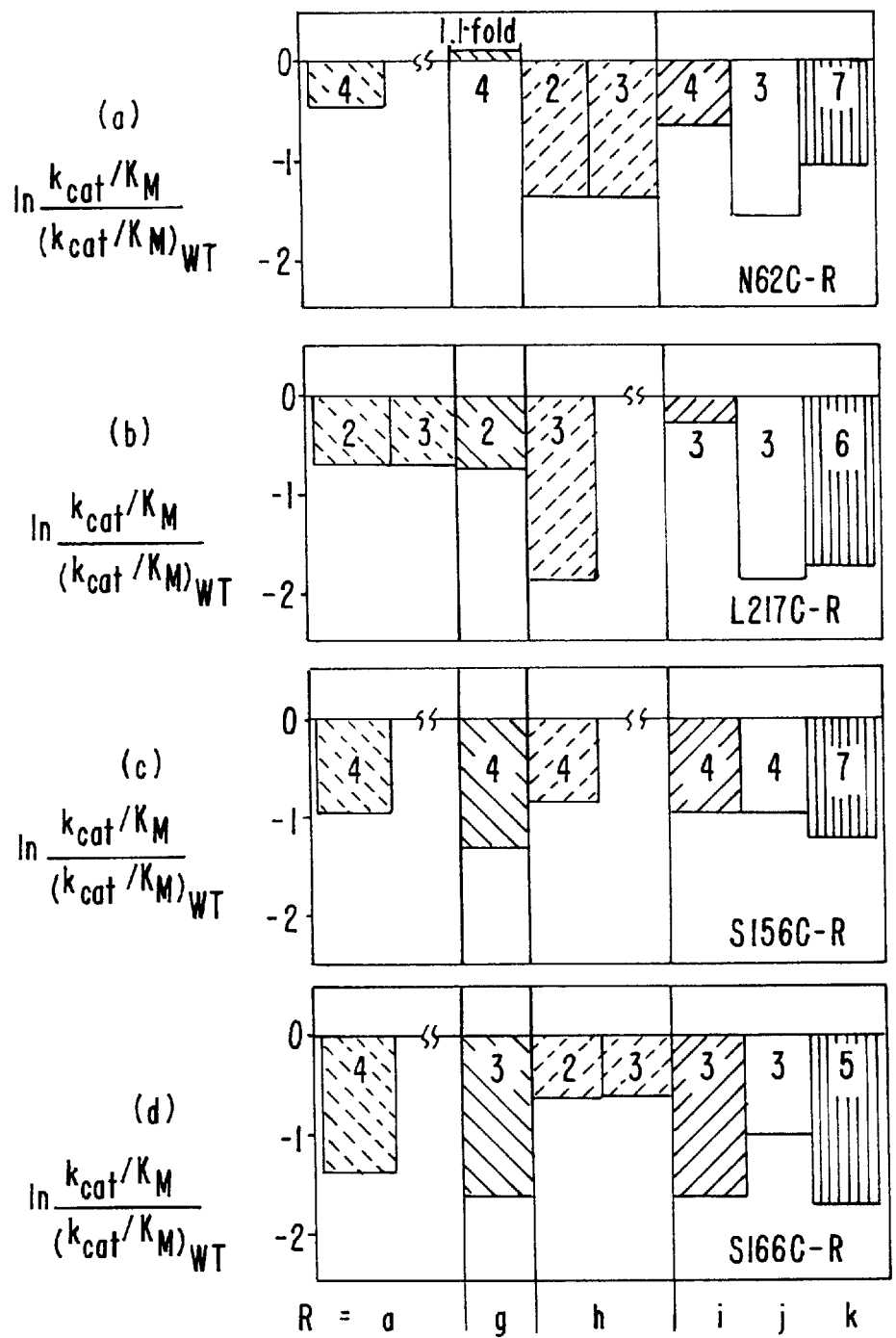
FIGS. 11A–D show the acetylated glycan structure-proteolytic activity SARs of glycosylated chemically modified mutant enzymes relative to WT. For each glycan the number of acetate groups present is indicated by a label on the corresponding bar. A break in the axis indicates that the value was not determined. At positions 62 (FIG. 11A), 217 (FIG. 11B), and 166 (FIG. 11D) an alternating trend in activity is observed as a result of the opposite effects of acetylation upon $k_{cat}/K_M$ according to anomeric stereochemistry (see FIG. 12). This results in a $k_{cat}/K_M$ for N62C-S-g that is 1.1-fold higher than WT. At position 156 (FIG. 11C), variations are slight and this is consistent with its surface exposed orientation.
Figure 12:
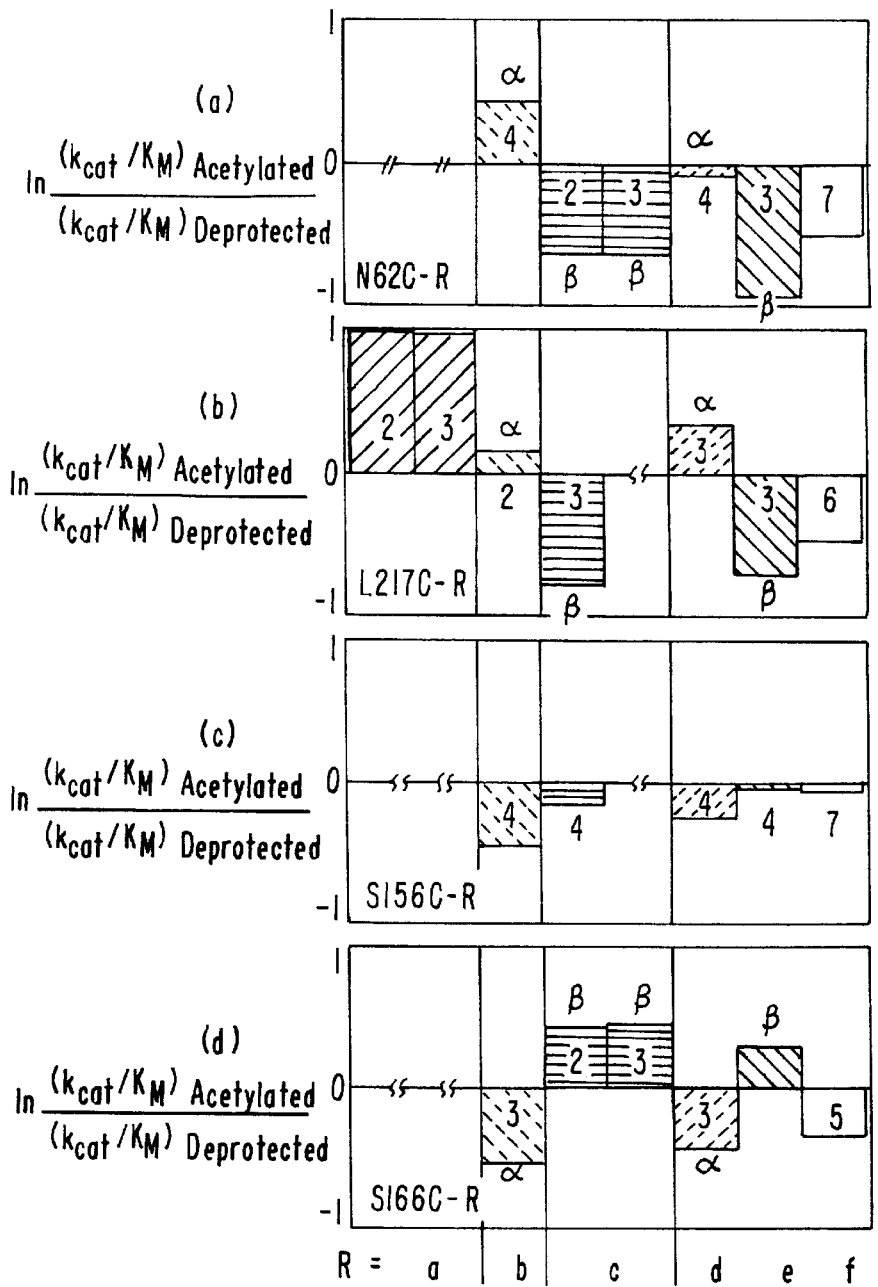
FIGS. 12A–D show the variation in proteolytic activity of glycosylated chemically modified mutant enzymes of subtilisin *Bacillus lentus* upon acetylation of glycans. Comparison of the activity of acetylated with fully deprotected chemically modified mutant enzymes shows that at positions 62 (FIG. 12A) and 217 (FIG. 12B) acetylation enhances the activity of α-tethered chemically modified mutant enzymes but decreases that of β-tethered. In contrast, at position 166 (FIG. 12D), acetylation decreases the activity of α-tethered CMMs but increases that of β-tethered. Consistent with its surface exposed orientation, changes at position 156 (FIG. 12C) are modest. For each glycan the number of acetate groups present is indicated by a label on the corresponding bar. A break in the axis indicates that the value was not determined.
Figure 12:
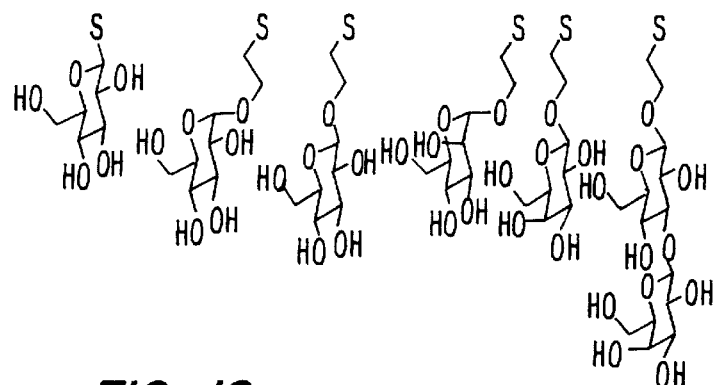

The effects of glycosylation upon SBL were assessed by the determination of $k_{cat}$ and $K_M$ for the hydrolysis of succinyl-AAPF-p-nitroanilide (Suc-AAPF-pNA) at pH 8.6. The kinetic parameters of the 48 CMMs generated were compared with those of WT and unmodified mutants in Table 3. The excellently selective and controlled method shown in FIG. 8 allowed the introduction of structurally related monosaccharides, D-glucose, D-galactose, and D-mannose, in addition to the more sterically bulky disaccharide lactose. From the resulting glycosylated CMMs, a detailed and precise set of structure-activity relationships was generated (FIGS. 10–12).

At position 62, in the $S_2$ pocket, the 2.3-fold reduction in $k_{cat}/K_M$ caused by mutation to cysteine was partially restored by glycosylation (FIG. 10A). The introduction of ethyl-tethered α- or β-glucose, β-galactose or α-mannose to N62C increased $k_{cat}/K_M$ and formed N62C-S-b-e (See FIG. 8) with $k_{cat}/K_M$s 1.5- to 2-fold lower than WT. Despite its steric bulk and high hydrophilicity, disaccharidic lacto-CMM N62C-S-f (See FIG. 8) also showed higher activity than N62C with $k_{cat}/K_M$ only 1.7-fold lower than WT.

The effects of the mutation of position 217 in the $S_1'$ pocket were intrinsically more dramatic as indicated by a value of $k_{cat}/K_M$ for L217C that is 4-fold lower than WT (FIG. 10B). The introduction of deprotected untethered glucose. forming L217C-S-β-Glc, lowered $k_{cat}/K_M$ further to 6-fold lower than WT. In contrast, glycosylation of position 217 with ethyl tethered MTS reagents 1b–f (See FIG. 8) restored activity and $k_{cat}/K_M$s for L217C-S-b-f (See FIG. 8) were similar to each other in the range 2.5- to 3.1-fold lower than WT. This striking difference between tethered L217C-S-b-f (See FIG. 8) and untethered L217C-S-β-Glc illustrated that SBL tolerates the replacement of hydrophobic Leu with highly hydrophilic carbohydrate moieties when they are linked by a hydrophobic ethyl spacer group better than directly-linked Cys-S-β-Glc. This may indicate that a structural requirement for efficient amidase activity is a closely-bound hydrophobic residue in the $S_1'$ subsite of SBL and contrasts sharply with the excellent enhancement of esterase activity caused by the same Cys-S-β-Glc substitution.

Mutation of position 156 in the $S_1$ pocket to cysteine caused a 1.4-fold drop in $k_{cat}/K_M$ (FIG. 10C). Subsequent introduction of deprotected S-Et-α-Glc, side chain b (See FIG. 8), resulted in a $k_{cat}/K_M$ for S156C-S-b (See FIG. 8) that was 2.3-fold lower than WT. From S156C-S-b to -f (See FIG. 8), kc,K$_s$/s varied in an arced manner peaking at 1.9-fold lower than WT for S156C-S-d (See FIG. 8) and then decreasing monotonically to a k$_{cat}$/K$_M$ for S156C-S-f (See FIG. 8) that was 3-fold lower than WT. The similar K$_M$ values for these S156 CMMs to those of SBL-WT were indicative of these modifications having little effect upon ground state binding and were consistent with the surface exposed orientation of the S156 side chain.

At position 166, in the S$_1$ pocket, the 2.5-fold decrease in k$_{cat}$/K$_M$ caused by mutation to cysteine was amplified by modification with 1b (See FIG. 8) and led to a k$_{cat}$/K$_M$ value 3-fold lower than WT for S166C-S-b (See FIGS. 8 and 10D). From S166C-S-b to -f (See FIG. 8), k$_{cat}$/K$_M$ decreased monotonically to a k$_{cat}$/K$_M$ for S166C-S-f (See FIG. 8), in which the S$_1$ binding site was occupied by the sterically bulky disaccharide lactose, that was 3.8-fold lower than WT.

Example 11
Kinetic Effects of Glycosylation with Acetylated Carbohydrates.

The enormous potential of the controlled site-selective glycosylation approach depicted in FIG. 8 was illustrated by the great variety of changes in k$_{cat}$/K$_M$ that were caused by the introduction of acetylated side chains a,g-k (See FIG. 8) to SBL. These dramatic changes contrast with the slight variations found for deprotected side chains b–f (See FIG. 8). For example, at position 62, an alternating decrease-increase pattern was observed (FIG. 11A). This resulted in a k$_{cat}$/K$_M$ for tetraacetylated α-gluco-CMM N62C-S-g (See FIG. 8) that was 1.1-fold higher than WT. Similar alternating patterns were also seen at positions 217 (FIG. 11B) and 166 (FIG. 11D). At position 156, variations were slight, which was consistent with its surface exposed orientation (FIG. 11C).

To examine the cause of these variations, the k$_{cat}$/K$_M$s of acetylated glycosylated CMMs were compared with those for deprotected glycosylated CMMs with the same glycan structure and stereochemistry (FIG. 12). This separated the effects of acetylation from the effects of glycosylation and allowed the underlying effects of modification to be dissected. It was clear from FIG. 12 that the anomeric stereochemistry of the acetylated glycans modulates k$_{cat}$/K$_M$.

For example, at position 62 (FIG. 12A) comparison of N62C-S-b,c (See FIG. 8) with N62C-S-g (See FIG. 8) and N62C-S-Et-β-Glc(Ac)$_{2,3}$ showed that increasing the number of acetate groups from zero to four, from N62C-S-b (See FIG. 8) to N62C-S-d (See FIG. 8), increased k$_{cat}$/K$_M$ 1.6-fold for the c-gluco side-chain b (See FIG. 8). In contrast, increasing the number from zero to two or three, from N62C-S-c to N62C-S-Et-β-Glc(Ac)$_{2O3}$, was detrimental for the β-gluco side-chain c (See FIG. 8) and led to a 2-fold decrease. Similarly, N62C-S-Et-β-Gal(Ac)$_3$ displayed a distinctly lower k$_{cat}$/K$_M$ than N62C-S-e (See FIG. 8) that was 5-fold lower than WT. These changes in k$_{cat}$/K$_M$ upon acetylation were manifested largely through increased or decreased ground state binding, of which the most striking example was a K$_M$ for N62C-S-Et-β-Gal(Ac)$_3$ that was 2.4-fold higher than deprotected galacto-CMM N62C-S-e (See FIG. 8).

At position 217, control of the level of acetylation through pH, as shown in FIG. 9, had allowed the introduction at position 217 of untethered β-D-glucose bearing zero, two, and three acetate groups. As FIG. 12B illustrates, the addition of two or three acetate groups restored k$_{cat}$/K$_M$ from 6-fold lower than WT for L217C-S-β-Glc to 2-fold lower than WT for L217C-S-β-Glc(Ac)$_2$ or L217C-S-β-Glc(Ac)$_3$. This showed that acetylation allowed fine-tuning of activity and paralleled increases in the esterase k$_{cat}$/K$_M$s of these CMMs.

The same trend in k$_{cat}$/K$_M$ was observed for the L217C ethyl tethered CMMs as at position 62: acetylation was beneficial to x-tethered but detrimental to β-tethered CMMs. For example, increasing the number of acetate groups in the a-linked glucose moiety from zero to two, i.e., from L217C-S-b (See FIG. 8) to L217C-S-Et-α-Glc(Ac)$_2$, increased k$_{cat}$/K$_M$ to 2-fold lower than WT. In contrast, increasing the number of acetate groups in the epimeric β-linked moiety from zero to three, i.e., from L217C-S-c (See FIG. 8) to L217C-S-Et-β-Glc(Ac)$_3$, halved k$_{cat}$/K$_M$ to 6-fold lower than WT. Similarly, the k$_{cat}$/K$_M$ of α-linked L217C-S-Et-α-Man(Ac)$_3$ was 1.5-fold higher than the corresponding deprotected L217C-S-d (See FIG. 8), while β-linked L217C-S-Et-β-Gal(Ac)$_3$ was 2-fold lower than the corresponding deprotected L217C-S-e (See FIG. 8).

Consistent with its surface exposed orientation, the changes at position 156 caused by acetylation were slight and no variation with anomeric stereochemistry was seen (FIG. 12C). Increasing the number of acetate groups from zero to four, from S156C-S-b-e (See FIG. 8) to S156C-S-g-j (See FIG. 8), decreased k$_{cat}$/K$_M$ by 1.05- to 1.6-fold. The most sterically bulky lactose side chain (-k) (See FIG. 8) gave rise to the lowest k$_{cat}$/L$_M$ at position 156, 3.2-fold lower than WT, and indicated that even at the surface of SBL the introduction of sterically bulky groups still allowed tailoring of k$_{cat}$/K$_M$.

At position 166, the effects of increased acetylation were, as at positions 62 and 217, modulated by glycan anomeric configuration (FIG. 12D). However, the direction of these increases and decreases was reversed: acetylation was beneficial to β-tethered but detrimental to α-tethered CMMs. For example, the α-tethered S166C-S-Et-α-Glc(Ac)$_3$ had a 1.8-fold lower k$_{cat}$/K$_M$ value than the corresponding deprotected S166C-S-b (See FIG. 8), while 1-linked CMMs S166-S-Et-β-Glc(Ac)$_{23}$ had 1.6-fold higher k$_{cat}$/K$_M$ values than the corresponding fully deprotected S166-S-c (See FIG. 8). Again, these variations were largely manifested through changes in ground state binding. For example, K$_M$ increased 1.4-fold from S5166C-S-Et-α-Man (-d) (See FIG. 8) to S166C-S-Et-α-Man(Ac)$_3$.

It should be noted that the changes in activity of the lacto-CMMs upon acetylation fell largely outside of these trends and at all four positions acetylation of the bulky, disaccharidic side-chain f (See FIG. 8) caused a general decrease in k$_{cat}$/K$_M$s. For example, at position 62 heptaacetylation, from N62C-S-f (See FIG. 8) to N62C-S-k (See FIG. 8), resulted in a lowering of k$_{cat}$/K$_M$ to a value that is 3-fold lower than WT. Despite the greater steric bulk of side chain k (See FIG. 8), this drop was a consequence of a lower k$_{cat}$, 2-fold lower than N62C-f (See FIG. 8), rather than a higher K$_M$. In fact, the K$_M$ value of N62C-S-k (See FIG. 8) was 1.3-fold lower than N62C-S-f (See FIG. 8). Similarly, L217C-S-Et-Lac(Ac)$_6$ and S166C-S-Et-Lac(Ac)$_5$ had 1.7-fold and 1.4-fold lower k$_{cat}$/K$_M$s than the corresponding deprotected CMMs, respectively.

In summary, the strategy of site-directed mutagenesis combined with chemical modification was exploited for the site-selective glycosylation of SBL. This method was general, versatile and allowed the preparation of pure glycoforms which constitute the first examples of regio- and glycan- specific protein glycosylation at predetermined sites. Careful control of a novel SBL-catalyzed intramolecular deacetylation greatly expanded the scope of this method and through reaction of SBL-N62C, -S156C, -S166C, and -L217C with peracetylated MTS reagents 1a,g–k (See FIG. 8) allowed the introduction of glycans with precisely modulated levels of acetylation.

The glycosylated CMMs formed display $k_{cat}/K_M$ values that ranged from 1.1 -fold higher than WT to 7-fold lower than WT. Without the use of this highly selective glycosylation technique, the determination of such precise trends would be unachievable and variations caused by previous non-specific glycosylation could only be interpreted in a general manner. It has been demonstrated that subtle differences in carbohydrate structure may be used to fine tune the activity of SBL. For example, the anomeric stereochemistry of the glycans introduced modulated changes in $k_{cat}/K_M$ upon acetylation. At positions 62 and 217, acetylation enhanced the activity of α-tethered CMMs but decreased that of β-tethered. This trend was reversed at position 166 where, in contrast, acetylation enhanced the $k_{cat}/K_M$s of β-tethered CMMs but decreased those of α-tethered. Consistent with its surface exposed nature, changes at position 156 were more modest, but still allowed control of activity particularly through glycosylation with disaccharide lactose. These results illustrated the great potential for tailoring activity through the correct choice of glycan and glycosylation site.

The ability of the glycosylation method to glycosylate the binding pockets of SBL also creates opportunities to broaden its substrate specificity. For instance, an array of hydrogen bonding hydroxyl groups may broaden its specificity towards hydrogen bonding substrates such as glycosylated amino acids. Subtilisins have been elegantly used to catalyze the synthesis of glycopeptides (Witte et al., "Solution- and Solid-Phase Synthesis of N-protected Glycopeptide Esters of the Benzyl Type as Substrates for Subtilisin-Catalyzed Glycopeptide Couplings," *J. Am. Chem. Soc.* 120:1979–1989 (1998); Wong et al., "Enzymatic-Synthesis of N-Linked and O-Linked Glycopeptides," *J. Am. Chem. Soc.* 115:5893–5901 (1993), which are hereby incorporated by reference). However, the natural specificity of these enzymes has limited these peptide ligations to those in which the glycosylated residues are at least one residue distant ($P_2$, $P_3$ . . . or $P_2'$, $P_3'$ . . . ) from the amide bond formed. For example, while ligation of Z-Gly-OBz with H-Gly-Ser(Ac$_3$GlcNAcβ)-NH$_2$ was successful, no yield of product was obtained with H-Ser(Ac$_3$GlcNAcβ)-NH$_2$ (Witte et al., *J. Am. Chem. Soc.*, 120:1979–1989 (1998), which is hereby incorporated by reference). The introduction of sugars to the $S_1$ and $S_1'$ subsites as hydrogen bonding groups demonstrated here may enhance the specificity of proteases towards hydrophilic substrates.

Furthermore, by choosing carbohydrate attachments that differ from each other at only one stereocenter, SARs may be determined by examining changes in activity as the nature of sugar side chain is varied. For example, the effect of inverting stereocenters in the order C-4→C-1→C-2 can be determined using CMMs in the series e→c→b→d (See FIG. 8). While the current illustrations have been with SBL as a protein example, the method is clearly amenable to the glycosylation of any protein and is without limitation with respect to the sites and to the glycans that may be conjugated. It will, therefore, allow the introduction of any therapeutically important carbohydrate recognition determinant, of which the β-D-galactopyranosyl moiety of e and f (See FIG. 8) that represents a ligand of the hepatic asialoglycoprotein receptor (Sharon et al., *Essays Biochem.*, 30:59–75 (1995), which is hereby incorporated by reference) is just one example.

Example 12

Esterase Screen

Specificity constants determined using the low substrate approximation were measured indirectly using Ellman's reagent (Ellman et al., *Biochem. Pharmacol.*, 7:88–95 (1961), which is hereby incorporated by reference) ($\epsilon_{412}$= 13600 M$^{-1}$cm$^{-1}$) using 0.15 and 0.30 mM succinyl-AAPF-SBn as substrate in 0.1 M Tris.HCl, containing 0.005 vol % DMSO, 1 vol % 37.5 mM Ellman's reagent in DMSO, pH 8.6.

Example 13

Full Esterase Kinetics Measurements

Michaelis-Menten constants were measured at 25° C. by curve fitting (Grafit® 3.03, Erithacus Software Ltd., Staines, Middlesex, UK) of the initial rate data determined at eight concentrations (31.25 µM–3 mM) of the succinyl-AAPF-SBn substrate, followed indirectly using Ellman's reagent in 0.1 M Tris.HCl, containing 0.005 vol % DMSO, 1 vol % 37.5 mM Ellman's reagent in DMSO, pH 8.6.

Example 14

Esterase Activity Screen

The glyco-CMMs shown in Table 4 were prepared, by reacting reagents 1a–k (See FIG. 8) with the chosen cysteine mutants SBL-N62C, -S156C, -S166C and -L217C, purified and extensively characterized as described previously.

TABLE 4

Esterase Screen Results for Glycosylated CMMs[a]

| | N62C-R | | L217C-R | | S166C-R | | S156C-R | |
|---|---|---|---|---|---|---|---|---|
| -R | $k_{cat}/K_M$ (s$^{-1}$ mM$^{-1}$) | E/A[b] | $k_{cat}/K_M$ (s$^{-1}$ mM$^{-1}$) | E/A[b] | $k_{cat}/K_M$ (s$^{-1}$ mM$^{-1}$) | E/A[b] | $k_{cat}/K_M$ (s$^{-1}$ mM$^{-1}$) | E/A[b] |
| H | 4380 | 48 | 5540 | 109 | 350 | 4 | — | — |
| -SβGlc | — | — | 6350 | 186 | — | — | — | — |
| B | 5327 | 37 | 7773 | 90 | 2688 | 37 | 1984 | 22 |
| C | 6625 | 62 | 9791 | 130 | 2732 | 40 | 2197 | 21 |
| D | 4627 | 36 | 8651 | 77 | 2924 | 45 | 2648 | 24 |
| E | 5729 | 48 | 11923 | 163 | 3241 | 56 | 2505 | 28 |
| F | 5990 | 48 | 9080 | 137 | 2511 | 44 | 1692 | 24 |
| -SβGlc(Ac)$_2$ | — | — | 8776 | 86 | — | — | — | — |
| -SβGlc(Ac)$_3$ | — | — | 11642 | 115 | — | — | — | — |
| -SβGlc(Ac)$_4$ (-a) | 2502 | 19 | — | — | 2537 | 50 | 1356 | 17 |
| -SetαGlc(Ac)$_2$ | — | — | 7893 | 79 | — | — | — | — |
| -SetαGlc(Ac)$_3$ | — | — | — | — | 1829 | 45 | — | — |

TABLE 4-continued

Esterase Screen Results for Glycosylated CMMs[a]

| | N62C-R | | L217C-R | | S166C-R | | S156C-R | |
|---|---|---|---|---|---|---|---|---|
| -R | $k_{cat}/K_M$ ($s^{-1}$ $mM^{-1}$) | E/A[b] | $k_{cat}/K_M$ ($s^{-1}$ $mM^{-1}$) | E/A[b] | $k_{cat}/K_M$ ($s^{-1}$ $mM^{-1}$) | E/A[b] | $k_{cat}/K_M$ ($s^{-1}$ $mM^{-1}$) | E/A[b] |
| -SetαGlc(Ac)$_4$ (-g) | 6851 | 30 | — | — | — | — | 1887 | 34 |
| -SetβGlc(Ac)$_2$ | 1925 | 36 | — | — | 5058 | 46 | — | — |
| -SetβGlc(Ac)$_3$ | 2736 | 51 | 4935 | 156 | 6033 | 54 | — | — |
| -SetβGlc(Ac)$_4$ (-h) | — | — | — | — | — | — | 2321 | 26 |
| -SetαMan(Ac)$_3$ | — | — | 11751 | 71 | 1537 | 37 | — | — |
| -SetαMan(Ac)$_4$ (-i) | 5807 | 50 | — | — | — | — | 2629 | 31 |
| -SetβGal(Ac)$_3$ | 2169 | 50 | 3889 | 116 | 3159 | 38 | — | — |
| -SetβGal(Ac)$_4$ (-j) | — | — | — | — | — | — | 2010 | 24 |
| -SetLac(Ac)$_5$ | — | — | — | — | 1543 | 38 | — | — |
| -SetLac(Ac)$_6$ | — | — | 5468 | 139 | — | — | — | — |
| -SetLac(Ac)$_7$ (-k) | 2135 | 29 | — | — | — | — | 1516 | 22 |

[a]Kinetic constants determined in duplicate using the low substrate concentration approximation in 0.1M Tris buffer. pH 8.6 0.005% Tween 80. 1% DMSO with suc-AAPF-SBn as substrate. [S] = 15 or 30 μM. [E] = 4.8 × 10$^{-11}$ to 6.0 × 10$^{-10}$M.
[b]E/A = $(k_{cat}/K_M)_{esterase}/(k_{cat}/K_M)_{amidase}$.
[c]For SBL-WT: $k_{cat}/K_M$ = 3592.5 mM$^{-1}$ s$^{-1}$. E/A = 17.

The kinetic parameters of esterase activity were determined at pH 8.6 by indirectly following the release of thiobenzyl alcohol from the substrate succinyl-Ala-Ala-Pro-Phe-SBn (suc-AAPF-SBn) with Ellman's reagent (Ellman et al., *Biochem. Pharmacol.*, 7:88–95 (1961), which is hereby incorporated by reference). To allow a rapid screen of esterase activity, a low substrate concentration ([S]<<$K_M$) was used that allowed $k_{cat}/K_M$ to be determined directly from the initial rate of reaction. The results from the screen are shown in Table 4.

Figure 13:
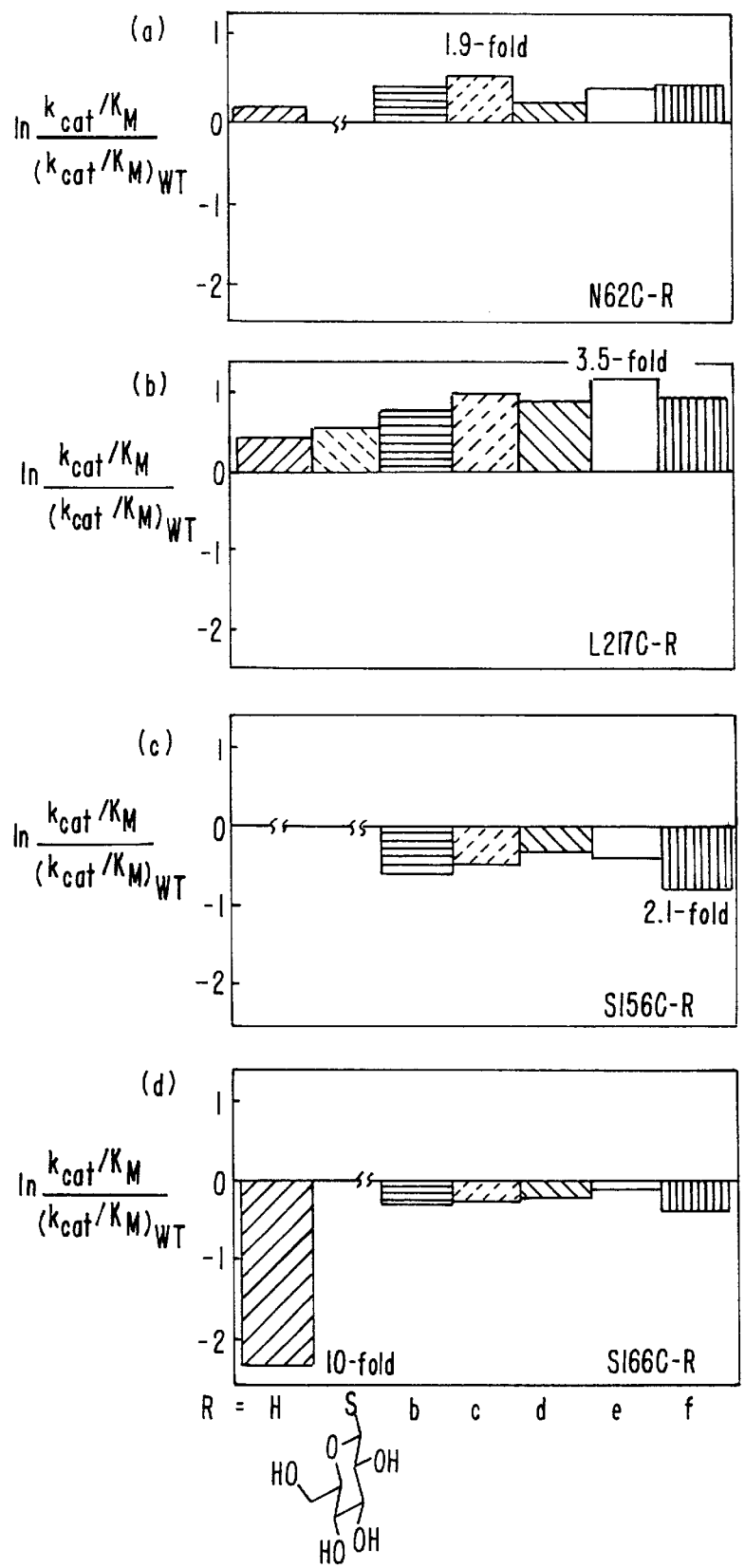

Modification at position 62, in the S$_2$ pocket, with deprotected sugar reagents 1*b–f* (See FIG. 8) increased $k_{cat}/K_M$, resulting in a series of five enzymes that had similar $k_{cat}/K_M$s that were 1.3- to 1.9-fold greater than WT (FIG. 13A). The presence of an α-linkage was clearly deleterious to activity, as N62C-SEtβGlc (-c) (See FIG. 8) had a $k_{cat}/K_M$ 1.2-fold greater than its epimer N62C-SEtαGlc (-b) (See FIG. 8) and 1.9-fold greater than WT. Furthermore, the α-linked N62C-SEtαMan (-d) (See FIG. 8) had the lowest $k_{cat}/K_M$ in this group which was 1.3-fold greater than WT.

As at position 62, the introduction of any of the deprotected sugar side chains b–f (See FIG. 8) at position 217, in the S$_1$' pocket increased $k_{cat}/K_M$ (FIG. 13B). However, the effects of glycosylation at this site were far more dramatic as demonstrated by a $k_{cat}/K_M$ for L217C-SEtβGal (-e) (See FIG. 8) that was 3.4-fold greater than WT. By comparing the $k_{cat}/K_M$s of L217C-SβGlc and L217C-SEtβGlc (-c) (See FIG. 8), it was possible to gauge the effect on activity of introducing an ethyl tether at this position. This introduction increased $k_{cat}/K_M$, from 1.8-fold greater than WT for L217C-SβGlc to 2.7-fold greater than WT for L217C-SEtβGlc (-c) (See FIG. 8). As at position 62, β-linked glyco-CMMs (-c, -e, -f) (See FIG. 8) had higher $k_{cat}/K_M$s than the α-linked ones (-a, -d) (See FIG. 8). For example, L217C-SEtβGlc (-c) (See FIG. 8) had a $k_{cat}/K_M$ 1.3-fold greater than L217C-SEtαGlc (-b) (See FIG. 8).

Consistent with the surface exposed orientation of the S156 side chain, the S156C deprotected glyco-CMMs had similar $k_{cat}/K_M$s that were 1.3- to 2.1-fold lower than WT (FIG. 13C).

At position 166, in the S$_1$ pocket, mutation to cysteine resulted in an enzyme with a severely lowered $k_{cat}/K_M$ that was 10-fold lower than WT. However, subsequent modification with 1*b–f* (See FIG. 8) restored much of the catalytic activity (FIG. 13D), and the S166C deprotected glyco-CMMs S166C-S-b-f (See FIG. 8) had similar $k_{cat}/K_M$s, that varied from 1.1- to 1.4-fold lower than WT.

Example 15

Kinetic Effects of Glycosylation with Acetylated Carbohydrates.

Figure 14:
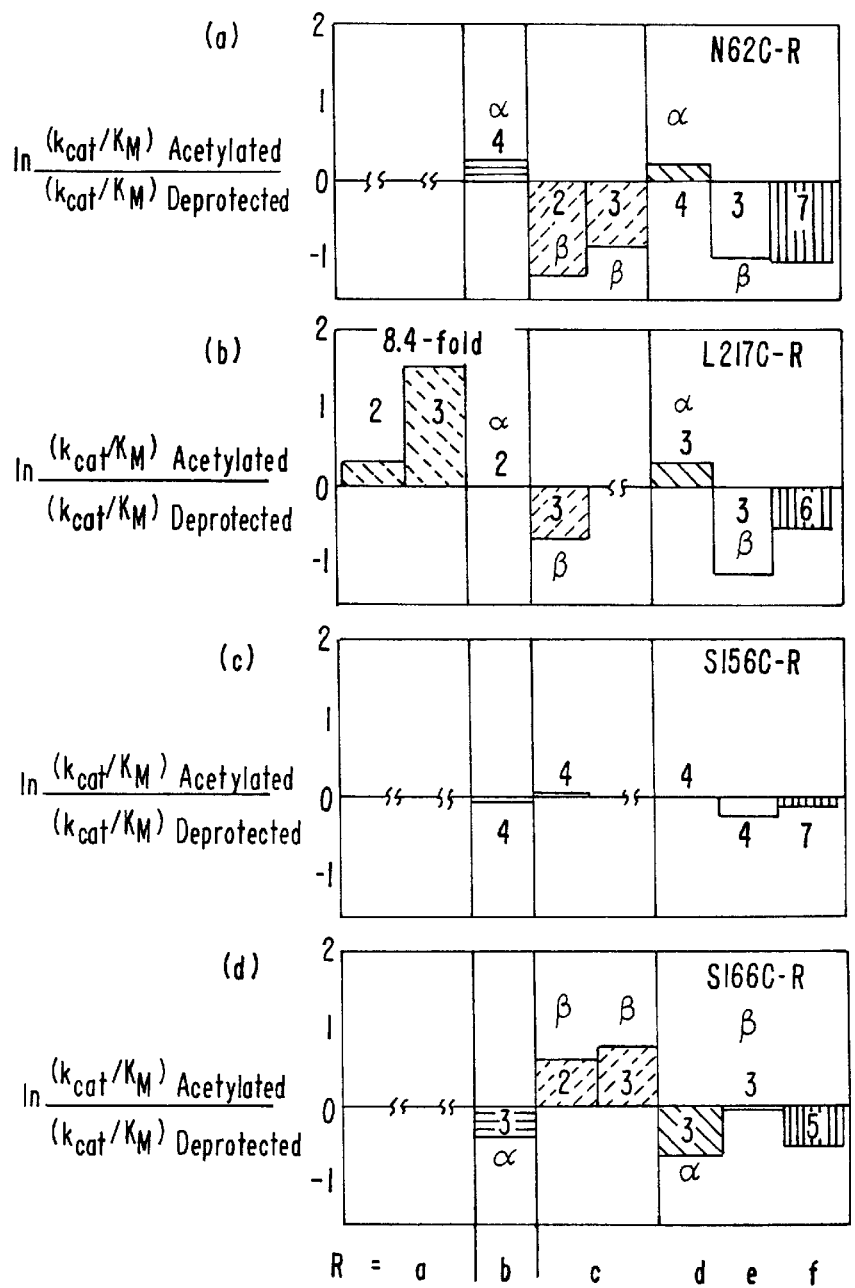
Figure 14:
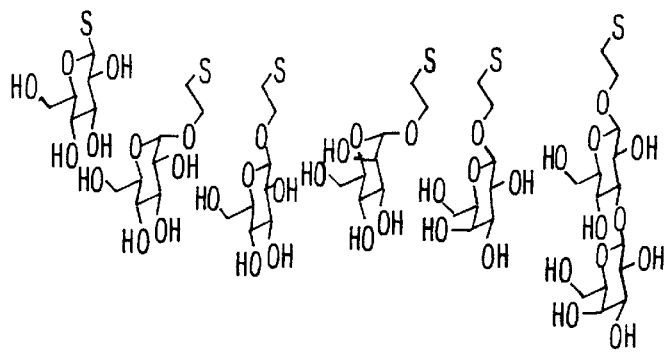

At position 62, in the S2 pocket, in sharp contrast to the trend observed for the unacetylated N62C CMMs, acetylated N62C CMMs had a wide range of $k_{cat}/K_M$s. Introduction of acetates increased the $k_{cat}/K_M$s of the α-linked CMMs relative to the corresponding deprotected glyco-CMMs (FIG. 14A). Thus, N62C-SEtαGlc(Ac)$_4$ (-b) (See FIG. 8) and N62C-SEtαMan(Ac)$_4$ (-d) (See FIG. 8) had $k_{cat}/K_M$s 1.9- and 1.6-fold greater than WT, respectively. Acetylation was clearly deleterious for β-linked CMMs, as N62C-SEtβGal(Ac)$_3$, N62C-SEtβGlc(Ac)$_2$, and N62C-SEtβGlc(Ac)$_3$ all had $k_{cat}/K_M$s lower than WT. However, increasing the number of acetates present on the CMM restored activity: N62C-SEtβGlc(Ac)$_3$ had a $k_{cat}/K_M$ only 1.3-fold lower than WT and 1.5-fold higher than N62C-SEtβGlc(Ac)$_2$. In spite of their size, the sterically bulky side chain lactosylated N62C CMMs, N62C-SEtLac (-f) (See FIG. 8) and N62C-SEtLac(Ac)$_7$ (-k) (See FIG. 8) had $k_{cat}/K_M$s that were similar to those of the CMMs derived from monosaccharides. This provided a clear example of the versatility of the glycosylation method illustrated in FIG. 8 and demonstrated that by using this method it was possible to introduce very large structures into the active site of SBL while maintaining catalytic competency.

Modification with acetylated reagents 1*a,g–k* (See FIG. 8) at position 217, in the S$_1$' pocket, as with 1*b–k* (See FIG. 8), led to CMMs with greater than WT $k_{cat}/K_M$s (FIG. 14B). For the untethered glyco-CMMs, increasing the number of acetates dramatically increased $k_{cat}/K_M$, from 1.8-fold greater than WT for L217C-SβGlc to 2.4-fold greater than WT for L217C-SβGlc(Ac)$_2$ and to 3.2-fold greater than WT for L217C-SβGlc(Ac)$_3$ and mirrored the trend seen in amidase kinetics. For the ethyl linked L217C glyco-CMMs, the effect of acetylation was dependent on the anomeric stereochemistry, as observed for N62C glyco-CMMs and the L217C glyco-CMMs amidase kinetics. Acetylation of α-linked CMMs increased $k_{cat}/K_M$ but decreased $k_{cat}/K_M$ for β-linked CMMs. This was most pronounced for L217C-SEtβGal(Ac)$_3$ which had a $k_{cat}/K_M$ only 1.1-fold greater than WT and 3.1-fold lower than L217C-SEtβGal (-e). In contrast to the effect on deprotected L217C glyco-CMMs, the activity of acetylated L217C glyco-CMMs decreased upon the introduction of the ethyl linker. For example, L217C-SβGlc(Ac)$_3$ had a $k_{cat}/K_M$ 3.2-fold greater than WT, as compared with the 1.4-fold greater than WT $k_{cat}/K_M$ of L217C-SEtβGlc(Ac)$_3$.

At position 156, in the S$_1$ pocket, the S156C acetylated glyco-CMMs displayed little difference in their kinetic constants from their unacetylated counterparts (FIG. 14C), an observation that was consistent with the surface exposed nature of the position 156 side chain. Introducing the ethyl linker led to an increase in $k_{cat}/K_M$ from 2.6-fold lower than WT for S156C-SβGlc(Ac)$_4$ (-a) (See FIG. 8) to 1.5-fold lower than WT for S156C-SEtβGlc(Ac)$_4$ (-h) (See FIG. 8).

In general, at position 166, in the S$_1$ pocket, the effect of acetylation on S166C ethyl linked glyco-CMMs was to reduce $k_{cat}/K_M$s relative to their deprotected counterparts (FIG. 14D). The exceptions were the ethyl linked β-gluco-CMMs, S166C-SEtβGlc(Ac)$_2$ and S166C-SEtβGlc(Ac)$_3$, which displayed $k_{cat}/K_M$s 1.4- and 1.7-fold greater than WT, respectively. These were the only two glyco-CMMs prepared at this site to show an enhancement in $k_{cat}/K_M$ relative to WT, and this example illustrates that the correct selection of sugar is crucial to the tailoring of enzyme activity. In contrast to the effects observed at positions 62 and 217, an α-linkage to the sugar moiety was deleterious to the activity of the acetylated CMMs and S166C-SEtαGlc(Ac)$_3$ had a $k_{cat}/K_M$ 1.9-fold lower than WT, in direct contrast to S166C-SEtβGlc(Ac)$_3$. Introduction of the sterically bulky lactose moiety, in both acetylated and unacetylated forms, led to CMMs S166C-SEtLac (-f) (See FIG. 8) and S166C-SEtLac (Ac)$_5$ with low $k_{cat}/K_M$s that were 1.4- and 2.3-fold lower than WT, respectively.

Example 16
Full Esterase Kinetics.

The three esterases with the highest $k_{cat}/K_M$s determined by the above screen, L217C-SβGlc(Ac)$_3$, L217C-SEtαMan(Ac)$_3$, and L217C-SEtβGal (-e) (See FIG. 8) had their individual $k_{cat}$s and $K_M$s determined by the initial rates method. The results are shown in Table 5.

TABLE 5

Full Esterase Kinetic Data for Glycosylated CMMs[a]

| Enzyme | $k_{cat\ (s^{-1})}$ | $K_M$ (mM) | $k_{cat}/K_M$ (mM$^{-1}$ s$^{-1}$) | xWT | E/A[b] |
|---|---|---|---|---|---|
| WT | 1940.0 ± 180 | 0.54 ± 0.07 | 3592.5 ± 572.11 | 1 | 17 |
| L217C-SβGlc(Ac)$_3$ | 4427.5 ± 100.9 | 0.15 ± 0.01 | 29516.7 ± 2079.0 | 8.4 | 293 |
| L217C-SEtαMan(Ac)$_3$ | 3827.0 ± 59.5 | 0.30 ± 0.01 | 12756.7 ± 469.2 | 3.6 | 77 |

TABLE 5-continued

Full Esterase Kinetic Data for Glycosylated CMMs[a]

| Enzyme | $k_{cat\ (s^{-1})}$ | $K_M$ (mM) | $k_{cat}/K_M$ (mM$^{-1}$ s$^{-1}$) | xWT | E/A[b] |
|---|---|---|---|---|---|
| L217C-SetβGal | 4398.5 ± 189.8 | 0.36 ± 0.04 | 12218.1 ± 1456.3 | 3.5 | 167 |

[a]Kinetic constants determined by method of initial rates in 0.1M Tris buffer, pH 8.6, 0.005% Tween 80, 1% DMSO with suc-AAPF-SBn as substrate. [S] = 30 μM to 2 mM, [E] = 9.6 × 10$^{-11}$ to 1.1 × 10$^{-10}$ M.
[b]E/A = ($k_{cat}/K_M$)$_{estelase}$/($k_{cat}/K_M$)$_{amidase}$.

The results were in good agreement with those determined by the screen for L217C-SEtαMan(Ac)$_3$ and L217C-SEtβGal (-e) (See FIG. 8) and confirmed the activity of these two enzymes to be 3.6- and 3.5- fold higher than WT, respectively. These increases in activity arose from both increased transition state stabilization, with $k_{cat}$s 2- and 2.3-fold greater than WT, respectively, and from greater substrate binding, with $K_M$s 1.8- and 1.5-fold lower than WT, respectively.

Remarkable results were obtained for L217C-SβGlc(Ac)$_3$. This enzyme had a $k_{cat}$ 2.3-fold greater than WT and a $K_M$ 3.6-fold lower than WT, giving a $k_{cat}/K_M$ 8.4-fold greater than WT and some 2.5-fold greater than the value estimated by the screen. The difference in parameters obtained from the screen and the full kinetic analysis exposed a limitation of the low substrate screen. For the low substrate approximation to be accurate, the substrate concentration must be small compared to $K_M$. The $K_M$ of L217C-SβGlc(Ac)$_3$ (0.15 mM) was evidently so small that the approximation did not hold in this case. This was the largest enhancement of activity relative to WT achieved using the combined site-directed mutagenesis and chemical modification strategy.

Example 17
Esterase Activity versus Amidase Activity.

Figure 15:
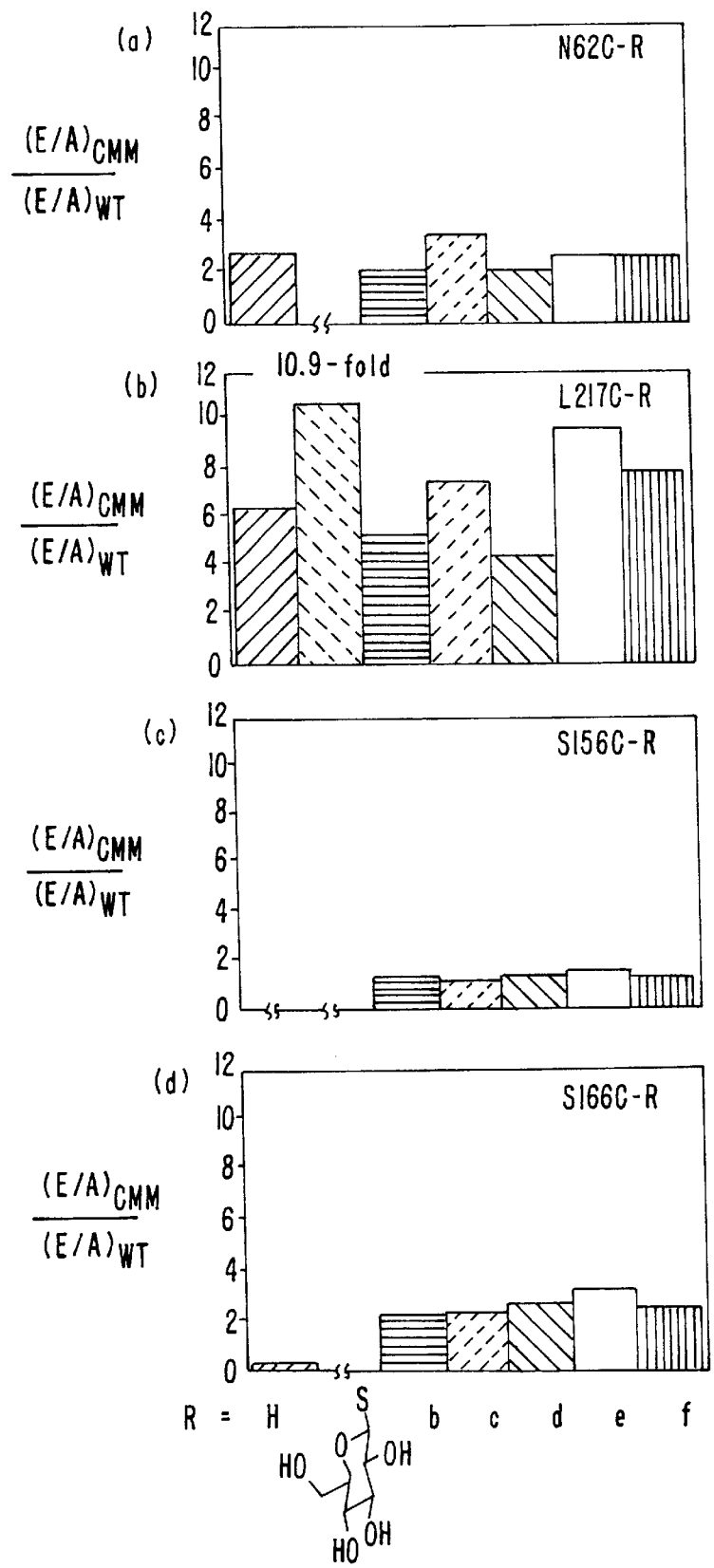
Figure 16:
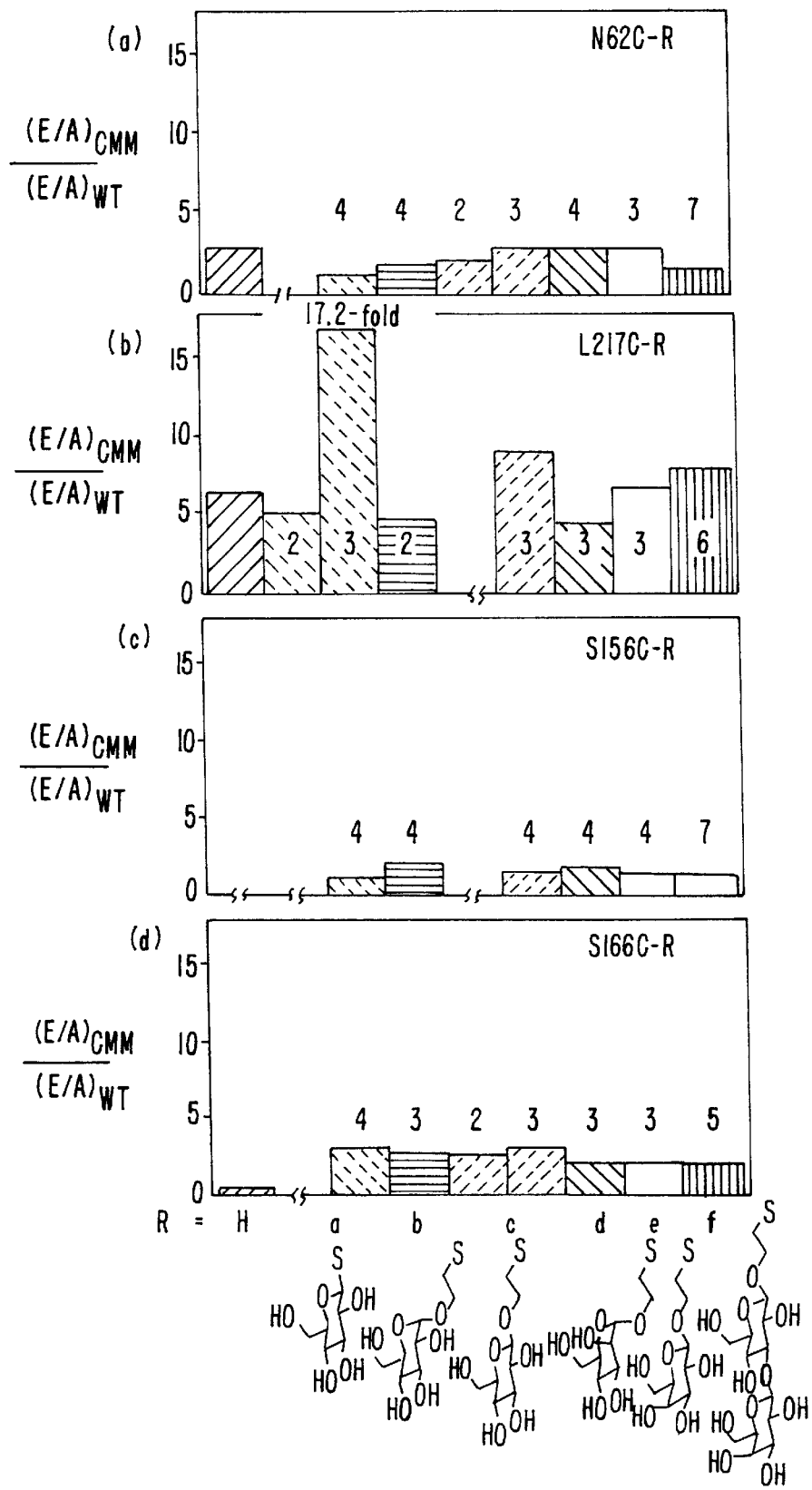
Figure 17:
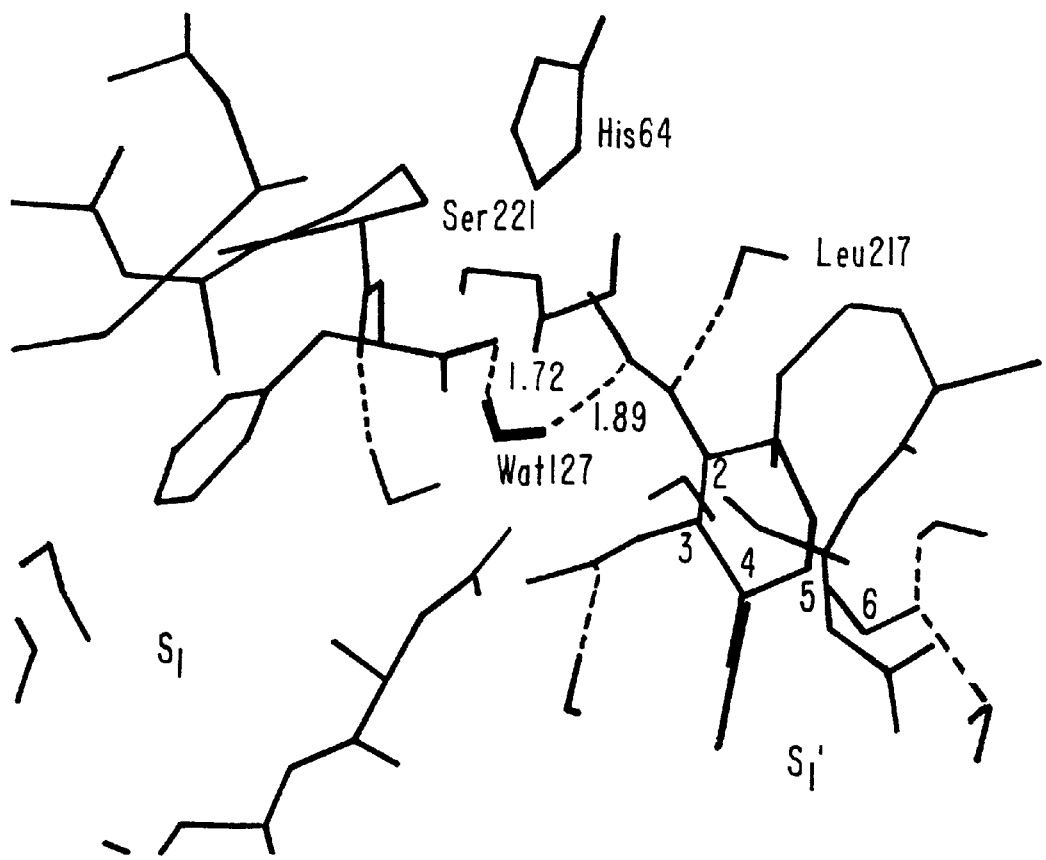

The differing effects of glycosylation upon amidase and esterase $k_{cat}/K_M$ can be compared in an informative manner using the ($k_{cat}/K_M$)$_{esteiase}$/($k_{cat}/K_M$)$_{amidase}$ ratio, E/A (see FIG. 15).

All N62C deprotected glyco-CMMs had E/As that were enhanced relative to WT. The increase in E/A was dependent on the presence of either an α- or a β-linkage with the β-linked CMMs N62C-SEtβGlc (-c) (See FIG. 8), -SEtβGal (-e) (See FIG. 8), -SEtLac (-f) (See FIG. 8) having higher E/As than the α-linked CMMs N62C-SEtαGlc (-b) (See FIG. 8) and -SEtαMan (-d) (See FIG. 8) (FIG. 15A). These increased ratios were due to both increases in esterase $k_{cat}/K_M$s and reductions in amidase $k_{cat}/K_M$s.

As observed for the modifications made at position 62, glycosylation at position 217, in the S$_1$' pocket, led to enzymes that had greatly increased E/A ratios relative to WT. Mutation to cysteine at position 217 increased E/A to 6.4-fold greater than WT. Modification with unacetylated β-linked sugars -SβGlc, -SEtβGlc (-c) (See FIG. 8), -SEtβGal (-e) (See FIG. 8), -SEtLac (-f) (See FIG. 8) further increased E/A (FIG. 15B). In contrast, α-linked glyco-CMMs had lower E/A values than that of the mutant. These changes in E/As were a result of parallel changes in esterase $k_{cat}/K_M$s that were further amplified by opposing changes in amidase $k_{cat}/K_M$s Introduction of an ethyl linker reduced the E/A from 10.9-fold greater than WT for L217C-SβGlc to 7.6-fold greater than WT for L217C-SEtβGlc (-c) (See FIG. 8).

At position 156, in the $S_1$ pocket, E/A ratios for unacetylated glyco-CMMs were all similar to each other in the range 1.2- to 1.6-fold greater than WT (FIG. 15C).

The mutant S166C had an exceptionally low E/A that was 4.2-fold lower than WT (FIG. 15D) and this was largely a result of its very low esterase $k_{cat}/K_M$. Because modification of S166C restored esterase $k_{cat}/K_M$s to levels approaching that of WT and because S166C glyco-CMMs were poor amidases relative to WT, the net result was a family of CMMs with similar E/A ratios that were all enhanced relative to WT and significantly higher than the cysteine mutant (FIG. 15D).

Example 18

Effects of Glycosylation with Acetylated Carbohydrates on E/A.

Figure 18:
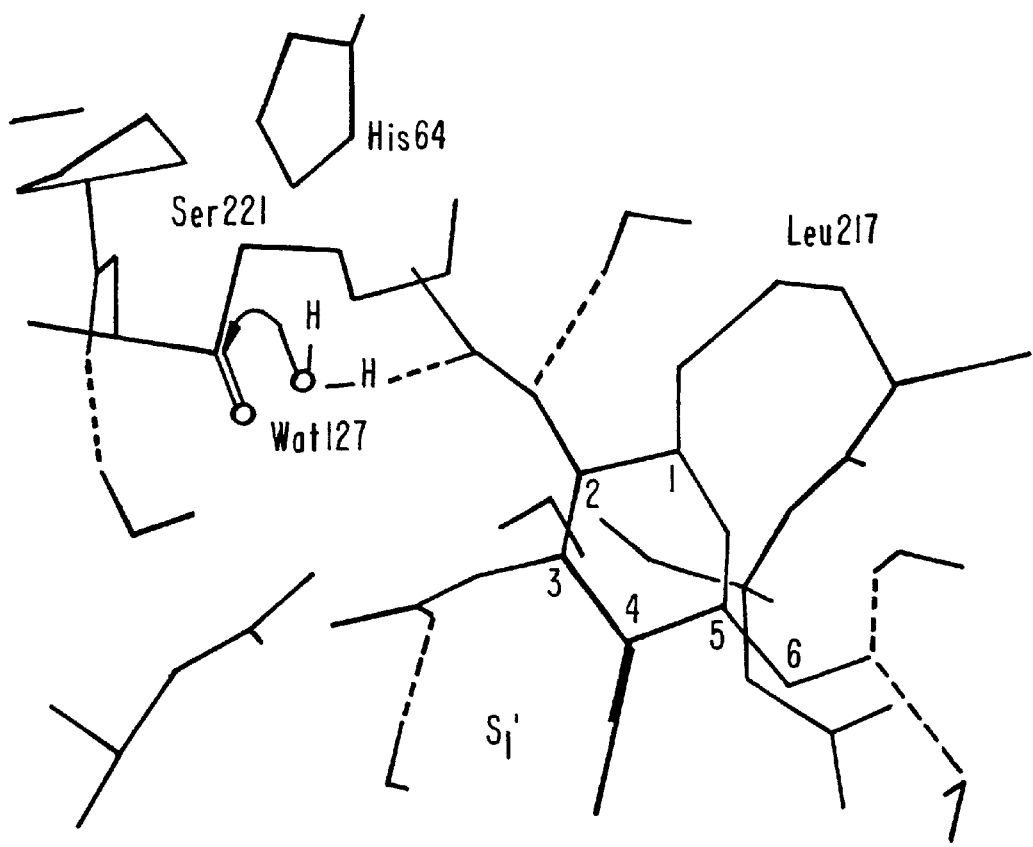

At position 62, in the $S_2$ pocket, with the exception of N62C-SEtβGal(Ac)$_3$ and N62C-SEtαMan(Ac)$_4$ (-i) (See FIG. 8), acetylation of N62C glyco-CMMs led to a reduction in E/A. However, like their deprotected counterparts, the acetylated N62C glyco-CMMs all had larger E/As than WT (FIG. 16A). Increasing the level of acetylation increased the E/A ratio from 2.1 -fold greater than WT for N62C-SFtβGlc $(Ac)_2$ to 3.0-fold greater than WT for N62C-SEtβGlc$(Ac)_3$. In spite of the general increases in E/A observed for the ethyl linked glyco-CMMs, the untethered CMM N62C-SβGlc $(Ac)_4$ (-a) (See FIG. 8) had an E/A very similar to WT.

At position 217, in the $S_1'$ pocket, L217C acetylated glyco CMMs all had enhanced E/As relative to WT (FIG. 16B). As for their deprotected counterparts, β-linked acetylated glyco-CMMs had higher E/As than that of the L217C mutant, whereas the E/As of the α-linked acetylated glyco-CMMs were lower than that of the mutant. In fact, modification at this site produced CMMs with by far the greatest enhancement of this ratio and the E/A for L217C-SβGlc $(Ac)_3$ was 17.2-fold greater than WT. In contrast to the L217C deprotected glyco-CMMs, introducing an ethyl linker lowered E/A from 17.2-fold greater than WT for L217C-SβGlc$(Ac)_3$ to 9.2-fold greater than WT for L217C-SEtβGlc$(Ac)_3$. For the untethered L217C acetylated glyco-CMMs, increasing the number of acetates also increased E/A, from 5.0-fold greater than WT for L217C-SEtβGlc $(Ac)_2$ to 17.2-fold greater than WT for L217C-SEtβGlc $(Ac)_3$.

At position 156, in the $S_1$ pocket, acetylation of α-linked glyco CMMs increased E/As (FIG. 16C). Hence, S156C-SEtβGlc$(Ac)_4$ (-h) (See FIG. 8) had an E/A that was 1.5 fold greater than WT whereas S156C-SEtαGlc$(Ac)_4$ (-g) (See FIG. 8) had an E/A 2.0-fold greater than WT. S156C-SEtαMan$(Ac)_4$ (-i) (See FIG. 8) also had an E/A 1.3-fold greater than that of its unacetylated counterpart, S156C-SEαMan (-d) (See FIG. 8).

At position 166, in the $S_1$ pocket, acetylation caused an increase in E/A for the glucosylated CMMs, irrespective of the anomeric stereochemistry (FIG. 16D). Acetylation of all other sugar moieties led to a reduction in E/A. Increasing the number of acetates increased E/A from 2.7-fold greater than WT for S166C-SEtβGlc$(Ac)_2$ to 3.2-fold greater than WT for S166C-SEtβGlc$(Ac)_3$.

Example 19

Molecular Modeling

The X-ray structure of subtilisin *Bacillus lentus* with the peptide inhibitor AAPF bound (Brookhaven database entry 1JEA) was used as the starting point for calculations on wild type and CMMs. The enzyme setup was performed with Insight II, version 2.3.0 (Biosym Technologies, Inc. San Diego, Calif.). To create initial coordinates for the minimization, hydrogens were added at the pH 8.6 used for kinetic measurements. This protonated all Lys and Arg residues and the N-terminus and deprotonated all Glu and Asp residues and the C-terminal carboxyl group. The protonated form of His 64 was used in all calculations. The model system was solvated with a 5 Å layer of water molecules. The total number of water molecules in the system was 1143. The overall charge of the enzyme-inhibitor complex resulting from this setup was +4 for the WT enzyme. Energy simulations were performed with the DISCOVER program, Version 2.9.5 (Biosym Technologies, Inc., San Diego, Calif.) on a Silicon Graphics Indigo computer, using the consistent valence force field (CVFF) function. A non-bonded cutoff distance of 18 Å with a switching distance of 2 Å was employed. The non-bonded pair list was updated every 20 cycles and a dielectric constant of 1 was used in all calculations. The WT enzyme was minimized in stages, with initially only the water molecules being allowed to move, followed by water molecules and the amino acid side chains, and then finally the entire enzyme. The mutated and chemically modified enzymes were generated by modifying the relevant amino acid using the Builder module of Insight. These structures were then minimized in a similar manner. Initially, the side-chain of the mutated residue and the water molecules were minimized. Then, all side-chains and the water molecules were minimized while the backbones of the residues were constrained, then all of the atoms were minimized. The AAPF inhibitor was free to move throughout all stages of the minimization. Each stage of energy minimization was conducted by means of the method of steepest descents without Morse or cross terms until the derivative of energy with respect to structural perturbation was less than 5.0 kcal/Å; then, the method of conjugate gradients, without Morse or cross terms until the derivative of energy with respect to structural perturbation was less than 1.0 kcal/Å; and, finally, the method of conjugate gradients, with Morse and cross terms until the final derivative of energy with respect to structural perturbation was less than 0.1 kcal/Å.

The molecular basis for the vastly improved esterase activities observed was analyzed by molecular modeling of the peptidyl product inhibitor AAPF bound to the SBL-CMM L217C-SβGlc$(Ac)_3$. While the substrate employed for kinetic analysis is succinylated, this moiety was not included in molecular modeling since its orientation was not reported in the X-ray structure of SBL, suggesting high mobility in the crystal.

As shown in FIGS. 17 and 18, molecular modeling analysis of L217C-SβGlc$(Ac)_3$ revealed that the observed $k_{cat}/K_M$ changes correlate with the occupation of the $S_1'$ pocket of SBL by the glucosylated -SβGlc(Ac), side chain. In the minimized structure (FIG. 17), the position of the glucose moiety was fixed by a network of hydrogen-bonding interactions (shown as white dotted lines) between the oxygen atoms on the C-3, 4, and 6 substituents of glucose and water molecules in the surrounding external solvent. This extensive solvation directed the C-2 substituent of glucose internally towards the catalytic triad. In this orientation, the carbonyl oxygen atom of the C-2 acetate group acts a hydrogen bond (1.89 Å) acceptor and stabilizes water molecule 127 in close proximity to the carboxy terminus of AAPF, used here as a substrate analog for modeling, and is shown in FIG. 17 hydrogen-bonding to the O atom of the carboxylic acid.

These results suggested that firstly the low amidase activity of L217C-S-Glc$(Ac)_3$, which was 2-fold lower than WT, was a result of the $S_1'$ pocket being occupied by the glucose moiety at position 217. This prevents efficient binding of the pNA leaving group and, therefore, decreases the rate of acyl-enzyme intermediate formation which is the rate-determining step for amidase activity. Secondly, after the pNA has been displaced to form the covalent Acyl-Ser221 intermediate, the glucose moiety stabilizes a crucial, nucleophilic water molecule (Wat 127) in close proximity to the carbonyl carbon atom, through a hydrogen-bond to the oxygen of the C-2 acetate of glucose, as illustrated in FIG. 18. This facilitates hydroylsis of the acyl-enzyme intermediate and therefore increases the rate of deacylation, which is the rate limiting step for esterase activity (Zerner et al., *J. Am. Chem. Soc.,* 86:3674–3679 (1964); Whitaker et al., *J. Am. Chem. Soc.,* 87:2728–2737 (1965); Berezin et al., *FEBS Lett.,* 15:121–124 (1971), which are hereby incorporated by reference).

Glycosylation of SBL at sites within the active site can dramatically enhance its esterase activity. The library of glycosylated CMMs synthesized using the combined site directed mutagenesis and chemical modification strategy contains 22 CMMs with greater than WT activity. Glycosylation at positions 62, in the $S_2$ pocket, and 217, in the $S_1$' pocket, gave the greatest increases in $k_{cat}/K_M$. The most active CMM L217C-SβGlc(Ac)$_3$ had a $k_{cat}/K_M$ that was 8.4-fold greater that WT and was the most active esterase synthesized using this approach. When surface exposed position 156 was glycosylated, there was little alteration in activity, and this demonstrates that the introduction of sugars at such sites has little effect on the catalytic activity of SBL.

In addition to the tailoring of esterase $k_{cat}/K_M$ values, glycosylation also led to enormous improvements in specificity for ester versus amide hydrolysis, as determined by measurement of the ratio $(k_{cat}/K_M)_{esteiase}/(k_{cat}/K_M)_{amidase}$, E/A. This ratio has been increased to 17.2-fold greater than WT for L217C-SβGlc(Ac)$_3$. Such enzymes are very attractive candidates for use in peptide synthesis, where a high esterase to amidase ratio is desirable. Furthermore, the CMMs described above have an even greater potential for this purpose, as the increases in E/As have been achieved by an increase in the catalytic efficiency of these enzymes towards ester substrates, in addition to a reduction in the amidase activity.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A method of producing a chemically modified mutant protein comprising the steps of: (a) providing a precursor protein; (b) substituting an amino acid residue other than cysteine in said precursor protein with a cysteine; (c) reacting said substituted cysteine with a glycosylated thiosulfonate, said glycosylated thiosulfonate comprising a carbohydrate moiety; and (d) obtaining a modified glycosylated protein wherein said substituted cysteine comprises a carbohydrate moiety attached thereto.

2. A method according to claim 1, wherein said thiosulfonate comprises an alkylthiosulfonate.

3. A method according to claim 2, wherein said alkylthiosulfoniate comprises a methanethiosulfonate.

4. A method according to claim 1, wherein the protein is an enzyme.

5. A method according to claim 4, wherein the enzyme is a protease.

6. A method according to claim 5, wherein the protease is a *Bacillus lentzits* subtilisin.

7. A method according to claim 1, wherein the amino acid residue other than cysteine is an amino acid selected from the group consisting of asparagine, leucine, and serine.

8. A method according to claim 1, wherein the amino acid residue other than cysteine is in a substrate binding subsite of the protein.

9. A method according to claim 1, wherein the glycosylated thiosulfonate comprises a thiol side chain comprising -S-β-Glc, -S-Et-β-Gal, -S-Et-β-Glc, -S-Et-α-Glc, -S-Et-α-Man, -S-Et-Lac, -S-β-Glc(Ac)$_2$, -S-β-Glc(Ac)$_3$, -S-β-Glc(Ac)$_4$, -S-Et-α-Glc(Ac)$_2$, -S-Et-α-Glc(Ac)$_3$, -S-Et-α-Glc(Ac)$_4$, -S-Et-β-Glc(Ac)$_2$, -S-Et-β-Glc(Ac)$_3$, -S-Et-β-Glc(Ac)$_4$, -S-Et-α-Man(Ac)$_3$, -S-Et-α-Man(Ac)$_4$, -S-Et-β-Gal(Ac)$_3$, -S-Et-β-Gal(Ac)$_4$, -S-Et-Lac(Ac)$_5$, -S-Et-Lac(Ac)$_6$, or -S-Et-Lac(Ac)$_7$.

10. A method according to claim 1, wherein the carbohydrate moiety is a dendrimer moiety.

* * * * *